United States Patent
Stoynova et al.

(10) Patent No.: US 12,338,481 B2
(45) Date of Patent: Jun. 24, 2025

(54) METHOD FOR PRODUCING 2-METHYL-BUTYRIC ACID BY BACTERIAL FERMENTATION

(71) Applicant: AJINOMOTO CO., INC., Tokyo (JP)

(72) Inventors: Natalia Viktorovna Stoynova, Moscow (RU); Elena Viktorovna Sycheva, Moscow (RU); Anna Alexandrovna Ublinskaya, Moscow (RU); Valery Vasilievich Samsonov, Moscow (RU); Alexandr Dmitrievich Kivero, Moscow (RU)

(73) Assignee: AJINOMOTO CO., INC., Tokyo (JP)

( * ) Notice: Subject to any disclaimer, the term of this patent is extended or adjusted under 35 U.S.C. 154(b) by 638 days.

(21) Appl. No.: 17/703,519

(22) Filed: Mar. 24, 2022

(65) Prior Publication Data
US 2022/0213515 A1    Jul. 7, 2022

Related U.S. Application Data

(63) Continuation of application No. PCT/JP2020/035935, filed on Sep. 24, 2020.

(30) Foreign Application Priority Data

Sep. 25, 2019  (RU) .......................... RU2019130090

(51) Int. Cl.
| | | |
|---|---|---|
| C12P 7/52 | (2006.01) | |
| C12N 9/04 | (2006.01) | |
| C12N 9/10 | (2006.01) | |
| C12N 9/88 | (2006.01) | |

(52) U.S. Cl.
CPC .............. *C12P 7/52* (2013.01); *C12N 9/0006* (2013.01); *C12N 9/1025* (2013.01); *C12N 9/1096* (2013.01); *C12N 9/88* (2013.01); *C12Y 101/01085* (2013.01); *C12Y 203/03013* (2013.01); *C12Y 206/01057* (2013.01); *C12Y 402/01033* (2013.01)

(58) Field of Classification Search
None
See application file for complete search history.

(56) References Cited

U.S. PATENT DOCUMENTS

| | | | |
|---|---|---|---|
| 6,146,859 | A | 11/2000 | Chen et al. |
| 7,700,328 | B2 | 4/2010 | Gatenby et al. |
| 9,540,652 | B2 | 1/2017 | Juminaga et al. |
| 2008/0102499 | A1 | 5/2008 | Templeton et al. |
| 2009/0081746 | A1 | 3/2009 | Liao et al. |
| 2010/0209986 | A1 | 8/2010 | Liao et al. |
| 2015/0132813 | A1 | 5/2015 | Zhang et al. |
| 2016/0264503 | A1 | 9/2016 | Theuerkauf et al. |
| 2022/0213515 | A1* | 7/2022 | Stoynova .............. C12N 9/1096 |

FOREIGN PATENT DOCUMENTS

| | | |
|---|---|---|
| CN | 100352928 C | 4/2006 |
| CN | 104531597 A | 4/2015 |
| CN | 106148259 A | 11/2016 |
| CN | 109266592 A | 1/2019 |
| CN | 109402034 A | 3/2019 |
| EP | 2147972 A1 | 1/2010 |
| JP | 5271606 B2 | 5/2013 |
| KR | 10-1869869 B1 | 7/2018 |
| WO | WO2010/045629 A2 | 4/2010 |
| WO | WO2013/169350 A1 | 11/2013 |
| WO | WO2017/156509 A1 | 9/2017 |

OTHER PUBLICATIONS

Wright, J., "2-Methyl Butyric Acid Use in berry, fruit, brown, fermented and savory flavors," Perfumer and Flavorist 2011;36:18-19.
Ullmann's Encyclopedia of Industrial Chemistry, 40 Volume Set, 7th Ed., 2011, Wiley-VCH, Flavors and Fragrances (only the pages referred to the specification).
Powell, J. T., et al., "Role of the *Escherichia coli* Aromatic Amino Acid Aminotransferase in Leucine Biosynthesis," J. Bacteriol. 1978;136(1):1-4.
Collier, R. H., et al., "Nonidentity of the Aspartate and the Aromatic Aminotransferase Components of Transaminase A in *Escherichia coli*," J. Bacteriol. 1972;112(1):365-371.
Vartak, N. B., et al., "A Functional leuABCD Operon Is Required for Leucine Synthesis by the Tyrosine-Repressible Transaminase in *Escherichia coli* K-12," J. Bacteriol. 1991; 173(12):3864-3871.
Lütke-Eversloh, T., et al., "Combinatorial pathway analysis for improved L-tyrosine production in *Escherichia coli*: Identification of enzymatic bottlenecks by systematic gene overexpression," Metab. Eng. 2008;10:69-77.
Zhang, C., et al., "Rational engineering of multiple module pathways for the production of L-phenylalanine in Corynebacterium glutamicum," J. Ind. Microbiol. Biotechnol. 2015;42:787-797.
Liu, S. P., et al., "A systems level engineered *E. coli* capable of efficiently producing L-phenylalanine," Process Biochem. 2014;49:751-757.
Wu Y.-Q., et al., "Co-expression of five genes in *E coli* for L-phenylalanine in Brevibacterium flavum," World J. Gastroenterol. 2003;9(2):342-346.
Fotheringham, I. G., et al., "Engineering of a Novel Biochemical Pathway for the Biosynthesis of L-2-aminobutyric Acid in *Escherichia coli* K12," Bioorg. Med. Chem. 1999;7:2209-2213.
Li, F.-F., et al., "Engineering *Escherichia coli* for production of 4-hydroxymandelic acid using glucose-xylose mixture," Microb. Cell Fact. 2016, 15:90, 11 pp.

(Continued)

*Primary Examiner* — Hope A Robinson
(74) *Attorney, Agent, or Firm* — Cermak & McGowan LLP; Shelly Guest Cermak

(57) ABSTRACT

The present invention provides a method for producing 2-methyl-butyric acid by fermentation using a bacterium belonging to the order Enterobacterales which has been modified to attenuate expression of a tyrB gene encoding a protein having tyrosine aminotransferase activity. The method also allows for production of a byproduct substance of 2-methyl-butyric acid during fermentation of the Enterobacterales bacterium having 2-methyl-butyric acid-producing ability.

7 Claims, 3 Drawing Sheets

Specification includes a Sequence Listing.

(56) References Cited

OTHER PUBLICATIONS

Zhu, Y., et al., "Metabolic engineering of indole pyruvic acid biosynthesis in *Escherichia coli* with tdiD," Microb. Cell Fact. 2017, 16:2, 15 pp.
Liu, S. P., et al., "Heterologous pathway for the production of L-phenylglycine from glucose by *E. coli*," J. Biotechnol. 2014;186:91-97.
Connor, M. R., et al., "Engineering of an *Escherichia coli* Strain for the Production of 3-Methyl-1-Butanol," Appl. Environmen. Microbiol. 2008;74(18):5769-5775.
International Search Report for PCT Patent App. No. PCT/JP2020/035935 (Feb. 3, 2021).
Written Opinion for PCT Patent App. No. PCT/JP2020/035935 (Feb. 3, 2021).

* cited by examiner ccctg*ttgaca*attaatcatcggctcg*tataat*gtgtggAATTGTGAGCGGATAACAATTtcacacagga

FIGURE 2

**MG Δtdh rhtA\* mini-Mu::P$_{lac}$-lacI-ilvA\*-kan**
**P$_L$-SD1-ilvG\*MEDA**
NS1547

↓ dacA::mini-Mu::cat-P$_{thr}$-ΔattB-thrA\*BC

↓ cat elimination

L1178-1

↓ cynX::cat-P$_L$-ilvA\*

↓ cat elimination

L1190-1

↓ trs5-10::cat-P$_{tac}$-kdcA-aldH

↓ cat elimination

L1194-2

↓ P$_L$-ilvG\*M-ΔilvE::cat-DA

↓ cat elimination

METHOD FOR PRODUCING
2-METHYL-BUTYRIC ACID BY BACTERIAL
FERMENTATION

This application is a Continuation of, and claims priority under 35 U.S.C. § 120 to, International Application No. PCT/JP2020/035935, filed Sep. 24, 2020, and claims priority therethrough under 35 U.S.C. § 119 to Russian Patent Application No. 2019130090, filed Sep. 25, 2019, the entireties of which are incorporated by reference herein. Also, the Sequence Listing filed electronically herewith is hereby incorporated by reference (File name: 2022-03-24T_US-635_seq_as_filed.txt; File size: 126 KB; Date recorded: Mar. 24, 2022).

BACKGROUND

General Field

The present invention relates to the microbiological industry, and specifically to a method for producing 2-methyl-butyric acid by fermentation of a bacterium belonging to the order Enterobacterales that has been modified to attenuate expression of a gene encoding a protein having tyrosine aminotransferase activity, so that production of a byproduct substance of 2-methyl-butyric acid is reduced, as compared with a non-modified bacterium.

Brief Description of the Related Art

2-Methyl-butyric acid is notably different in character from other compounds closely related by having a similar chemical structure regarding unbranched and branched aliphatic fatty acids, such as pentanoic acid (also referred to as "valeric acid") and 3-methyl-butyric acid (also referred to as "isovaleric acid"). 2-Methyl-butyric acid has a mild, soft, dried fruit character, whereas the related fatty acids are stronger, but much more cheesy in character. 2-Methyl butyric acid is widely distributed in nature and has a wide spectrum of use in the flavor industry (Wright J. 2-Methyl butyric acid. Use in berry, fruit, brown, fermented and savory flavors, Perfumer and flavorist, 2011, 36(7):18-19). In addition, lower alcohol esters of 2-methyl-butyric acid are used for production of fragrances, and polyol esters of 2-methyl-butyric acid are used for production of synthetic lubricants.

For particular applications, such as in the production of fragrances and some lubricants, demand is high for highly pure 2-methyl-butyric acid with only a residual amount of byproduct substances such as, for example, 3-methyl-butyric acid, that is, below 0.2% by weight. Therefore, demand is high for preparation methods of 2-methyl-butyric acid having a reduced amount of byproduct substances.

2-Methyl-butyric acid can be prepared using chemical synthesis or by fermentation of microorganisms in appropriate nutrient media. Commercially, 2-methyl-butyric acid is typically manufactured chemically by oxidizing 2-methyl-butyraldehyde which is generally produced by dehydrogenation of alcohols in the presence of a catalyst (Ullmann's Encyclopedia of industrial chemistry, 7$^{th}$ edition, 2011, Wiley-VCH). The alcohols are often inexpensive and available in good purity. Synthesis of 2-methyl-butyraldehyde via the oxo process (also called as "hydroformylation"), a process in which butenes are reacted with a mixture of carbon monoxide and hydrogen (so-called "synthesis gas") in the presence of transition metal compounds, is less suitable as the resultant products are often not sufficiently pure. To increase the purity of 2-methyl-butyric acid, a method for producing 2-methyl-butyric acid having a reduced amount of 3-methyl-butyric acid was developed (US20160264503 A1). The method includes controlling the composition of the butene feed mixture and optimization of the hydroformylation conditions, which are followed by catalytic hydrogenation reduction at elevated temperature and pressure and treatment by oxidizing agent. The resultant 2-methyl-butyric acid can be obtained with the amount of 3-methyl-butyric acid of less than 0.2% by weight.

Methods for producing 2-methyl-butyric acid by fermentation of bacteria include, for example, fermentative production of (S)-2-methyl-butyric acid using bacteria belonging to the genus Bacillus in an L-isoleucine-containing medium (JP5271606 B2). In another example, a 2-methyl-butyric acid-producing bacterium was constructed from E. coli L-threonine-producing strain ATCC 98082 by inactivation of a threonine exporter and an alcohol dehydrogenase encoded by the rhtA and yqhD genes, respectively, and introduction of native thrABC and artificial ilvAGMCD operons under the control of $P_L$lacO1 promoter on low-copy plasmids. The ability to produce 2-methyl-butyric acid was imparted to the bacterium by enhancing expression of genes encoding ketoacid decarboxylase and aldehyde dehydrogenase, which are responsible for the last two steps in the 2-methyl-butyric acid biosynthesis pathway (US20150132813 A1).

The tyrB gene encodes tyrosine aminotransferase (TyrB) which catalyzes the final step in tyrosine, leucine, and phenylalanine biosynthesis. The enzyme is feedback-inhibited by leucine (Powell J. T. and Morrison J. F., Role of the Escherichia coli aromatic amino acid aminotransferase in leucine biosynthesis, J. Bacteriol., 1978, 136(1):1-4), tyrosine (Collier R. H. and Kohlhaw G., Nonidentity of the aspartate and the aromatic aminotransferase components of transaminase A in Escherichia coli, J. Bacteriol., 1972, 112(1):365-371) and 2-keto-isovalerate (CN109402034 A; Vartak N. B. et al., A functional leuABCD operon is required for leucine synthesis by the tyrosine-repressible transaminase in Escherichia coli K-12, J. Bacteriol., 1991, 173(12):3864-3871).

Tyrosine aminotransferase TyrB having enhanced activity was used to construct L-tyrosine-producing strains (U.S. Pat. No. 9,540,652 B2, KR101869869 B1, CN109266592 A, US20080102499 A1, U.S. Pat. No. 7,700,328 B2; Lutke-Eversloh T. and Stephanopoulos G., Combinatorial pathway analysis for improved L-tyrosine production in Escherichia coli: identification of enzymatic bottlenecks by systematic gene overexpression, Metabolic engineering, 2008, 10(2): 69-77), L-phenylalanine (CN104531597 B, CN100352928 C; Zhang C. et. al., Rational engineering of multiple module pathways for the production of L-phenylalanine in Corynebacterium glutamicum, J. Ind. Microbiol. Biotechnol., 2015, 42(5):787-797; Liu S. P. et al., A systems level engineered E. coli capable of efficiently producing L-phenylalanine, Proc. Biochem., 2014, 49(5):751-757; Wo Y. Q. et al., Co-expression of five genes in E. coli for L-phenylalanine in Brevibacterium flavum, World J. Gastroenterol., 2003, 9(2):342-346), L-tryptophan (EP2147972 A1), L-homophenylalanine (U.S. Pat. No. 6,146,859 A), and L-2-aminobutyric acid (CN106148259 A; Fotheringham I. G. et al., Engineering of a novel biochemical pathway for the biosynthesis of L-2-aminobutyric acid in Escherichia coli K12, Bioorg. Med. Chem., 1999, 7(10):2209-2213).

Methods for reducing production of byproduct substances of target compounds by deleting or attenuating the tyrB gene have been reported (see, for example, Li F. F. et al., Engineering *Escherichia coli* for production of 4-hydroxymandelic acid using glucose-xylose mixture, *Microb. Cell Fact.*, 2016, 15:90; Zhu Y. et al., Metabolic engineering of indole pyruvic acid biosynthesis in *Escherichia coli* with tdiD, *Microb. Cell Fact.*, 2017, 16(1):2; Liu S. P. et al., Heterologous pathway for the production of L-phenylglycine from glucose by *E. coli*, *J. Biotechnol.*, 2014, 186:91-97).

In a series of reports, an *Escherichia coli* strain having increased expression of genes from the leucine biosynthesis pathway that can be used to generate 2-keto-isocaproate, and in which the ilvE and tyrB genes were deleted, was utilized in a method for production of alcohols, in particular, 3-methyl-1-butanol by fermentation of the bacterium (US2009081746 A1, US20100209986 A1, WO2010045629 A2; Connor M. R. and Liao J. C., Engineering of an *Escherichia coli* strain for the production of 3-methyl-1-butanol, *App. Env. Microbiol.*, 2008, 74(18):5769-5775). It was shown that elimination of the leucine synthesis genes ilvE and tyrB led to increased production of 2-keto-isocaproate, which can then be converted to 3-methyl-1-butanol via decarboxylation and reduction steps.

However, no data has been previously reported that describes the effect of attenuation of expression of tyrB gene on production of 2-methyl-butyric acid and byproduct substances of 2-methyl-butyric acid by fermentation of a 2-methyl-butyric acid-producing bacterium belonging to the order Enterobacterales. From the viewpoint of industrial production, reducing the amount of a byproduct substance of 2-methyl-butyric acid in a method for producing 2-methyl-butyric acid by fermentation of a bacterium belonging to the order Enterobacterales is of considerable importance as the improved method would allow production of highly pure 2-methyl-butyric acid at a low price.

SUMMARY

An improved method for producing 2-methyl-butyric acid by fermentation of a bacterium belonging to the order Enterobacterales is described herein. According to the presently disclosed subject matter, production of 2-methyl-butyric acid by fermentation of a bacterium belonging to the order Enterobacterales can be improved by attenuating expression of tyrB gene in the bacterium, so that production of a byproduct substance of 2-methyl-butyric acid such as, for example, 3-methyl-butyric acid, isobutyric acid, L-allo-isoleucine, and/or D-allo-isoleucine, by the modified bacterium can be reduced, as compared with a non-modified bacterium. When a bacterium belonging to the order Enterobacterales and modified to attenuate expression of the tyrB gene in the bacterium is cultured in a medium to produce 2-methyl-butyric acid, the amount of the byproduct substance of 2-methyl-butyric acid can be reduced further by attenuating expression of one or more of the leuABCD operon genes. As a result, 2-methyl-butyric acid can be produced at higher grade of purity and lower price as compared with a method in which the modified bacterium as described herein is not used.

It is one aspect of the present invention to provide a method for producing 2-methyl-butyric acid comprising: (i) cultivating in a culture medium a 2-methyl-butyric acid-producing bacterium belonging to the order Enterobacterales to produce and accumulate 2-methyl-butyric acid in the culture medium or cells of the bacterium, or both, and (ii) collecting 2-methyl-butyric acid from the culture medium or the cells of the bacterium, or both, wherein said bacterium has been modified to attenuate expression of a gene encoding a protein having tyrosine aminotransferase activity.

It is another aspect of the invention to provide the method as described above, wherein said gene encoding a protein having tyrosine aminotransferase activity is a tyrB gene.

It is another aspect of the invention to provide the method as described above, wherein said protein having tyrosine aminotransferase activity is selected from the group consisting of: (A) a protein comprising the amino acid sequence shown in SEQ ID NO: 2, (B) a protein comprising the amino acid sequence shown in SEQ ID NO: 2, but which includes substitution, deletion, insertion and/or addition of 1 to 150 amino acid residues, and wherein said protein has tyrosine aminotransferase activity, and (C) a protein comprising an amino acid sequence having an identity of not less than 60% with respect to the entire amino acid sequence shown in SEQ ID NO: 2, and wherein said protein has tyrosine aminotransferase activity.

It is another aspect of the invention to provide the method as described above, wherein said gene is selected from the group consisting of: (a) a gene comprising the nucleotide sequence shown in SEQ ID NO: 1, (b) a gene comprising a nucleotide sequence that is able to hybridize under stringent conditions with a nucleotide sequence complementary to the sequence shown in SEQ ID NO: 1, and wherein the gene encodes a protein having tyrosine aminotransferase activity, (c) a gene encoding a protein comprising the amino acid sequence shown in SEQ ID NO: 2, but which includes substitution, deletion, insertion and/or addition of 1 to 150 amino acid residues, and wherein said protein has tyrosine aminotransferase activity, and (d) a gene comprising a variant nucleotide sequence of SEQ ID NO: 1, wherein the variant nucleotide sequence is due to the degeneracy of the genetic code.

It is another aspect of the invention to provide the method as described above, wherein said expression of the gene encoding a protein having tyrosine aminotransferase activity is attenuated due to inactivation of the gene.

It is another aspect of the invention to provide the method as described above, wherein said gene encoding a protein having tyrosine aminotransferase activity is deleted.

It is another aspect of the invention to provide the method as described above, wherein said bacterium belongs to the family Enterobacteriaceae or Erwiniaceae.

It is another aspect of the invention to provide the method as described above, wherein said bacterium belongs to the genus *Escherichia* or *Pantoea*.

It is another aspect of the invention to provide the method as described above, wherein said bacterium is *Escherichia coli* or *Pantoea ananatis*.

It is another aspect of the invention to provide the method as described above, wherein said bacterium has been modified further to attenuate expression of a gene selected from the group consisting of leuA, leuB, leuC, leuD, and combinations thereof.

It is another aspect of the invention to provide the method as described above, wherein the amount of a byproduct substance of 2-methyl-butyric acid is reduced as compared with a non-modified bacterium.

It is another aspect of the invention to provide the method as described above, wherein the byproduct substance is selected from the group consisting of 3-methyl-butyric acid, isobutyric acid, L-allo-isoleucine, D-allo-isoleucine, and combinations thereof.

Still other objects, features, and attendant advantages of the present invention will become apparent to those skilled in the art from a reading of the following detailed description of embodiments constructed in accordance therewith.

BRIEF DESCRIPTION OF DRAWINGS

FIG. 2 shows the DNA sequence of $P_{tac}$ promoter (SEQ ID NO: 69). The −35 and −10 sequences of the $P_{tac}$ promoter are underlined. The lac repressor-binding site is indicated with capital letters. The sequence of $P_{tac}$ fragment which contains a half of lac operator is indicated in bold.

FIG. 3 shows the scheme for construction of an E. coli 2-methyl-butyric acid-producing strain L1201-1. SD1: modified Shine-Dalgarno sequence, *: mutant allele of a gene.

DETAILED DESCRIPTION OF THE EXEMPLARY EMBODIMENTS

Figure 1:
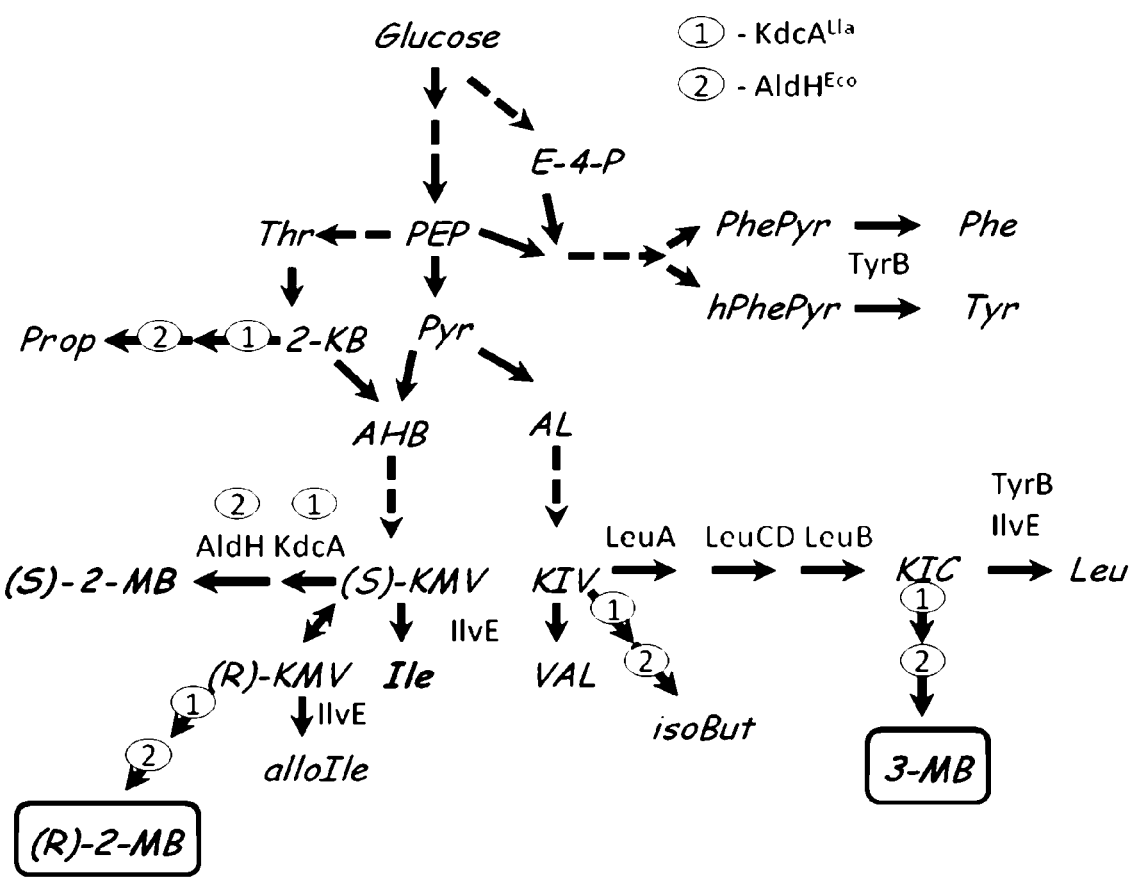
FIG. 1 shows the scheme of biosynthesis of 2-methyl-butyric acid and byproduct substances of 2-methyl-butyric acid. KdcA (also indicated as 1 in a circle): 2-ketoacid decarboxylase (EC 4.1.1.72) encoded by kdcA gene native to Lactococcus lactis those codons were optimized for the expression in E. coli, AldH (also indicated as 2 in a circle): aldehyde dehydrogenase (EC 1.2.1.3), IlvE: branched chain amino acid aminotransferase, aminotransferase B (EC 2.6.1.42), TyrB: aromatic amino acid aminotransferase (EC 2.6.1.57), LeuA: 2-isopropylmalate sythase (EC 2.3.3.13), LeuCD: 3-isopropylmalate dehydratase (EC 4.2.1.33), LeuB: 3-isopropylmalate dehydrogenase (EC 1.1.1.85), E-4-P: D-erythrose-4-phosphate, PEP: phosphoenolpyruvate, PhePyr: 3-phenyl-pyruvate, hPhePyr: 4-hydroxy-phenyl-pyruvate, Pyr: pyruvate, 2-KB: 2-keto-butanoate, Prop: propanoic acid, AHB: 2-aceto-2-hydroxy-butanoate, (S)-KMV: (S)-2-keto-3-methyl-valerate, (R)-KMV: (R)-2-keto-3-methyl-valerate, alloIle: allo-isoleucine, (S)-2-MB: (S)-2-methyl-butyric acid, (R)-2-MB: (R)-2-methyl-butyric acid, AL: 2-aceto-lactate, KIV: 2-keto-isovalerate, isoBut: isobutyric acid, KIC: 2-keto-isocaproate, 3-MB: 3-methyl-butyric acid.

The invention of the present application will now be described in more detail with reference to the exemplary embodiments, given only by way of example, and with reference to the accompanying figures.

1. Bacterium

The bacterium as described herein is a 2-methyl-butyric acid-producing bacterium belonging to the order Enterobacterales that has been modified to attenuate expression of a gene encoding a protein having tyrosine aminotransferase activity. The bacterium as described herein can be used in the method as described herein. Hence, the explanations given hereinafter to the bacterium can be similarly applied to any bacterium that can be used interchangeably or equivalently for the method as described herein.

Any 2-methyl-butyric acid-producing bacterium belonging to the order Enterobacterales and modified to attenuate expression of a gene encoding a protein having tyrosine aminotransferase activity can be used.

The phrase "a 2-methyl-butyric acid-producing bacterium" may be used interchangeably or equivalently to the phrase "a bacterium that is able to produce 2-methyl-butyric acid", the phrase "a bacterium having an ability to produce 2-methyl-butyric acid", or the phrase "a bacterium having a 2-methyl-butyric acid-producing ability".

The phrase "2-methyl-butyric acid-producing bacterium" can mean a bacterium belonging to the order Enterobacterales that has an ability to produce, excrete or secrete, and/or cause accumulation of 2-methyl-butyric acid in a culture medium and/or cells of the bacterium (i.e. the bacterial cells) when the bacterium is cultured in the medium.

The phrase "2-methyl-butyric acid-producing bacterium" can also mean a bacterium that is able to produce, excrete or secrete, and/or cause accumulation of 2-methyl-butyric acid in a culture medium in an amount larger than a non-modified bacterium. The term "a non-modified bacterium" may be used interchangeably or equivalently to the term "a non-modified strain". The term "a non-modified strain" can mean a control strain that has not been modified to attenuate expression of a gene encoding a protein having tyrosine aminotransferase activity. Examples of the non-modified strain can include a wild-type or parental strain, such as E. coli K-12 strains such as W3110 (ATCC 27325) and MG1655 (ATCC 47076). The term "2-methyl-butyric acid-producing bacterium" can also mean a bacterium that is able to cause accumulation in a culture medium of an amount, for example, not less than 0.1 g/L, not less than 0.5 g/L, or not less than 1.0 g/L of 2-methyl-butyric acid.

Furthermore, the bacterium belonging to the order Enterobacterales and modified to attenuate expression of a gene encoding a protein having tyrosine aminotransferase activity such as tyrB gene, which has 2-methyl-butyric acid-producing ability, can also be used. The bacterium may inherently have 2-methyl-butyric acid-producing ability or may be modified to have 2-methyl-butyric acid-producing ability. Such modification can be attained by using, for example, a mutation method or DNA recombination techniques. The bacterium can be obtained by attenuating expression of a gene encoding a protein having tyrosine aminotransferase activity such as tyrB gene in a bacterium that inherently has 2-methyl-butyric acid-producing ability. Alternatively, the bacterium can be obtained by imparting 2-methyl-butyric acid-producing ability to a bacterium already modified to attenuate expression of a gene encoding a protein having tyrosine aminotransferase activity such as tyrB gene. Alternatively, the bacterium may have been imparted with 2-methyl-butyric acid-producing ability by being modified to attenuate expression of a gene encoding a protein having tyrosine aminotransferase activity such as tyrB gene. The bacterium as described herein can be obtained, specifically, for example, by modifying a bacterial strain described hereinafter.

The phrase "2-methyl-butyric acid-producing ability" can mean the ability of a bacterium belonging to the order Enterobacterales to produce, excrete or secrete, and/or cause accumulation of 2-methyl-butyric acid in a culture medium and/or the bacterial cells. The phrase "2-methyl-butyric acid-producing ability" can specifically mean the ability of the bacterium to produce, excrete or secrete, and/or cause accumulation of 2-methyl-butyric acid in a culture medium and/or the bacterial cells to such a level that 2-methyl-butyric acid can be collected from the culture medium and/or the bacterial cells, when the bacterium is cultured in the medium.

The term "cultured" with reference to a bacterium which is grown in a medium and used according to the method as described herein may be used interchangeably or equivalently to the terms "cultivated", "grown", or the like, that are well-known to persons skilled in the art.

The bacterium can produce 2-methyl-butyric acid in S-form or R-form enantiomers of the 2-methyl-butyric acid, or as a mixture of S-form and R-form of the enantiomers in various proportions. Among these, an S-form of enantiomer is a particular example.

The bacterium can produce 2-methyl-butyric acid either alone or as a mixture of 2-methyl-butyric acid and one or more kinds of substances that are different from 2-methyl-butyric acid. For example, the bacterium can produce 2-methyl-butyric acid either alone, or a mixture of 2-methyl-butyric acid and one or more kinds of amino acids, for example, amino acids in L-form (also referred to as "L-amino acids"). Furthermore, the bacterium can produce 2-methyl-butyric acid either alone or as a mixture of 2-methyl-butyric acid and one or more kinds of other organic acids such as, for example, carboxylic acids that are different from 2-methyl-butyric acid.

Furthermore, any 2-methyl-butyric acid-producing bacterium belonging to the order Enterobacterales and modified to attenuate expression of a gene encoding a protein having tyrosine aminotransferase activity such as tyrB gene, such that production of a byproduct substance of 2-methyl-butyric acid is reduced as compared with a non-modified strain, for example, a wild-type or parental strain as described hereinafter, can be used. The byproduct substance can consist of one, two, or more kinds of substances. That is, specifically, the bacterium can be used, which is modified to attenuate expression of a gene encoding a protein having tyrosine aminotransferase activity such as tyrB gene and which is able to produce one, two, or more kinds of byproduct substances of 2-methyl-butyric acid at a lower amount as compared with a non-modified bacterium, or by which by-production of one, two, or more kinds of byproduct substances of 2-methyl-butyric acid is reduced as compared with a non-modified bacterium. The amount of a byproduct substance of 2-methyl-butyric acid may be expressed as an absolute value such as, for example, in grams per liter (g/L), and the like, or a relative value such as, for example, in %. That is, the production amount of a byproduct substance of 2-methyl-butyric acid in terms of an absolute value and/or a relative value may be reduced. The phrase "an amount of a byproduct substance of 2-methyl-butyric acid is expressed as a relative value" can mean that an amount of a byproduct substance of 2-methyl-butyric acid is expressed as a ratio of the amount of the byproduct substance of 2-methyl-butyric acid relative to a reference substance and is, preferably, multiplied by 100%. A particular example of "a reference substance" can be 2-methyl-butyric acid. It is, therefore, acceptable that when a method for producing 2-methyl-butyric acid as described herein is used, an absolute amount of a byproduct substance of 2-methyl-butyric acid which is produced by a modified bacterium can remain unchanged or even be increased as compared with a non-modified bacterium, whereas the relative amount of the byproduct substance is decreased as compared with a non-modified bacterium, so that 2-methyl-butyric acid can be produced at a higher grade of purity as compared with a method in which the modified bacterium as described herein is not used.

The phrase "able to produce a byproduct substance of 2-methyl-butyric acid" as used herein with regard to a bacterium can mean the ability of a bacterium belonging to the order Enterobacterales to produce, excrete or secrete, and/or cause accumulation of one, two or more kinds of byproduct substances of 2-methyl-butyric acid in a culture medium or the bacterial cells. The phrase "able to produce a byproduct substance of 2-methyl-butyric acid" as used herein with regard to a bacterium can specifically mean the ability of a bacterium belonging to the order Enterobacterales to produce, excrete or secrete, and/or cause accumulation of one, two, or more kinds of byproduct substances of 2-methyl-butyric acid in a culture medium or the bacterial cells, or both, to such a level that the one, two, or more byproduct substances of 2-methyl-butyric acid can be collected from the culture medium and/or the bacterial cells when the bacterium is cultured in the medium. The phrase "a byproduct substance of 2-methyl-butyric acid" is explained hereinafter.

Examples of L-amino acids include, but are not limited to, L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine, and derivatives thereof.

Examples of carboxylic acids include, but are not limited to, formic acid, acetic acid, propionic acid, butyric acid, lactic acid, citric acid, and pentanoic acid, and derivatives thereof.

The terms "L-amino acid" and "carboxylic acid" can refer not only to an amino acid and a carboxylic acid in a free form, but can also refer to a derivative form thereof, such as a salt, a hydrate, an adduct, or a combination of these. An adduct can be a compound formed by the amino acid or the carboxylic acid and another organic or inorganic compound. Hence, the terms "L-amino acid" and "carboxylic acid" can mean, for example, an L-amino acid and a carboxylic acid in a free form, a derivative form, or a mixture of them. The terms "L-amino acid" and "carboxylic acid" can particularly mean, for example, an L-amino acid and a carboxylic acid in a free form, a salt thereof, or a mixture of these. The terms "L-amino acid" and "carboxylic acid" can mean, for example, any of sodium, potassium, ammonium, mono-, di- and trihydrate, mono- and dichlorhydrate, and salts thereof. Unless otherwise stated, the terms "L-amino acid" and "carboxylic acid" without referring to hydration, such as the phrases "an L-amino acid or a carboxylic acid in a free form" and "a salt of an L-amino acid or a carboxylic acid", can refer to an L-amino acid and a carboxylic acid not in a hydrate form, a hydrate of an L-amino acid and a carboxylic acid, or or a mixture of these.

The phrase "a byproduct substance of 2-methyl-butyric acid" can refer to one, two or more byproduct substances of 2-methyl-butyric acid and can mean a substance, such as, for example, an organic compound, which is different from 2-methyl-butyric acid and which is produced as a byproduct, co-product, or side-product in a method for production of 2-methyl-butyric acid by fermentation of a bacterium as described herein. The phrase "a byproduct substance of 2-methyl-butyric acid" can also refer to a substance that can be produced and excreted or secreted by a 2-methyl-butyric acid-producing bacterium belonging to the order Enterobacterales when the bacterium is cultured to produce 2-methyl-butyric acid, such that the byproduct substance accumulates in a culture medium or the bacterial cells, or both, to such a level that the byproduct substance can be collected from the culture medium and/or the bacterial cells when the bacterium is cultured in the medium. An amount of a byproduct substance of 2-methyl-butyric acid in the culture medium and/or the bacterial cells can be lower, equal, or higher than the amount of 2-methyl-butyric acid produced by fermentation of a bacterium belonging to the order Enterobacterales that has an ability to produce 2-methyl-butyric acid.

As 2-methyl-butyric acid biosynthesis pathway branches off from the biosynthesis pathway of L-isoleucine, specific examples of a byproduct substance of 2-methyl-butyric acid include, but are not limited to, intermediates in a biosynthesis pathway of 2-methyl-butyric acid, and intermediates of other biosynthesis pathways, from which the biosynthesis pathway of 2-methyl-butyric acid branches off, and so forth, or their combination. The intermediate is not limited to an intermediate in the biosynthesis pathway of 2-methyl-butyric acid, and it also may be a precursor, an intermediate, or a substrate in a metabolic pathway of other one, two, or more substances, for example, a precursor, an intermediate, or a substrate in a biosynthesis pathway of a branched-chain L-amino acid.

The phrase "a branched-chain L-amino acid" can refer to an L-amino acid such as L-valine, L-leucine, and L-isoleucine. As pyruvate, which may be also referred to as "alpha-ketopropionic acid", is a precursor in the biosynthesis pathways of L-valine, L-leucine, and L-isoleucine, a byproduct of 2-methyl-butyric acid can be the byproduct of another biosynthesis pathway that branches off from pyruvate in the biosynthesis pathway of 2-methyl-butyric acid. A byproduct substance of 2-methyl-butyric acid is a particular example of the byproduct of another biosynthesis pathway that branches off from pyruvate in the biosynthesis pathway of 2-methyl-butyric acid, and can include 3-methyl-butyric acid and isobutyric acid that have the common precursor 2-keto-isovalerate, which may be also referred to as "alpha-oxoisovaleric acid", L-allo-isoleucine and D-allo-isoleucine that have the common precursor 2-keto-3-methyl-valerate, which may be also referred to as "alpha-oxomethylvaleric acid", which 2-keto-isovalerate and 2-keto-3-methyl-valerate have the common precursor pyruvate (FIG. 1).

Therefore, a byproduct substrate of 2-methyl-butyric acid may be, but is not limited to, 3-methyl-butyric acid, isobutyric acid, L-allo-isoleucine, D-allo-isoleucine or a combination thereof, in a method for producing 2-methyl-butyric acid by fermentation of a bacterium belonging to the order Enterobacterales and modified to attenuate expression of a gene encoding a protein having tyrosine aminotransferase activity as described hereinafter.

The bacteria belonging to the family Enterobacteriaceae were recently reclassified based on a comprehensive comparative genomic analyses, which includes phylogenetic reconstructions based on 1548 core proteins, 53 ribosomal proteins, and four multilocus sequence analysis proteins (Adelou M. et al., Genome-based phylogeny and taxonomy of the 'Enterobacteriales': proposal for Enterobacterales ord. nov. divided into the families Enterobacteriaceae, Erwiniaceae fam. nov., Pectobacteriaceae fam. nov., Yersiniaceae fam. nov., Hafniaceae fam. nov., Morganellaceae fam. nov., and Budviciaceae fam. nov., *Int. J. Syst. Evol. Microbiol.*, 2016, 66:5575-5599).

According to the reclassification, the genera previously belonging to the family Enterobacteriaceae now are a part of different families within the order Enterobacterales. Based on the above analyses, a bacterium that can be used in the method as described herein and belonging to the order Enterobacterales can be from the genera *Enterobacter, Escherichia, Klebsiella, Salmonella, Erwinia, Pantoea, Morganella, Photorhabdus, Providencia, Yersinia*, and so forth, and can have the ability to produce 2-methyl-butyric acid. Specifically, those classified into the order Enterobacterales according to the taxonomy used in the NCBI (National Center for Biotechnology Information) database (ncbi.nlm.nih.gov/Taxonomy/Browser/www-tax.cgi?id=91347) can be used. Examples of strains belonging to the order Enterobacterales that can be modified include a bacterium of the family Enterobacteriaceae or Erwiniaceae, and, specifically, the genus *Escherichia, Enterobacter*, or *Pantoea*.

The *Escherichia* bacterial species are not particularly limited, and examples include species classified into the genus *Escherichia* according to the taxonomy known to those skilled in the field of microbiology. Examples of the *Escherichia* bacterium include, for example, those described in the work of Neidhardt et al. (Bachmann B. J., Derivations and genotypes of some mutant derivatives of *E. coli* K-12, p. 2460-2488. In F. C. Neidhardt et al. (ed.), *E. coli* and *Salmonella*: cellular and molecular biology, $2^{nd}$ ed. ASM Press, Washington, D.C., 1996). The species *Escherichia coli* (*E. coli*) is a particular example of *Escherichia* bacteria. Specific examples of *E. coli* include *E. coli* K-12 strain, which is a prototype wild-type strain, such as *E. coli* W3110 (ATCC 27325), *E. coli* MG1655 (ATCC 47076), and so forth.

The *Enterobacter* bacteria are not particularly limited, and examples include species classified into the genus *Enterobacter* according to classification known to a person skilled in the art of microbiology. Examples of the *Enterobacter* bacterium include, for example, *Enterobacter agglomerans, Enterobacter aerogenes*, and so forth. Specific examples of *Enterobacter agglomerans* strains include, for example, the *Enterobacter agglomerans* ATCC 12287. Specific examples of *Enterobacter aerogenes* strains include, for example, the *Enterobacter aerogenes* ATCC 13048, NBRC 12010 (Sakai S. and Yaqishita T., Microbial production of hydrogen and ethanol from glycerol-containing wastes discharged from a biodiesel fuel production plant in a bioelectrochemical reactor with thionine, *Biotechnol. Bioeng.*, 2007, 98(2):340-348), and AJ110637 (FERM BP-10955). Examples of the *Enterobacter* bacterial strains also include, for example, the strains described in European Patent Application Laid-open (EP-A) No. 0952221. In addition, *Enterobacter agglomerans* also include some strains classified as *Pantoea agglomerans*.

The *Pantoea* bacteria are not particularly limited, and examples include species classified into the genus *Pantoea* according to classification known to a person skilled in the art of microbiology. Examples of the *Pantoea* bacterial species include, for example, *Pantoea ananatis* (*P. ananatis*), *Pantoea stewartii, Pantoea agglomerans*, and *Pantoea citrea*. Specific examples of *P. ananatis* strains include, for example, the *P. ananatis* LMG20103, AJ13355 (FERM BP-6614), AJ13356 (FERM BP-6615), AJ13601 (FERM BP-7207), SC17 (FERM BP-11091), and SC17(0) (VKPM B-9246). Some strains of *Enterobacter agglomerans* were recently reclassified into *Pantoea agglomerans, Pantoea ananatis, Pantoea stewartii*, or the like on the basis of nucleotide sequence analysis of 16S rRNA etc. (Mergaert J. et al., Transfer of *Envinia ananas* (synonym, *Erwinia uredovora*) and *Envinia stewartii* to the Genus *Pantoea* emend. as *Pantoea ananas* (Serrano 1928) comb. nov. and *Pantoea stewartii* (Smith 1898) comb. nov., respectively, and description of *Pantoea stewartii* subsp. indologenes subsp. nov., *Int. J. Syst. Evol. Microbiol.*, 1993, 43:162-173). The *Pantoea* bacteria include those reclassified into the genus *Pantoea* as described above.

Examples of the *Erwinia* bacteria include *Envinia amylovora* and *Envinia carotovora*. Examples of the *Klebsiella* bacteria include *Klebsiella planticola*.

These strains are available from, for example, the American Type Culture Collection (Address: P.O. Box 1549, Manassas, VA 20108, United States of America). That is, registration numbers are given to the respective strains, and the strains can be ordered by using these registration numbers (refer to atcc.org). The registration numbers of the strains are listed in the catalogue of the American Type Culture Collection.

The bacterium may be a bacterium inherently having a 2-methyl-butyric acid-producing ability or may be a bacterium modified so that it has 2-methyl-butyric acid-producing ability. The bacterium having a 2-methyl-butyric acid-producing ability can be obtained by imparting a 2-methyl-butyric acid-producing ability to such a bacterium as mentioned above, or by enhancing a 2-methyl-butyric acid-producing ability of such a bacterium as mentioned above.

To impart or enhance a 2-methyl-butyric acid-producing ability, methods conventionally employed in the breeding of amino acid-producing strains of *Escherichia* bacteria, and so forth (see "Amino Acid Fermentation", Gakkai Shuppan Center (Ltd.), 1st Edition, published May 30, 1986, pp. 77-100) can be used. Examples of such methods include, for example, acquiring an auxotrophic mutant strain, acquiring a 2-methyl-butyric acid analogue-resistant strain, acquiring a metabolic regulation mutant strain, and constructing a recombinant strain in which the activity of a 2-methyl-butyric acid biosynthetic enzyme is enhanced. In the breeding of 2-methyl-butyric acid-producing bacteria, one of the above-described properties such as auxotrophy, analogue resistance, and metabolic regulation mutation may be imparted alone, or two, or three, or more of such properties may be imparted in combination. Also, in the breeding of 2-methyl-butyric acid-producing bacteria, the activity of one of 2-methyl-butyric acid biosynthetic enzymes may be enhanced alone, or the activities of two or three or more of such enzymes may be enhanced in combination. Furthermore, imparting property(s) such as auxotrophy, analogue resistance, and metabolic regulation mutation can be combined with enhancing the activity(s) of biosynthetic enzyme(s).

An auxotrophic mutant strain, analogue-resistant strain, or metabolic regulation mutant strain having a 2-methyl-butyric acid-producing ability can be obtained by subjecting a parental strain or wild-type strain to a typical mutagenesis treatment, and then selecting a strain exhibiting auxotrophy, analogue resistance, or a metabolic regulation mutation, and having a 2-methyl-butyric acid-producing ability from the obtained mutant strains. Examples of typical mutagenesis treatments include irradiation of X-ray or ultraviolet and a treatment with a mutation agent such as N-methyl-N'-nitro-N-nitrosoguanidine (MNNG), ethyl methanesulfonate (EMS), and/or methyl methanesulfonate (MMS).

A 2-methyl-butyric acid-producing ability can also be imparted or enhanced by enhancing the activity of an enzyme involved in biosynthesis of 2-methyl-butyric acid. An enzyme activity can be enhanced by, for example, modifying a bacterium so that the expression of a gene encoding the enzyme is enhanced. Methods for enhancing gene expression are described in WO0018935, EP1010755 A, and so forth.

Furthermore, a 2-methyl-butyric acid-producing ability can also be imparted or enhanced by reducing the activity of an enzyme that catalyzes a reaction branching away from the biosynthesis pathway of 2-methyl-butyric acid to generate a compound other than the 2-methyl-butyric acid. The "enzyme that catalyzes a reaction branching away from the biosynthesis pathway of 2-methyl-butyric acid to generate a compound other than the 2-methyl-butyric acid" includes an enzyme involved in decomposition of the 2-methyl-butyric acid. An enzyme activity can be reduced by, for example, modifying a bacterium so that the gene encoding the enzyme is inactivated. The method for reducing enzyme activity will be described later.

Hereafter, 2-methyl-butyric acid-producing bacteria and methods for imparting or enhancing a 2-methyl-butyric acid-producing ability will be specifically exemplified. All of the properties of the 2-methyl-butyric acid-producing bacteria and modifications for imparting or enhancing a 2-methyl-butyric acid-producing ability may be used independently or in any appropriate combination.

2-Methyl-Butyric Acid-Producing Bacteria

Examples of 2-methyl-butyric acid-producing bacteria and parental strains which can be used to derive 2-methyl-butyric acid-producing bacteria include, but are not limited to, strains in which the expression of one or more genes encoding proteins responsible for the last two steps in the 2-methyl-butyric acid biosynthesis pathway is enhanced (FIG. 1). Examples of genes encoding proteins responsible for the penultimate step in the 2-methyl-butyric acid biosynthesis pathway include the kivD gene encoding branched-chain-2-ketoacid decarboxylase (KivD), which can be native to, for example, *Lactococcus lactis* (US20150132813 A1; de la Plaza et al., Biochemical and molecular characterization of alpha-keto-isovalerate decarboxylase, an enzyme involved in the formation of aldehydes from amino acids by *Lactococcus lactis*, FEMS Microbiol Lett., 2004, 238(2):367-374), the kdcA gene encoding branched-chain 2-ketoacid decarboxylase, which can be native to, for example, *Lactococcus lactis* B1157 that shows 89.8% identity with KivD (Smit B. A. et al., Identification, cloning, and characterization of a *Lactococcus lactis* branched-chain α-ketoacid decarboxylase involved in flavor formation, *Appl. Env. Microbiol.*, 2005, 71(1):303-311; Savrasova E. A. et al., Use of the valine biosynthesis pathway to convert glucose into isobutanol, *J. Ind. Microbiol. Biotechnol.*, 2011, 38(9):1287-1294), and ipdC gene encoding indolepyruvate decarboxylase, which can be native to, for example, *Salmonella typhimurium* (US20150132813 A1). Examples of genes encoding proteins responsible for the ultimate step in the 2-methyl-butyric acid biosynthesis pathway include the feaB gene (synonym: padA gene) encoding phenylacetaldehyde dehydrogenase, which can be native to, for example, *E. coli* (US20150132813 A1; Rodriguez-Zavala J. S. et al., Characterization of *E. coli* tetrameric aldehyde dehydrogenases with atypical properties compared to other aldehyde dehydrogenases, *Protein Sci.*, 2006, 15(6):1387-1396), the aldB gene encoding aldehyde dehydrogenase, which can be native to, for example, *E. coli* (US20150132813 A1; Ho K. K. and Weiner H., Isolation and characterization of an aldehyde dehydrogenase encoded by the aldB gene of *Escherichia coli*, *J. Bacteriol.*, 2005, 187(3):1067-1073), and the puuC gene (synonym: aldH gene) encoding γ-glutamyl-γ-aminobutyraldehyde dehydrogenase, which can be native to, for example, *E. coli* (US20150132813 A1; Kurihara S. et al., A novel putrescine utilization pathway involves γ-glutamylated intermediates of *Escherichia coli* K-12, *J. Biol. Chem.*, 2005, 280(6):4602-4608; Jo J.-E. et al., Cloning, expression, and characterization of an aldehyde dehydrogenase from *Escherichia coli* K-12 that utilizes 3-hydroxypropionaldehyde as a substrate, *Appl. Microbiol. Biotechnol.*, 2008, 81(1):51-60).

As 2-methyl-butyric acid biosynthesis pathway branches off from 2-keto-3-methyl-valerate in the biosynthesis pathway of L-isoleucine, examples of 2-methyl-butyric acid-producing bacteria and parent strains which can be used to derive 2-methyl-butyric acid-producing bacteria, include but are not limited to, recombinant strains transformed with genes encoding proteins involved in L-isoleucine biosynthesis, such as threonine deaminase (JP 2-458 A) and acetohydroxy acid synthase (EP0356739 A1). Other examples of L-isoleucine-producing bacteria and parental strains which can be used to derive 2-methyl-butyric acid-producing bacteria include, but are not limited to, strains belonging to the genus *Escherichia* such as *E. coli* AJ12919 (Japanese Patent Laid-open Publication No. 8-47397); *E. coli* strains VL1892 and KX141 (VKPM B-4781) (US5658766), and the like.

As the L-isoleucine biosynthesis pathway starts from L-threonine, examples of 2-methyl-butyric acid-producing bacteria and parent strains which can be used to derive 2-methyl-butyric acid-producing bacteria, can also include, but are not limited to, strains in which expression of one or more genes encoding an L-threonine biosynthetic enzyme(s) is enhanced. For example, to enhance expression of the threonine operon thrABC, the attenuator region which affects the transcription is desirably removed from the operon (WO2005049808 A1, WO2003097839 A1). Other examples of L-threonine-producing bacteria and parental strains which can be used to derive 2-methyl-butyric acid-producing bacteria include, but are not limited to, strains belonging to the genus *Escherichia* such as *E. coli* TDH-6/pVIC40 (VKPM B-3996) (U.S. Pat. Nos. 5,175,107 and 5,705,371), *E. coli* 472T23/pYN7 (ATCC 98081) (U.S. Pat. No. 5,631,157), *E. coli* NRRL-21593 (U.S. Pat. No. 5,939,307), *E. coli* MG442 (U.S. Pat. No. 4,278,765; Gusyatiner M. M. et al., Study of relA gene function in the expression of amino acid operons. II. Effect of the relA gene allelic state on threonine over-production by *Escherichia coli* K-12 mutants resistant to β-hydroxynorvaline acid, *Genetika* (Russian), 1978, 14(6):957-968), *E. coli* VL643 and VL2055 (EP1149911 A2), *E. coli* VKPM B-5318 (EP0593792 A1), and the like.

Based on the above L-threonine-producing strain VKPM B-3996, L-isoleucine-producing strain AJ12919 was obtained by introducing the ilvGMEDA operon on the plasmid pMWD5 containing the ilvA gene encoding threonine deaminase, of which inhibition by L-isoleucine is substantially desensitized and from which a region required for attenuation is removed (EP0685555 B1).

A 2-methyl-butyric acid-producing bacterium can be obtained from any L-isoleucine-producing bacterium by inactivation of branched-chain amino acid aminotransferase encoded by ilvE gene. Methods for inactivation of genes are described herein.

The genes and proteins used for breeding 2-methyl-butyric acid-producing bacteria may have, for example, known nucleotide sequences and amino acid sequences of the genes and proteins exemplified above, respectively. Also, the genes and proteins used for breeding 2-methyl-butyric acid-producing bacteria may be variants of the genes and proteins exemplified above, such as variants of genes and proteins having known nucleotide sequences and amino acid sequences, respectively, so long as the original function thereof, such as respective enzymatic activities in cases of proteins, is maintained. As for variants of genes and proteins, the descriptions concerning variants of a gene encoding a protein having tyrosine aminotransferase activity and tyrosine aminotransferase encoded thereby described herein can be similarly applied.

The bacterium as described herein belonging to the order Enterobacterales has been modified to, at least, attenuate expression of a gene encoding a protein having tyrosine aminotransferase activity.

The phrase "a gene encoding a protein having tyrosine aminotransferase activity" can mean a gene encoding the protein having enzymatic activity of catalyzing the following reactions: an aromatic amino acid+2-ketoglutarate↔an aromatic 2-ketoacid+L-glutamate (Enzyme Commission number, EC: 2.6.1.57) and L-leucine+2-ketoglutarate↔4-methyl-2-keto-pentanoate+L-glutamate (EC: 2.6.1.6). A specific example of the gene which encodes the enzyme having tyrosine aminotransferase activity includes the tyrB gene which encodes tyrosine aminotransferase. The gene encoding an enzyme having tyrosine aminotransferase activity can be the tyrB gene and its homolog(s) or variant nucleotide sequence(s). The more specific description of tyrB and its homologs and variant nucleotide sequences is given hereinafter.

The tyrB gene encodes tyrosine aminotransferase TyrB (synonym: aromatic-amino-acid aminotransferase, leucine aminotransferase) (KEGG, Kyoto Encyclopedia of Genes and Genomes, entry No. b4054; Protein Knowledgebase, UniProtKB/Swiss-Prot, accession No. P04693).

The tyrB gene (GenBank, accession No. NC_000913.3; nucleotide positions: 4267114 to 4268307, complement; Gene ID: 948563) is located between the alr gene on the same strand and the yjbS gene on the opposite strand on the chromosome of *E. coli* strain K-12. The nucleotide sequence of the tyrB gene (SEQ ID NO: 1) of *E. coli* strain K-12 and the amino acid sequence of the TyrB protein (SEQ ID NO: 2) encoded by this gene native to *E. coli* strain K-12 are known.

That is, the gene encoding a protein having tyrosine aminotransferase activity such as the tyrB gene may be a gene, such as DNA, having the nucleotide sequence of SEQ ID NO: 1, and the protein having tyrosine aminotransferase activity such as the TyrB protein may be a protein having the amino acid sequence of SEQ ID NO: 2. The phrase "a gene or protein has a nucleotide or amino acid sequence" can mean that a gene or protein includes the nucleotide or amino acid sequence as a part of a larger sequence unless otherwise stated, and can also mean that a gene or protein has only the nucleotide or amino acid sequence.

The production of a byproduct substance of 2-methyl-butyric acid by the bacterium that can be used in the method as described herein may be further reduced, as compared with a non-modified bacterium, by the attenuation of expression of one or more genes involved in L-leucine biosynthesis pathway which branches off from pyruvate in the biosynthesis pathway of 2-methyl-butyric acid. The first step in L-leucine biosynthesis pathway is the formation of 2-isopropylmalate from 2-keto-isovalerate, acetyl-CoA and $H_2O$, and it is catalyzed by 2-isopropylmalate synthase which is encoded by leuA gene. The second step is the conversion of 2-isopropylmalate to 3-isopropylmalate which is catalyzed by 3-isopropylmalate dehydratase which is encoded by the leuCD genes. The next reaction is the formation of 2-isopropyl-3-keto-succinate from 3-isopropylmalate, and it is catalyzed by 3-isopropylmalate dehydrogenase which is encoded by leuB gene. The synthesized 2-isopropyl-3-keto-succinate spontaneously turns to 2-keto-isocaproate which is a precursor of 3-methyl-butyric acid, a byproduct substance that is produced during the production of 2-methyl-butyric acid by fermentation of a 2-methyl-butyric acid-producing bacterium belonging to the order Enterobacterales.

By attenuating expression of one or more genes in the L-leucine biosynthesis pathway such as leuA, leuB, leuC, and/or leuD, one can impart to a bacterium that can be used in the method as described herein the property to produce one or more byproduct substance(s) in a lower amount as compared with the bacterium in which the leuA, leuB, leuC, and/or leuD gene(s) is/are not attenuated. As a result of attenuating the expression of said gene(s), the production of one or more byproduct substance(s) such as, for example, 3-methyl-butyric acid by the modified bacterium can be decreased further and 2-methyl-butyric acid can be produced at a higher purity.

The term "leuA gene" can mean a gene which encodes an enzyme having a 2-isopropylmalate synthase activity. A specific example of the gene which encodes the enzyme having the 2-isopropylmalate synthase activity includes the leuA gene which encodes 2-isopropylmalate synthase. The gene encoding the enzyme having the 2-isopropylmalate synthase activity can be the leuA gene and its homolog(s) or variant nucleotide sequence(s). The more specific description of leuA and its variant nucleotide sequences is given hereinafter.

The leuA gene encodes the 2-isopropylmalate synthase protein LeuA (KEGG, entry No. b0074; Protein Knowledgebase, UniProtKB/Swiss-Prot, accession No. P09151). The leuA gene (GenBank accession No. NC_000913.3; nucleotide positions: 81958 to 83529, complement; Gene ID: 947465) is located between the leuL and leuB genes on the same strand on the chromosome of $E.$ $coli$ strain K-12. The leuA gene is a part of the leuABCD operon. The nucleotide sequence of the leuA gene and the amino acid sequence of the LeuA protein encoded by the leuA gene are shown in SEQ ID NO: 3 and SEQ ID NO: 4, respectively.

The phrase "a 2-isopropylmalate synthase activity" can mean enzymatic activity of catalyzing the following reaction: 3-methyl-2-keto-butanoate+acetyl-CoA+$H_2O$→(2S)-2-isopropylmalate+coenzyme A+$H^+$ (EC: 2.3.3.13).

The term "leuB gene" can mean a gene which encodes an enzyme having a 3-isopropylmalate dehydrogenase activity. A specific example of the gene which encodes the enzyme having the 3-isopropylmalate dehydrogenase activity includes the leuB gene which encodes 3-isopropylmalate dehydrogenase. The gene encoding the enzyme having the 3-isopropylmalate dehydrogenase activity can be the leuB gene and its homolog(s) or variant nucleotide sequence(s). The more specific description of leuB and its variant nucleotide sequences is given hereinafter.

The leuB gene encodes the 3-isopropylmalate dehydrogenase protein LeuB (synonyms: IMDH, 3-carboxy-2-hydroxy-4-methylpentanoate:$NAD^+$ oxidoreductase; KEGG, entry No. b0073; Protein Knowledgebase, UniProtKB/Swiss-Prot, accession No. P30125). The leuB gene (GenBank accession No. NC_000913.3; nucleotide positions: 80867 to 81958, complement; Gene ID: 944798) is located between the leuA and leuC genes on the same strand on the chromosome of $E.$ $coli$ strain K-12. The leuB gene is a part of the leuABCD operon. The nucleotide sequence of the leuB gene and the amino acid sequence of the LeuB protein encoded by the leuB gene are shown in SEQ ID NO: 5 and SEQ ID NO: 6, respectively.

The phrase "a 3-isopropylmalate dehydrogenase activity" can mean enzymatic activity of catalyzing the following reaction: (2R,3S)-3-isopropylmalate+$NAD^+$→4-methyl-2-keto-pentanoate+$CO_2$ NADH (EC: 1.1.1.85).

The term "leuCD genes" can mean genes which encode an enzyme having a 3-isopropylmalate dehydratase activity. A specific example of the genes which encode the enzyme having the 3-isopropylmalate dehydratase activity includes the leuC and leuD genes which encode large and small subunits of 3-isopropylmalate dehydratase respectively. The genes encoding the enzyme having the 3-isopropylmalate dehydratase activity can be the leuC and leuD genes and their homologs or variant nucleotide sequences. The more specific description of leuC, leuD, and their variant nucleotide sequences is given hereinafter.

The leuC gene encodes the large subunit of 3-isopropylmalate dehydratase LeuC (KEGG, entry No. b0072; Protein Knowledgebase, UniProtKB/Swiss-Prot, accession No. P0A6A6). The leuC gene (GenBank accession No. NC_000913.3; nucleotide positions: 79464 to 80864, complement; Gene ID: 945076) is located between the leuB and leuD genes on the same strand on the chromosome of $E.$ $coli$ strain K-12. The leuC gene is a part of the leuABCD operon. The nucleotide sequence of the leuC gene and the amino acid sequence of the LeuC protein encoded by the leuC gene are shown in SEQ ID NO: 7 and SEQ ID NO: 8, respectively.

The leuD gene encodes the small subunit of 3-isopropylmalate dehydratase LeuD (KEGG, entry No. b0071; Protein Knowledgebase, UniProtKB/Swiss-Prot, accession No. P30126). The leuD gene (GenBank accession No. NC_000913.3; nucleotide positions: 78848 to 79453, complement; Gene ID: 945642) is located between the leuC gene on the same strand and the setA gene on the opposite strand on the chromosome of $E.$ $coli$ strain K-12. The leuD gene is a part of the leuABCD operon. The nucleotide sequence of the leuD gene and the amino acid sequence of the LeuD protein encoded by the leuD gene are shown in SEQ ID NO: 9 and SEQ ID NO: 10, respectively.

LeuC and LeuD constitute 3-isopropylmalate dehydratase LeuCD (synonym: 3-isopropylmalate isomerase).

The phrase "a 3-isopropylmalate dehydratase activity" can mean enzymatic activity of catalyzing the following reaction: (2R,3S)-3-isopropylmalate↔(2S)-2-isopropylmalate (EC: 4.2.1.33).

That is, the leuA, leuB, leuC, and leuD genes may be genes, such as DNA, having the nucleotide sequences of SEQ ID NOS: 3, 5, 7, and 9, respectively, and the LeuA, LeuB, LeuC, and LeuD proteins may be proteins having the amino acid sequence of SEQ ID NOS: 4, 6, 8, and 10, respectively.

The protein concentration can be determined by the Bradford protein assay or the method of Lowry using bovine serum albumin (BSA) as a standard and a Coomassie dye (Bradford M. M., A rapid and sensitive method for the quantitation of microgram quantities of protein utilizing the principle of protein-dye binding, *Anal. Biochem.*, 1976, 72:248-254; Lowry O. H. et al., Protein measurement with the Folin phenol reagent, *J. Biol. Chem.*, 1951, 193:265-275), or a Western blot analysis (Hirano S., Western blot analysis, *Methods Mol. Biol.*, 2012, 926:87-97).

The explanations given hereinafter with reference to, for example, gene expression attenuation, a variant protein and a variant nucleotide sequence can be applied with appropriate changes to any protein and gene described in this specification including, but is not limited to, TyrB, LeuA, LeuB, LeuC, LeuD, KdcA, and AldH proteins, and the genes encoding them such as tyrB, leuA, leuB, leuC, leuD, kdcA, and aldH genes, and homologs thereof.

The phrase "a bacterium has been modified to attenuate expression of a gene" can mean that the bacterium has been modified in such a way that in the modified bacterium expression of the gene is attenuated. For example, the expression of the gene can be attenuated due to inactivation of the gene.

The phrase "a gene is inactivated" can mean that the modified gene encodes a completely inactive or non-functional protein as compared with a wild-type or non-modified gene. It is also acceptable that the modified DNA region is unable to naturally express the gene due to deletion of a part of the gene or deletion of the entire gene, replacement of one base or more to cause an amino acid substitution in the protein encoded by the gene (missense mutation), introduction of a stop codon (nonsense mutation), deletion of one or two bases to cause a reading frame shift of the gene, insertion of a drug-resistance gene and/or transcription termination signal, or modification of an adjacent region of the gene, including sequences controlling gene expression such as promoter, enhancer, attenuator, ribosome-binding site, etc. Inactivation of the gene can also be performed, for example, by conventional methods such as a mutagenesis treatment using UV irradiation or nitrosoguanidine (N-methyl-N'-nitro-N-nitrosoguanidine), site-directed mutagenesis, gene disruption using homologous recombination, and/or insertion-deletion mutagenesis (Yu D. et al., An efficient recombination system for chromosome engineering in *Escherichia coli*, *Proc. Natl. Acad. Sci. USA*, 2000, 97(11):5978-5983; Datsenko K. A. and Wanner B. L., One-step inactivation of chromosomal genes in *Escherichia coli* K-12 using PCR products, *Proc. Natl. Acad. Sci. USA*, 2000, 97(12):6640-6645; Zhang Y. et al., A new logic for DNA engineering using recombination in *Escherichia coli*, *Nature Genet.*, 1998, 20:123-128) based on "Red/ET-driven integration" or "λRed/ET-mediated integration".

The phrase "a bacterium has been modified to attenuate expression of a gene" can mean that the modified bacterium contains a regulatory region operably linked to the gene, including sequences controlling gene expression such as promoters, enhancers, attenuators, and transcription termination signals, ribosome-binding sites, and other expression control elements, which is modified resulting in the decrease of the expression level of the gene; and other examples (see, for example, WO9534672 A1; Carrier T. A. and Keasling J. D., Library of synthetic 5' secondary structures to manipulate mRNA stability in *Escherichia coli*, *Biotechnol Prog.*, 1999, 15:58-64).

The phrase "operably linked to the gene" in reference to a regulatory region can mean that the regulatory region(s) is/are linked to the nucleotide sequence of the nucleic acid molecule or gene in such a manner which allows for expression, for example, enhanced, increased, constitutive, basal, antiterminated, attenuated, deregulated, decreased, or repressed expression, of the nucleotide sequence, specifically, the expression of a gene product encoded by the nucleotide sequence.

The phrase "a bacterium has been modified to attenuate expression of a gene" can also mean that the bacterium has been modified in such a way that in the modified bacterium, the expression level (that is, expression amount) of a gene is decreased as compared with a non-modified strain, for example, a wild-type or parental strain. A decrease in the expression level of a gene can be measured as, for example, a decrease in the expression level of the gene per cell, which may be an average expression level of the gene per cell. The phrase "the expression level of a gene" or "the expression amount of a gene" can mean, for example, that the amount of the expression product of the gene, such as the amount of mRNA of the gene or the amount of the protein encoded by the gene. The bacterium may be modified so that the expression level of the gene per cell is reduced to, for example, 50% or less, 20% or less, 10% or less, 5% or less, or 0% of that in a non-modified bacterium.

The phrase "a bacterium has been modified to attenuate expression of a gene" can also mean that the bacterium has been modified in such a way that in the modified bacterium the total amount and/or the total activity of the corresponding gene product (i.e. the encoded protein) is decreased as compared with a non-modified bacterium. A decrease in the total amount and/or the total activity of a protein can be measured as, for example, a decrease in the amount or activity of the protein per cell, which may be an average amount or activity of the protein per cell. The bacterium can be modified so that the activity of the protein per cell is decreased to, for example, 50% or less, 20% or less, 10% or less, 5% or less, or 0% of that in a non-modified bacterium.

Examples of a non-modified bacterium serving as a reference for the above comparisons can include wild-type strains of a bacterium belonging to the genus *Escherichia*, such as the *E. coli* MG1655 strain (ATCC 47076), *E. coli* W3110 strain (ATCC 27325), or a bacterium belonging to the genus *Pantoea*, such as the *P. ananatis* AJ13355 strain (FERM BP-6614), and so forth. Examples of a non-modified bacterium serving as a reference for the above comparisons can also include a parental strain which has not been modified to attenuate expression of the gene or a bacterium in which expression of the gene is not attenuated.

Expression of a gene can be attenuated by replacing an expression control sequence of the gene, such as a promoter on the chromosomal DNA, with a weaker one. The strength of a promoter is defined by the frequency of initiation acts of RNA synthesis. Examples of methods for evaluating the strength of promoters are described in Goldstein M. A. et al. (Goldstein M. A. and Doi R. H., Prokaryotic promoters in biotechnology, *Biotechnol. Annu. Rev.*, 1995, 1:105-128), and so forth. Furthermore, it is also possible to introduce one or more nucleotide substitutions in a promoter region of the gene and thereby modify the promoter to be weakened as disclosed in WO0018935 A1. Furthermore, it is known that substitution of several nucleotides in the Shine-Dalgarno (SD) sequence, and/or in the spacer between the SD sequence and the start codon, and/or a sequence immediately upstream and/or downstream from the start codon in the ribosome-binding site (RBS) greatly affects the translation efficiency of mRNA. This modification of the RBS may be combined with decreasing transcription of the gene.

Expression of a gene can also be attenuated by inserting a transposon or an insertion sequence (IS) into the coding region of the gene (U.S. Pat. No. 5,175,107) or in the region controlling gene expression, or by conventional methods such as mutagenesis with ultraviolet (UV) irradiation or nitrosoguanidine (N-methyl-N'-nitro-N-nitrosoguanidine, NTG). Furthermore, the incorporation of a site-specific mutation can be conducted by known chromosomal editing methods based, for example, on λRed/ET-mediated recombination (Datsenko K. A. and Wanner B. L., *Proc. Natl. Acad. Sci. USA*, 2000, 97(12):6640-6645).

The copy number and/or the presence or absence of the gene can be measured, for example, by restricting the chromosomal DNA followed by Southern blotting using a probe based on the gene sequence, fluorescence in situ hybridization (FISH), and the like. The level of gene expression can be determined by measuring the amount of mRNA transcribed from the gene using various well-known methods, including Northern blotting, quantitative RT-PCR, and the like. The amount of the protein encoded by the gene can be measured by known methods including SDS-PAGE followed by immunoblotting assay (Western blotting analysis), or mass spectrometry analysis of the protein samples, and the like.

Methods for manipulation with recombinant molecules of DNA and molecular cloning such as preparation of plasmid DNA, digestion, ligation, and transformation of DNA, selection of an oligonucleotide as a primer, incorporation of mutations, and the like may be ordinary methods well-known to the persons of ordinary skill in the art. These methods are described, for example, in Sambrook J., Fritsch E. F. and Maniatis T., "Molecular Cloning: A Laboratory Manual", $2^{nd}$ ed., Cold Spring Harbor Laboratory Press (1989) or Green M. R. and Sambrook J. R., "Molecular Cloning: A Laboratory Manual", $4^{th}$ ed., Cold Spring Harbor Laboratory Press (2012); Bernard R. Glick, Jack J. Pasternak and Cheryl L. Patten, "Molecular Biotechnology: principles and applications of recombinant DNA", $4^{th}$ ed., Washington, DC, ASM Press (2009).

Any methods for manipulation with recombinant DNA can be used including conventional methods such as, for example, transformation, transfection, infection, conjugation, and mobilization. Transformation, transfection, infection, conjugation, or mobilization of a bacterium with the DNA encoding a protein can impart to the bacterium the ability to synthesize the protein encoded by the DNA. Methods of transformation, transfection, infection, conjugation, and mobilization include any known methods. For example, a method of treating recipient cells with calcium chloride to increase permeability of the cells of *E. coli* K-12 to DNA has been reported for efficient DNA transformation and transfection (Mandel M. and Higa A., Calcium-dependent bacteriophage DNA infection, *J. Mol. Biol.,* 1970, 53:159-162). Methods of specialized and/or generalized transduction were described (Morse M. L. et al., Transduction in *Escherichia coli* K-12, *Genetics,* 1956, 41(1):142-156; Miller J. H., *Experiments in Molecular Genetics.* Cold Spring Harbor, N.Y.: Cold Spring Harbor La. Press, 1972). Other methods for random and/or targeted integration of DNA into the host microorganism can be applied, for example, "Mu-driven integration/amplification" (Akhverdyan et al., *Appl. Microbiol. Biotechnol.,* 2011, 91:857-871), "Red/ET-driven integration" or "λRed/ET-mediated integration" (Datsenko K. A. and Wanner B. L., *Proc. Natl. Acad. Sci. USA* 2000, 97(12):6640-45; Zhang Y., et al., *Nature Genet.,* 1998, 20:123-128). Moreover, for multiple insertions of desired genes in addition to Mu-driven replicative transposition (Akhverdyan et al., *Appl. Microbiol. Biotechnol.,* 2011, 91:857-871) and chemically inducible chromosomal evolution based on recA-dependent homologous recombination resulted in an amplification of desired genes (Tyo K. E. J. et al., *Nature Biotechnol.,* 2009, 27:760-765), and other methods can be used, which utilize different combinations of transposition, site-specific, and/or homologous Red/ET-mediated recombinations, and/or P1-mediated generalized transduction (see, for example, Minaeva N. et al., *BMC Biotechnology,* 2008, 8:63; Koma D. et al., *Appl. Microbiol. Biotechnol.,* 2012, 93(2):815-829).

There may be some differences in DNA sequences between the families, genera, species, or strains belonging to the order Enterobacterales. Therefore, the tyrB, leuA, leuB, leuC, and leuD genes are not limited to the genes having the nucleotide sequences shown in SEQ ID NOS: 1, 3, 5, 7, and 9, accordingly, but may include genes having variant nucleotide sequences of or homologous to SEQ ID NOs: 1, 3, 5, 7, and 9, accordingly, and which encode variants of the TyrB, LeuA, LeuB, LeuC, and LeuD proteins. Similarly, the TyrB, LeuA, LeuB, LeuC, and LeuD proteins are not limited to the proteins having the amino acid sequences shown in SEQ ID NOS: 4, 6, 8, and 10, but may include proteins having variant amino acid sequences of or homologous to SEQ ID NO: 4, 6, 8, and 10.

The phrase "a variant protein" can mean a protein having a variant amino acid sequence.

The phrase "a variant protein" can mean a protein which has one or more mutations in the amino acid sequence as compared with the wild-type amino acid sequence of the protein whether they are substitutions, deletions, insertions, and/or additions of one or several amino acid residues, but still maintains an activity or function similar to that of the wild-type protein, or the three-dimensional structure of the variant proteins is not significantly changed relative to the wild-type or non-modified protein. The number of changes in a variant protein depends on the position of amino acid residues in the three-dimensional structure of the protein or the type of amino acid residues. It can be, but is not strictly limited to, 1 to 150, in another example 1 to 100, in another example 1 to 50, in another example 1 to 30, in another example 1 to 15, in another example 1 to 10, and in another example 1 to 5, in the wild-type amino acid sequence of the protein. This is because some amino acids have high homology to one another so that the activity or function is not affected by such a change, or the three-dimensional structure of the protein is not significantly changed relative to the wild-type or non-modified protein. Therefore, the variant protein may be a protein having an amino acid sequence having a homology, defined as the parameter "identity" when using the computer program blastp, of not less than 60%, of not less than 65%, not less than 70%, not less than 75%, not less than 80%, not less than 85%, not less than 90%, not less than 95%, not less than 98%, or not less than 99% with respect to the entire wild-type amino acid sequence of the protein, as long as the activity or function of the protein is maintained, or the three-dimensional structure of the protein is not significantly changed relative to the wild-type or non-modified protein. In this specification, "homology" may mean "identity", that is the identity of amino acid residues. The sequence identity between two sequences is calculated as the ratio of residues matching in the two sequences when aligning the two sequences to achieve a maximum alignment with each other.

The exemplary substitution, deletion, insertion, and/or addition of one or several amino acid residues can be a conservative mutation(s), so that the activity and features of the variant protein are maintained, or the three-dimensional structure of the protein is not significantly changed relative to the non-modified protein such as, for example, the wild-type protein. The representative conservative mutation is a conservative substitution. The conservative substitution can be, but is not limited to, a substitution, wherein substitution takes place mutually among Phe, Trp, and Tyr, if the substitution site is an aromatic amino acid; among Ala, Leu, Ile, and Val, if the substitution site is a hydrophobic amino acid; between Glu, Asp, Gln, Asn, Ser, His, and Thr, if the substitution site is a hydrophilic amino acid; between Gln and Asn, if the substitution site is a polar amino acid; among Lys, Arg, and His, if the substitution site is a basic amino acid; between Asp and Glu, if the substitution site is an acidic amino acid; and between Ser and Thr, if the substitution site is an amino acid having hydroxyl group. Examples of conservative substitutions include substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp or Arg for Gln, substitution of Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val.

The exemplary substitution, deletion, insertion, and/or addition of one or several amino acid residues can also be a non-conservative mutation(s) provided that the mutation(s) is/are compensated by one or more secondary mutations in the different position(s) of amino acids sequence so that the activity or function of the variant protein is maintained, or the three-dimensional structure of the protein is not significantly changed relative to the non-modified protein such as, for example, the wild-type protein.

The calculation of a percent identity of an amino acid sequence can be carried out using the algorithm blastp. More specifically, the calculation of a percent identity of an amino acid sequence can be carried out using the algorithm blastp in the default settings of Scoring Parameters (Matrix: BLOSUM62; Gap Costs: Existence=11 Extension=1; Compositional Adjustments: Conditional compositional score matrix adjustment) provided by National Center for Biotechnology Information (NCBI). The calculation of a percent identity of a nucleotide sequence can be carried out using the algorithm blastn. More specifically, the calculation of a percent identity of a nucleotide sequence can be carried out using the algorithm blastn in the default settings of Scoring Parameters (Match/Mismatch Scores=1,-2; Gap Costs=Linear) provided by NCBI.

The protein homologues of TyrB native to different bacteria belonging to the order Enterobacterales are known that have the tyrosine aminotransferase activity as described above. Examples of such homologous proteins that are native to the bacteria belonging to the order Enterobacterales are described in Table 1 with accession numbers of amino acid sequences in the NCBI database (National Center for Biotechnology Information, ncbi.nlm.nih.gov/protein/), taxonomy data, and indication of a homology value (as "identity", that is the identity of amino acids).

TABLE 1

Protein homologues of TyrB.

| Accession No.* | Organism | Identity** |
|---|---|---|
| WP_000486985.1 | Escherichia coli K-12 MG1655 | 100% |
| WP_128875460.1 | Shigella dysenteriae | 99% |
| WP_044709161.1 | Escherichia albertii | 94% |
| WP_112001357.1 | Citrobacter koseri | 93% |
| EAA9367477.1 | Salmonella enterica | 92% |
| WP_063941226.1 | Enterobacter cloacae | 91% |
| WP_047045861.1 | Klebsiella aerogenes | 88% |
| WP_090136777.1 | Kosakonia oryziphila | 88% |
| WP_015742653.1 | Cronobacter turicensis | 87% |
| WP_103947500.1 | Lelliottia aquatilis | 87% |
| WP_034456957.1 | Buttiauxella noackiae | 87% |
| WP_045289609.1 | Pluralibacter gergoviae | 85% |
| WP_016517436.1 | Cedecea davisae | 85% |
| WP_067434221.1 | Erwinia gerundensis | 83% |
| WP_085069663.1 | Pantoea alhagi | 82% |
| ADD75434.1 | Pantoea ananatis LMG 20103 | 81% |
| WP_085982588.1 | Pantoea agglomerans | 80% |
| WP_061321992.1 | Serratia rubidaea | 79% |
| WP_050082921.1 | Yersinia frederiksenii | 78% |
| WP_022634786.1 | Dickeya solani | 77% |

TABLE 1-continued

Protein homologues of TyrB.

| Accession No.* | Organism | Identity** |
|---|---|---|
| WP_116155443.1 | Pectobactcrium aquaticum | 76% |
| WP_115459870.1 | Enterobacillus tribolii | 75% |
| WP_094100856.1 | Lonsdalea iberica | 74% |
| WP_038023955.1 | Tatumella morbirosei | 73% |
| WP_074023805.1 | Xenorhabdus eapokensis | 72% |
| SER25667.1 | Rosenbergiella nectarea | 71% |
| WP_046974208.1 | Photorhabdus thracensis | 70% |
| WP_015462403.1 | Edwardsiella piscicida | 69% |
| WP_093316479.1 | Thorsellia anophelis | 68% |
| WP_067400647.1 | Morganella psychrotolerans | 67% |
| WP_060556387.1 | Proteus mirabilis | 65% |
| WP_008913813.1 | Providencia burhodograneriea | 64% |
| WP_039855722.1 | Providencia rustigianii | 62% |

*in the NCBI database (National Center for Biotechnology Information, www.ncbi.nlm.nih.gov/)
**Identity was calculated with respect to the TyrB protein native to E. coli K-12 substr. MG1655 (GenBank: NP_418478.1, WP_000486985.1) using blastp and default settings provided by the NCBI database.

The phrase "a variant nucleotide sequence" can mean the nucleotide sequence which encodes a protein having the wild-type amino acid sequence using any synonymous amino acid codons according to the standard genetic code table (see, for example, Lewin B., "Genes VIII", 2004, Pearson Education, Inc., Upper Saddle River, NJ 07458). Therefore, a gene encoding a protein having the wild-type amino acid sequence can be a gene having a variant nucleotide sequence due to the degeneracy of the genetic code.

The phrase "a variant nucleotide sequence" can also mean, but is not limited to, a nucleotide sequence that is able to hybridize under stringent conditions with the nucleotide sequence complementary to the wild-type nucleotide sequence or a probe that can be prepared from the nucleotide sequence provided that it encodes a protein having tyrosine aminotransferase activity. "Stringent conditions" can include those under which a specific hybrid, for example, a hybrid having homology, defined as the parameter "identity" when using the computer program blastn, of not less than 60%, not less than 65%, not less than 70%, not less than 75%, not less than 80%, not less than 85%, not less than 90%, not less than 95%, not less than 96%, not less than 97%, not less than 98%, or not less than 99% is formed, and a non-specific hybrid, for example, a hybrid having homology lower than the above is not formed. For example, stringent conditions can be exemplified by washing one time or more, or in another example, two or three times, at a salt concentration of 1×SSC (standard sodium citrate or standard sodium chloride), 0.1% SDS (sodium dodecyl sulphate), or in another example, 0.1×SSC, 0.1% SDS at 60° C. or 65° C. Duration of washing depends on the type of membrane used for blotting and, as a rule, can be what is recommended by the manufacturer. For example, the recommended duration of washing for the Amersham Hybond™-N+ positively charged nylon membrane (GE Healthcare) under stringent conditions is 15 minutes. The washing step can be performed 2 to 3 times. As the probe, a part of the sequence complementary to the wild-type nucleotide sequence may also be used. Such a probe can be produced by PCR using oligonucleotides as primers prepared based on the wild-type nucleotide sequence and a DNA fragment containing the nucleotide sequence as a template. The length of the probe is recommended to be >50 bp; it can be suitably selected depending on the hybridization conditions, and is usually 100 bp to 1 kbp. For example, when a DNA fragment having a length of about 300 bp is used as the probe, the washing conditions after hybridization can be exemplified by 2×SSC, 0.1% SDS at 50° C., 60° C. or 65° C.

The phrase "a variant nucleotide sequence" can also mean a nucleotide sequence that encodes a variant protein.

As the gene encoding the wild-type protein native to the species *E. coli* has already been elucidated (see above), a variant nucleotide sequence encoding a variant protein of the wild-type protein can be obtained by PCR (polymerase chain reaction; refer to White T. J. et al., The polymerase chain reaction, *Trends Genet.*, 1989, 5(6):185-189) utilizing primers prepared based on the nucleotide sequence of the wild-type gene; or the site-directed mutagenesis method by treating a DNA containing a wild-type gene in vitro, for example, with hydroxylamine, or a method for treating a microorganism, for example, a bacterium belonging to the species *E. coli* harboring a wild-type gene with ultraviolet (UV) irradiation or a mutating agent such as N-methyl-N'-nitro-N-nitrosoguanidine (NTG) and nitrous acid usually used for the such treatment; or chemically synthesized as full-length gene structure. Genes encoding the proteins or its variant proteins from other bacteria belonging to the order Enterobacterales can be obtained in a similar manner.

The phrase "wild-type", which can be equivalent to the phrases "native" and "natural", as used herein as to a protein (for example, "a wild-type protein") and a gene (for example, "a wild-type gene") can mean, respectively, a native protein and a native gene that exist, and/or is expressed naturally in, and/or produced by a wild-type bacterium, for example, a wild-type strain of a bacterium belonging to the order Enterobacterales such as, for example, the family Enterobacteriaceae or Erwiniaceae such as, for example, the *E. coli* MG1655 strain (ATCC 47076), the *E. coli* W3110 strain (ATCC 27325), the *P. ananatis* AJ13355 strain (FERM BP-6614), and so forth. As a protein is encoded by a gene, "a wild-type protein" can be encoded by "a wild-type gene" naturally occurring in genome of a wild-type bacterium.

The phrase "a wild-type protein" can mean a native protein naturally produced by a wild-type or parent bacterial strain belonging to the order Enterobacterales, for example, by the wild-type *E. coli* MG1655 strain or *P. ananatis* AJ13355 strain. A wild-type protein can be encoded by the "wild-type gene", or the "non-modified gene" naturally occurring in genome of a wild-type bacterium. A wild-type protein and wild-type gene can have "a wild-type amino acid sequence" and "a wild-type nucleotide sequence", accordingly, as a primary structure of proteins and genes.

The phrase "native to" in reference to a protein or a nucleic acid native to a particular organism such as, for example, a bacterial species can refer to a protein or a nucleic acid that is native to that organism. That is, a protein or a nucleic acid native to a particular organism can mean the protein or the nucleic acid, respectively, that exists naturally in the organism and can be isolated from that organism and sequenced using means known to the one of ordinary skill in the art. Moreover, as the amino acid sequence or the nucleotide sequence of a protein or nucleic acid, respectively, isolated from an organism in which the protein or nucleic acid exists, can easy be determined, the phrase "native to" in reference to a protein or a nucleic acid can also refer to a protein or a nucleic acid that can be obtained using, for example, a genetic engineering technique, including recombinant DNA technology, or a chemical synthesis method, or the like, so long as the amino acid sequence of the protein or the nucleotide sequence of the nucleic acid thus obtained is identical, accordingly, to the amino acid sequence of the protein or the nucleotide sequence of the nucleic acid that exists naturally in the organism. Examples of amino acid sequences native to particular species include, but are not limited to, peptides, oligopeptides, polypeptides, including proteins, specifically enzymes, and so forth. Examples of nucleotide sequences native to particular species include deoxyribonucleic acid (DNA) and ribonucleic acid (RNA), and these are not limited to expression regulatory sequences, including promoters, attenuators, terminators, and the like, genes, intergenic sequences, and nucleotide sequences encoding signal peptides, pro-moieties of proteins, artificial amino acid sequences, and so forth. Specific examples of amino acid sequences and nucleotide sequences, and homologues thereof native to various species are described herein, and these examples include the proteins having the amino acid sequences shown in SEQ ID NOs: 2, 4, 6, 8, and 10, which are native to the bacterium of the species *E. coli* and can be encoded by the genes having the nucleotide sequences shown in SEQ ID NOs: 1, 3, 5, 7, and 9, accordingly.

The bacterium can have, in addition to the properties already mentioned, other specific properties such as various nutrient requirements, drug resistance, drug sensitivity, and drug dependence.

2. Method

The method as described herein includes a method of producing 2-methyl-butyric acid using a bacterium as described herein. The method of producing 2-methyl-butyric acid includes the steps of cultivating (also called "culturing") the bacterium in a culture medium to allow 2-methyl-butyric acid to be produced, excreted, and/or accumulated in the culture medium or in the bacterial cells, or both, and collecting 2-methyl-butyric acid from the culture medium and/or the bacterial cells. The method may further include, optionally, the step of purifying 2-methyl-butyric acid from the culture medium and/or the bacterial cells. 2-Methyl-butyric acid can be produced in a free form or as a salt thereof, or as a mixture of them. Hence, the phrase "2-Methyl-butyric acid" can mean, for example, 2-Methyl-butyric acid in a free form, a salt thereof, or a mixture of them. For example, sodium, potassium, ammonium, and the like salts of 2-methyl-butyric acid can be produced by the method. This is possible as carboxylic acids, to which 2-methyl-butyric acid belongs, can react under fermentation conditions with a neutralizing agent such as an inorganic or organic substance in a typical acid-base neutralization reaction to form a salt that is the chemical feature of carboxylic acids which is apparent to the person skilled in the art.

The cultivation of the bacterium, and collection and, optionally, purification of 2-methyl-butyric acid from the medium and the like may be performed in a manner similar to the conventional fermentation methods wherein an L-amino acid is produced using a microorganism. That is, the cultivation of the bacterium, and collection and purification of 2-methyl-butyric acid from the medium and the like may be performed by applying the conditions that are suitable for the cultivation of the bacterium, and appropriate for the collection and purification of an L-amino acid, which conditions are well-known to the persons of ordinary skill in the art.

The culture medium to be used is not particularly limited, so long as the medium contains, at least, a carbon source, and the bacterium as described herein can proliferate in it and produce 2-methyl-butyric acid. The culture medium can be either a synthetic or natural medium such as a typical medium that contains a carbon source, a nitrogen source, a sulphur source, a phosphorus source, inorganic ions, and other organic and inorganic components as required. As the carbon source, saccharides such as glucose, sucrose, lactose, galactose, fructose, arabinose, maltose, xylose, trehalose, ribose, and hydrolyzates of starches; alcohols such as ethanol, glycerol, mannitol, and sorbitol; organic acids such as gluconic acid, fumaric acid, citric acid, malic acid, and succinic acid; fatty acids, and the like can be used. As the nitrogen source, inorganic ammonium salts such as ammonium sulfate, ammonium chloride, and ammonium phosphate; organic nitrogen such as of soy bean hydrolysate; ammonia gas; aqueous ammonia; and the like can be used. Furthermore, peptone, yeast extract, meat extract, malt extract, corn steep liquor, and so forth can also be utilized. The medium may contain one or more types of these nitrogen sources. The sulphur source can include ammonium sulphate, magnesium sulphate, ferrous sulphate, manganese sulphate, and the like. The medium can contain a phosphorus source in addition to the carbon source, the nitrogen source and the sulphur source. As the phosphorus source, potassium dihydrogen phosphate, dipotassium hydrogen phosphate, phosphate polymers such as pyrophosphoric acid and so forth can be utilized. Vitamins such as vitamin B1, vitamin B2, vitamin B6, nicotinic acid, nicotinamide, vitamin B12, required substances, for example, organic nutrients such as nucleic acids such as adenine and RNA, amino acids, peptone, casamino acid, yeast extract, and the like may be present in appropriate, even if trace, amounts. Other than these, small amounts of calcium phosphate, iron ions, manganese ions, and so forth may be added, if necessary.

Cultivation can be performed under the conditions suitable for cultivating a bacterium chosen for the use in the method for producing 2-methyl-butyric acid. For example, the cultivation can be performed under aerobic conditions for from 16 to 72 hours or for from 16 to 65 hours, the culture temperature during cultivation can be controlled within from 30 to 45° C. or within from 30 to 37° C., and the pH can be adjusted between 5 and 8 or between 6.0 and 7.5. The pH can be adjusted using an inorganic or organic acidic or alkaline substance such as urea, calcium carbonate or ammonia gas.

After cultivation, 2-methyl-butyric acid can be collected from the culture medium. Specifically, 2-methyl-butyric acid present outside of cells can be collected from the culture medium. Also, after cultivation, 2-methyl-butyric acid can be collected from cells of the bacterium. Specifically, the cells can be disrupted, a supernatant can be obtained by removing solids such as the cells and the cell-disrupted suspension (so-called cell debris), and then 2-methyl-butyric acid can be collected from the supernatant. Disruption of the cells can be performed using, for example, methods that are well-known in the art, for example, ultrasonic lysis using high frequency sound waves, or the like. Removal of solids can be performed by, for example, centrifugation or membrane filtration. Collection of 2-methyl-butyric acid from the culture medium or the supernatant etc. can be performed using, for example, conventional techniques such as, for example, concentration, crystallization, membrane treatment, ion-exchange chromatography, flash chromatography, thin-layer chromatography, medium or high pressure liquid chromatography. These methods may be independently used, or may be used in an appropriate combination.

EXAMPLES

The present invention will be more precisely explained below with reference to the following non-limiting examples.

Example 1

Construction of E. coli Strain L1190-1

A 2-methyl-butyric acid-producing strain was constructed from an L-isoleucine-producing E. coli strain NS1547. The NS1547 strain had the MG1655 Δtdh rhtA*mini-Mu::$P_{lac}$-lacI-ilvA*$P_L$-SD1-ilvG*MEDA genotype.

The strain NS1547 has a mutation in the rhtA gene (rhtA23) (US20010049126 A1) that confers the resistance to high concentration of threonine (>40 mg/mL) or homoserine (>5 mg/mL) and improves threonine production, and the deletion of the tdh gene (SEQ ID NO: 11) (Shakalis I. O. and Gusyatiner M. M., Participation of threonine dehydrogenase, threonine desaminase and serine transhydroxymethylase in threonine degradation in *Escherichia coli* cells K-12, *Biotekhnologiya*, 1990, (2):16-17) that prevents threonine degradation. The strain NS1547 also contains the expression cassette mini-Mu: $P_{lac}$-lacI-ilvA*-kan (SEQ ID NO: 12) (Sycheva E. V. et al., Aerobic catabolism of threonine in *Escherichia coli* strain with feedback resistant biosynthetic threonine deaminase, *Biotekhnologiya*, 2003, (4):22-34), which includes the mutant ilvA gene encoding feedback-resistant threonine deaminase and the lacI repressor gene under the control of $P_{lac}$ promoter. This cassette allows the IPTG-inducible expression of threonine deaminase, which carries out the first step in isoleucine biosynthesis pathway such as the conversion of threonine into 2-ketobutyrate. To ensure a sufficient 2-keto-3-methyl-valerate supply for 2-methyl-butyric acid production, the strain NS1547 possesses the expression cassette $P_L$-SD1-ilvG*MEDA (SEQ ID NO: 13) which provides the expression of ilvG*MEDA operon under control of the lambda phage $P_L$ promoter operably linked to the modified Shine-Dalgarno sequence named as SD1 (SD sequence from pET22b(+) plasmid (Novagen). This artificial operon (ilvG*MEDA) also contains the mutant ilvG gene (ilvG*) having the insertion of two base pairs (aa) between the nucleotides in position numbers 981 and 982 from the start-codon of the gene, upstream of the sequence TGACTGGCA (EP1627884 B1) restoring the frame-shift in the wild-type ilvG gene that provides the expression of feedback-resistant acetolactate synthase II.

The cassette dacA::mini-Mu::cat-$P_{thr}$-attB-thrA*BC (SEQ ID NO: 14) that provides the expression of the threonine operon from which a region required for attenuation is removed, was introduced into the strain NS1547 by P1-transduction (Sambrook J. et al., "Molecular Cloning A Laboratory Manual, 2nd Edition", Cold Spring Harbor Laboratory Press (1989)). The threonine operon contains a mutation in thrA gene (thrA442) (Akhverdyan V. Z. et al., Development of the mini-Mu system providing effective integration and amplification of the genetic material into the *Escherichia coli* chromosome, *Biotekhnologiya*, 2007, (3): 3-20), which confers aspartokinase I-homoserine dehydrogenase I insensitivity to feedback inhibition by threonine. This cassette is localized in the E. coli dacA gene and it is flanked by the phage mini-Mu L/R-ends for mini-Mu-mediated transposition (Akhverdyan V. Z. et al., Application of the bacteriophage Mu-driven system for the integration/amplification of target genes in the chromosomes of engineered Gram-negative bacteria—mini review, *Appl. Microbiol. Biotechnol.*, 2011, 91(4):857-871), with the chloramphenicol resistance ($Cm^R$) marker inserted into the Mu-attL end.

$Cm^R$ transductants were selected on the plates containing LB-medium (also referred to as Luria-Bertani medium as described in Sambrook, J. and Russell, D. W. "Molecular Cloning: A Laboratory Manual", 3$^{rd}$ ed., Cold Spring Harbor Laboratory Press (2001)), agar (1.5%) and Cm (20 mg/L) and verified by PCR using primers P1 (SEQ ID NO: 15) and P2 (SEQ ID NO: 16). Conditions for PCR verification were as follows: denaturation step for 5 min at 94° C.; profile for the 25 cycles: 30 sec at 94° C., 30 sec at 57° C., 1 min at 72° C.; final elongation for 7 min at 72° C. DNA fragment 1 (SEQ ID NO: 17), obtained in the reaction with DNA of the cells of the parental strain NS1547 as a template, was 1256 bp in length. DNA fragment 2 (SEQ ID NO: 18), obtained in the reaction with DNA of the cells of the strain NS1547 dacA::mini-Mu::cat-P$_{thr}$-attB-thrA*BC as a template, was 2452 bp in length. After that, λ-Int/Xis-mediated excision of the Cm$^R$-marker from the strain NS1547 dacA::mini-Mu:: cat-P$_{thr}$attB-thrA*BC was performed. As a result, the strain L1178-1 was obtained. Excision was confirmed by PCR as described above. DNA fragment 2 (SEQ ID NO: 18), obtained in the reaction with DNA of the cells of the parental strain NS1547 dacA::mini-Mu::cat-P$_{thr}$attB-thrA*BC as a template, was 2452 bp in length. DNA fragment 3 (SEQ ID NO: 19), obtained in the reaction with DNA of the cells of the strain L1178-1 as a template, was 842 bp in length.

The expression cassette ΔcynX::cat-P$_L$-ilvA* (SEQ ID NO: 20) was introduced into the strain L1178-1 by P1-transduction. This cassette is localized in the *E. coli* cynX gene and includes the mutant ilvA* gene (iivA$_{1237}$) having the replacement of g with a at position number 1237 from the start-codon of the gene that results in replacement of Glu$^{412}$ with Lys (Hashiguchi K. et al., Construction of an L-isoleucine overproducing strain of *Escherichia coli* K-12, *Biosci. Biotechnol. Biochem.*, 1999, 63(4):672-679), encoding feedback resistant threonine deaminase, under control of the lambda phage P$_L$ promoter.

Cm$^R$ transductants were selected and verified by PCR using primers P3 (SEQ ID NO: 21) and P4 (SEQ ID NO: 22). Conditions for PCR verification were as follows: denaturation for 5 min at 94° C.; profile for 25 cycles: 30 sec at 94° C., 30 sec at 59° C., 1 min at 72° C.; final elongation for 7 min at 72° C. There was no DNA fragment in the reaction with DNA of the cells of the parent strain L1178-1 used as a template. DNA fragment 4 (SEQ ID NO: 23), obtained in the reaction with DNA of the cells of the strain L1178-1 ΔcynX:cat-P$_L$-ilvA* as a template, was 2131 bp in length. After that, λ-Int/Xis-mediated excision of Cm$^R$-marker from the strain L1178-1 ΔcynX::cat-P$_L$-ilvA* was performed. As a result, the strain L1190-1 was obtained. Excision was confirmed by PCR as described above. DNA fragment 4 (SEQ ID NO: 23), obtained in the reaction with DNA of the cells of the parent strain L1178-1 ΔcynX:cat-P$_L$-ilvA* used as a template, was 2131 bp in length. DNA fragment 5 (SEQ ID NO: 24), obtained in the reaction with DNA of the cells of the strain L1190-1 as a template, was 534 bp in length.

Example 2

Constuction of *E. coli* Strain L1194-2

To provide 2-methyl-butyric acid biosynthesis, 2-methylbutyric acid biosynthesis genes were inserted into the chromosome of the strain L1190-1 (Example 1). The plasmid pAH162-tetA-tetR-kdcA-aldH was used which contains the heterologous kdcA gene native to *Lactococcus lactis* having codons optimized for the expression in *E. coli* (Savrasova E. A. et al., Use of the valine biosynthetic pathway to convert glucose into isobutanol, *J. Ind. Microbiol. Biotechnol.*, 2011, 38(9):1287-1294) and the aldH gene native to *E. coli*. The promoter-less 3195 bp DNA fragment of kdcA-aldH (SEQ ID NO: 25) was inserted into the integrative vector pAH162-λaaL-Tc$^R$-λattR (Minaeva N. I. et al., Dual-In/Out strategy for genes integration into bacterial chromosome: a novel approach to step-by-step construction of plasmid-less marker-less recombinant *E. coli* strains with predesigned genome structure, *BMC Biotechnol.*, 2008, 8:63) digested with MlsI/Sa/I The transformants of the *E. coli* CC118 λpir$^+$ strain (Herrero M. et al., Transposon vectors containing non-antibiotic resistance selection markers for cloning and stable chromosomal insertion of foreign genes in gram-negative bacteria, *J. Bacteriol.*, 1990, 172:6557-6567) carrying the recombinant plasmid pAH162-tetA-tetR-kdcA-aldH, were selected on the medium supplemented with tetracycline (Tc). The correct insertion was confirmed by restriction analysis and PCR analysis using primers P5 (SEQ ID NO: 26) and P6 (SEQ ID NO: 27), P7 (SEQ ID NO: 28) and P8 (SEQ ID NO: 29). Conditions for PCR verification were as follows: denaturation for 5 min at 94° C.; profile for 25 cycles: 30 sec at 94° C., 30 sec at 61° C., 1 min at 72° C.; final elongation for 7 min at 72° C. There was no DNA fragment in the reaction with DNA of the cells of the parent CC118 λpir$^+$ strain used as a template. DNA fragment 6 (SEQ ID NO: 30), obtained in the reaction with DNA of the cells of CC118 λpir$^+$ pAH162-tetA-tetR-kdcA-aldH strain as a template and primers P5 (SEQ ID NO: 26) and P6 (SEQ ID NO: 27), was 1045 bp in length. DNA fragment 7 (SEQ ID NO: 31), obtained in the reaction with DNA of the cells of CC118 λpir$^+$ pAH162-tetA-tetR-kdcA-aldH strain as a template and primers P7 (SEQ ID NO: 28) and P8 (SEQ ID NO: 29), was 865 bp in length.

Then, the plasmid pAH162-tetA-tetR-kdcA-aldH was integrated into the artificial locus trs5-10::φ80-attB of the *E. coli* strain MG1655 Δ(φ80-attB) trs5-10::φ80-attB (Minaeva N. I. et al., Dual-In/Out strategy for genes integration into bacterial chromosome: a novel approach to step-by-step construction of plasmid-less marker-less recombinant *E. coli* strains with predesigned genome structure, *BMC Biotechnol.*, 2008, 8:63) containing the plasmid pAH123 by φ80-driven integration. The cells of the strain MG1655 Δ(φ80-attB), that harbor trs5-10::pAH162-tetA-tetR-kdcA-aldH cassette, were selected on the plates containing LB-medium, agar (1.5%) and Tc (40 mg/L). The correct integration was confirmed by PCR using primers P9 (SEQ ID NO: 32) and P10 (SEQ ID NO: 33). Conditions for PCR verification were as follows: denaturation for 5 min at 94° C.; profile for 25 cycles: 30 sec at 94° C., 30 sec at 57° C., 1 min at 72° C.; final elongation for 7 min at 72° C. There was no DNA fragment in the reaction with DNA of the cells of the parent strain MG1655 Δ(φ80-attB) trs5-10::φ80-attB used as a template. DNA fragment 8 (SEQ ID NO: 34), obtained in the reaction with DNA of the cells of the strain MG1655 Δ(φ80-attB) trs5-10::pAH162-tetA-tetR-kdcA-aldH as a template, was 1629 bp in length. After λ-Int/Xis-mediated excision of the vector part of integrated plasmid, the strain MG1655 Δ(φ80-attB) trs5-10::kdcA-aldH was obtained. Excision of Tc$^R$-marker was confirmed by PCR using primers P9 (SEQ ID NO: 32) and P11 (SEQ ID NO: 35). Conditions for PCR verification were as follows: denaturation for 5 min at 94° C.; profile for 25 cycles: 30 sec at 94° C., 30 sec at 57° C., 1 min at 72° C.; final elongation for 7 min at 72° C. DNA fragment 9 (SEQ ID NO: 36), obtained in the reaction with DNA of the cells of the strain MG1655 Δ(φ80-attB) trs5-10::pAH162-tetA-tetR-kdcA-aldH as a template, was 4603 bp in length. DNA fragment 10 (SEQ ID NO: 37), obtained in the reaction with DNA of the cells of the strain MG1655 Δ(φ80-attB) trs5-10::kdcA-aldH as a template, was 1312 bp in length.

Then, to ensure a high level of constitutive expression, the regulatory region of the $P_{tac}$ promoter (De Boer H. A. et al., The tac promoter: a functional hybrid derived from the trp and lac promoters, *Proc. Natl. Acad. Sci. USA*, 1983, 80(1): 21-25) containing a half part of lac repressor binding site (FIG. 2), marked with the cat gene, was introduced upstream to the kdcA-aldH operon by the method developed by Datsenko and Wanner (Datsenko K. A. and Wanner B. L., *Proc. Natl. Acad. Sci. USA*, 2000, 97(12):6640-6645) called "λRed-dependent integration". According to this procedure, the PCR primers P12 (SEQ ID NO: 38) and P13 (SEQ ID NO: 39), which are homologous to both the region adjacent to the kdcA gene and the region adjacent to the cat gene and the $P_{tac}$ promoter in the template chromosome, were constructed. The chromosome of the *E. coli* strain MG1655 cat-$P_{tac}$-lacZ (Katashkina J. I. et al., Tuning of expression level of the genes of interest located in the bacterial chromosome, *Mol. Biol.* (Mosk.), 2005, 39(5):719-726) was used as a template in PCR reaction. Conditions for PCR were as follows: denaturation for 3 min at 95° C.; profile for two first cycles: 1 min at 95° C., 30 sec at 34° C., 80 sec at 72° C.; profile for the last 28 cycles: 30 sec at 95° C., 30 sec at 50° C., 80 sec at 72° C.; final step: 5 min at 72° C. The resulting 1768 bp DNA fragment 11 (SEQ ID NO: 40) was purified by "Silica Bead DNA Gel Extraction Kit" (Thermo Scientific) and used for electroporation of the strain MG1655 Δ(φ80-attB) trs5-10::kdcA-aldH containing the plasmid pKD46. The plasmid pKD46 (Datsenko K. A. and Wanner B. L., *Proc. Natl. Acad. Sci. USA*, 2000, 97(12): 6640-6645) includes a 2154 bp (position numbers from 31088 to 33241) DNA fragment of phage λ (GenBank, accession No. J02459) and contains genes of the λRed homologous recombination system ((gamma, beta, exo genes) under the control of arabinose-inducible $P_{araB}$ promoter. The plasmid pKD46 is necessary to integrate the DNA fragment into the bacterial chromosome.

Electrocompetent cells were prepared as follows: the strain MG1655 Δ(φ80-attB) trs5-10::kdcA-aldH, containing pKD46 plasmid, was grown overnight at 30° C. in LB medium containing ampicillin (100 mg/L), and the culture was diluted in 100 times with 5 mL of SOB medium (Sambrook J. et al., "Molecular Cloning: A Laboratory Manual", $2^{nd}$ ed., Cold Spring Harbor Laboratory Press (1989)) with ampicillin (100 mg/L) and L-arabinose (1 mM). The cells were grown with aeration (250 rpm) at 30° C. to an $OD_{600}$ of about 0.6 and then made electrocompetent by concentrating 100-fold and washing three times with ice-cold deionized $H_2O$. Electroporation was performed using 200 mkL of cells and about 100 ng of DNA fragment 11 (SEQ ID NO: 40). Then, cells were incubated with 1 mL of SOC medium (Sambrook J. et al., "Molecular Cloning: A Laboratory Manual", $2^{nd}$ ed., Cold Spring Harbor Laboratory Press (1989)) at 37° C. for 2.5 h, placed onto the plates containing LB-medium, agar (1.5%) and chloramphenicol (20 μg/mL), and grown at 37° C. to select chloramphenicol resistant recombinants. Then, to eliminate pKD46 plasmid, one passage on L-agar with Cm (20 μg/mL) at 42° C. was performed, and the obtained individual colonies were tested for sensitivity to ampicillin. Thus, the strain MG1655 Δ(φ80-attB) trs5-10::cat-Ptac-kdcA-aldH was selected. The introduction of $P_{tac}$ promoter was confirmed by PCR using primers P14 (SEQ ID NO: 41) and P6 (SEQ ID NO: 27). Conditions for PCR were as follows: denaturation for 5 at 94° C.; profile for 25 cycles: 30 sec at 94° C., 30 sec at 59° C., 1 min at 72° C.; final elongation for 7 min at 72° C. There was no DNA fragment in the reaction with DNA of the cells of the parent strain MG1655 Δ(φ80-attB) trs5-10::kdcA-aldH used as a template. DNA fragment 12 (SEQ ID NO: 42), obtained in the reaction with DNA of the cells of the strain MG1655 Δ(φ80-attB) trs5-10::cat-$P_{tac}$-kdcA-aldH as a template, was 1030 bp in length.

At the last step, the expression cassette trs5-10::cat-$P_{tac}$-kdcA-aldH was introduced into the chromosome of the strain L1190-1 (Example 1) by P1-transduction. The cells of the strain L1190-1, that harbor trs5-10::cat-Ptac-kdcA-aldH cassette, were selected on the plates containing LB-medium, agar (1.5%) and Cm (20 mg/L). Introduction of the trs5-10::cat-$P_{tac}$-kdcA-aldH cassette was verified by PCR as described above. After λ-Int/Xis-mediated excision of $Cm^R$-marker, the strain L1194-2 was obtained. Excision was confirmed by PCR using primers P15 (SEQ ID NO: 43) and P11 (SEQ ID NO: 35). DNA fragment 13 (SEQ ID NO: 44), obtained in the reaction with DNA of the cells of the parent strain L1190-1 trs5-10::cat-$P_{tac}$-kdcA-aldH used as a template, was 2777 bp in length. DNA fragment 14 (SEQ ID NO: 45), obtained in the reaction with DNA of the cells of the strain L1194-2 as a template, was 1167 bp in length.

Example 3

Construction of an *E. coli* 2-Methyl-Butyric Acid-Producing Strain L1201-1

The expression cassette $P_L$-ilvG*M-ΔilvE::cat-DA was introduced into the strain L1194-2 (Example 2). The MG1655 strain having modification $P_L$-ilvG*M-ΔilvE::cat-DA was constructed by the method of Red-dependent integration described above. According to this procedure, the PCR primers P16 (SEQ ID NO: 46) and P17 (SEQ ID NO: 47) homologous to both the region adjacent to the ilvE gene and the gene conferring chloramphenicol resistance in the template plasmid, were constructed. The plasmid pMW118-attL-cat-attR (Katashkina J. I. et al., Tuning of expression level of the genes of interest located in the bacterial chromosome, *Mol. Biol.* (Mosk), 2005, 39(5):719-726) was used as a template in the PCR reaction. Conditions for PCR were as follows: denaturation for 3 min at 95° C.; profile for two first cycles: 1 min at 95° C., 30 sec at 34° C., 80 sec at 72° C.; profile for the last 28 cycles: 30 sec at 95° C., 30 sec at 50° C., 80 sec at 72° C.; final elongation for 5 min at 72° C. The obtained DNA fragment 15 (1713 bp) (SEQ ID NO: 48) was purified by "Silica Bead DNA Gel Extraction Kit" (Thermo Scientific) and used for electroporation of the strain MG1655 $P_L$-SD1-ilvG*MEDA, containing the plasmid pKD46. $Cm^R$ recombinants were selected and the deletion of the ilvE gene was verified by PCR using primers P18 (SEQ ID NO: 49) and P19 (SEQ ID NO: 50). Conditions for PCR verification were as follows: denaturation for 3 min at 95° C.; profile for the 25 cycles: 30 sec at 95° C., 30 sec at 59° C., 1 min at 72° C.; final elongation for 7 min at 72° C. DNA fragment 16 (SEQ ID NO: 51), obtained in the reaction with DNA of the cells of the parent strain MG1655 $P_L$-SD1-ilvG*MEDA as a template, was 1354 bp in length. DNA fragment 17 (SEQ ID NO: 52), obtained in the reaction with DNA of the cells of the strain MG1655 $P_L$-ilvG*M-ΔilvE:: cat-DA as a template, was 2015 bp in length.

Then, the expression cassette $P_L$-ilvG*M-ΔilvE::cat-DA was introduced into the strain L1194-2 by P1-transduction. $Cm^R$ cells of the strain L1194-2 that harbor the cassette $P_L$-ilvG*M-ΔilvE::cat-DA were selected. The replacement of the cassette $P_L$-SD1-ilvG*MEDA by the cassette $P_L$-ilvG*M-ΔilvE::cat-DA in the strain L1194-2 was confirmed using PCR as described above. After λ-Int/Xis-mediated excision of $Cm^R$-marker, the IlvE-deficient strain L1201-1 was obtained. Excision was confirmed by PCR using primers P18 (SEQ ID NO: 49) and P19 (SEQ ID NO: 50) as described above. DNA fragment 17 (SEQ ID NO: 52), obtained in the reaction with DNA of the cells of the parent strain L1194-2 $P_L$-ilvG*M-ΔilvE::cat-DA as a template, was 2015 bp in length. DNA fragment 18 (SEQ ID NO: 53), obtained in the reaction with DNA of the cells of the strain L1201-1 as a template, was 405 bp in length.

Example 4

Construction of E. coli Strain L1201-1 ΔtyrB::cat

The tyrB gene deletion in the chromosome of E. coli MG1655 strain (ATCC 47076) was constructed by the method of Red-dependent integration described above. According to this procedure, the PCR primers P20 (SEQ ID NO: 54) and P21 (SEQ ID NO: 55) homologous to both the region adjacent to the tyrB gene and the gene conferring chloramphenicol resistance in the template plasmid, were constructed. The plasmid pMW118-attL-cat-attR was used as a template in PCR reaction. Conditions for PCR were as follows: denaturation for 3 min at 95° C.; profile for two first cycles: 1 min at 95° C., 30 sec at 34° C., 80 sec at 72° C.; profile for the last 28 cycles: 30 sec at 95° C., 30 sec at 50° C., 80 sec at 72° C.; final elongation for 5 min at 72° C. The obtained DNA fragment 19 (1713 bp) (SEQ ID NO: 56) was purified by "Silica Bead DNA Gel Extraction Kit" (Thermo Scientific) and used for electroporation of the E. coli strain MG1655 containing the plasmid pKD46. $Cm^R$ recombinants were selected and the deletion of the tyrB gene marked with $Cm^R$ gene in selected mutants was verified by PCR using primers P22 (SEQ ID NO: 57) and P23 (SEQ ID NO: 58). Conditions for PCR verification were as follows: denaturation for 3 min at 95° C.; profile for the 25 cycles: 30 sec at 95° C., 30 sec at 55° C., 1 min at 72° C.; final elongation for 7 min at 72° C. DNA fragment 20 (SEQ ID NO: 59), obtained in the reaction with DNA of the cells of the parent strain MG1655 as a template, was 1430 bp in length. DNA fragment 21 (SEQ ID NO: 60), obtained in the reaction with DNA of the cells of the strain MG1655 ΔtyrB::cat as a template, was 1894 bp in length. Thus, the strain MG1655 ΔtyrB::cat was obtained.

The strain MG1655 ΔtyrB::cat was used as a donor for P1-transduction of the tyrB gene deletion into the strain L1201-1 (Example 3). $Cm^R$ recombinants were selected and the tyrB gene deletion in selected mutants was verified by PCR as described above. As a result, the strain L1201-1 ΔtyrB::cat was obtained.

Example 5

Production of 2-Methyl-Butyric Acid and Byproduct Substances using E. coli L1201-1 ΔtyrB::cat strain The modified strain L1201-1 ΔtyrB::cat and the control strain L1201-1 were each cultivated at 37° C. for 6 hours in LB-medium. Then, 0.1 mL of the obtained culture was inoculated into 2 mL of a fermentation medium supplemented with Ile, Val and Leu (200 mg/L each) for the strain L1201-1 and Ile, Val, Leu, Tyr and Phe (200 mg/L each) for the strain L1201-1 ΔtyrB::cat in 20×200-mm test tubes and cultivated at 30° C. for 66 hours on a rotary shaker at 238 rpm. After cultivation, the accumulated 2-methyl-butyric acid and isobutyric acid were measured using GC (gas chromatography) analysis (Auxiliary example 1). The accumulated 3-methyl-butyric acid was measured using GC-MS (gas chromatography mass-spectrometry) analysis (Auxiliary example 2).

The results of three independent test-tube fermentations are shown in Table 2. As one can see from the Table 2, the modified L1201-1 ΔtyrB::cat strain was able to accumulate 3-methyl-butyric acid (3-MB) in an amount lower as compared with the control L1201-1 strain. As one can also see from the Table 2, the modified L1201-1 ΔtyrB::cat strain was able to accumulate isobutyric acid (IBA) in an amount lower as compared with the control L1201-1 strain.

TABLE 2

Production of 2-methyl-butyric acid (2-MB), 3-methyl-butyric acid (3-MB), and isobutyric acid (IBA) using E. coli strains L1201-1 and L1201-1 ΔtyrB::cat

| Strain | $OD_{600}$ | 2-MB, g/L | 3-MB, g/L | 3-MB/2-MB, % | IBA, g/L | IBA/2-MB, % |
|---|---|---|---|---|---|---|
| L1201-1 | 10.8 | 5.8 | 1.33 | 23 | 3.9 | 67 |
| L1201-1 ΔtyrB::cat | 9.2 | 5.6 | 1.01 | 18 | 2.4 | 42 |

Example 6

Construction of E. coli Strain L1201-1 ΔtyrB ΔleuABCD::cat

The leuABCD operon deletion in the chromosome of E. coli MG1655 strain was constructed by the method of Red-dependent integration described above. According to this procedure, the PCR primers P24 (SEQ ID NO: 61) and P25 (SEQ ID NO: 62) homologous to both the region adjacent to the leuABCD operon and the gene conferring chloramphenicol resistance in the template plasmid, were constructed. The plasmid pMW118-attL-cat-attR was used as a template in PCR reaction. Conditions for PCR were as follows: denaturation for 3 min at 95° C.; profile for two first cycles: 1 min at 95° C., 30 sec at 34° C., 80 sec at 72° C.; profile for the last 28 cycles: 30 sec at 95° C., 30 sec at 50° C., 80 sec at 72° C.; final elongation for 5 min at 72° C. The obtained DNA fragment 22 (1713 bp) (SEQ ID NO: 63) was purified by "Silica Bead DNA Gel Extraction Kit" (Thermo Scientific) and used for electroporation of the E. coli strain MG1655, containing the plasmid pKD46. $Cm^R$ recombinants were selected and the deletion of the leuABCD operon marked with $Cm^R$ gene in selected mutants was verified by PCR using primers P26 (SEQ ID NO: 64) and P27 (SEQ ID NO: 65). Conditions for PCR verification were as follows: denaturation for 3 min at 95° C.; profile for the 25 cycles: 30 sec at 95° C., 30 sec at 55° C., 1 min at 72° C.; final elongation for 7 min at 72° C. DNA fragment 23 (SEQ ID NO: 66), obtained in the reaction with DNA of the cells of the parent strain MG1655 as a template, was 5172 bp in length. DNA fragment 24 (SEQ ID NO: 67), obtained in the reaction with DNA of the cells of the strain MG1655 ΔleuABCD::cat as a template, was 1868 bp in length. As a result, the strain MG1655 ΔleuABCD::cat was obtained.

The strain MG1655 ΔleuABCD::cat was used as a donor for P1-transduction of the leuABCD operon deletion into the strain L1201-1 ΔtyrB. The strain L1201-1 ΔtyrB was obtained from the strain L1201-1 ΔtyrB::cat (Example 4) by λ-Int/Xis-mediated excision of $Cm^R$-marker. Excision was confirmed by PCR using primers P22 (SEQ ID NO: 57) and P23 (SEQ ID NO: 58). Conditions for PCR were as follows: denaturation for 3 min at 95° C.; profile for the 25 cycles: 30 sec at 95° C., 30 sec at 55° C., 1 min at 72° C.; final elongation for 7 min at 72° C. DNA fragment 21 (SEQ ID NO: 60), obtained in the reaction with DNA of the cells of the parent strain L1201-1 ΔtyrB::cat as a template, was 1894 bp in length. DNA fragment 25 (SEQ ID NO: 68), obtained in the reaction with DNA of the cells of the strain L1201-1 ΔtyrB as a template, was 284 bp in length. $Cm^R$ recombinants were obtained and the deletion of the leuABCD operon in selected mutants was verified by PCR as described above. Thus, the strain L1201-1 ΔtyrB ΔleuABCD::cat was obtained.

Example 7

Production of 2-Methyl-Butyric Acid and a Byproduct Substance using *E. coli* L1201-1 ΔtyrB ΔleuABCD::cat strain The modified strain L1201-1 ΔtyrB ΔleuABCD::cat and the control strain L1201-1 ΔtyrB::cat were each cultivated at 37° C. for 6 hours in LB-medium. Then, 0.1 mL of the obtained culture was inoculated into 2 mL of a fermentation medium supplemented with Ile, Val, Leu, Tyr and Phe (200 mg/L each) in 20×200-mm test tubes and cultivated at 30° C. for 66 hours on a rotary shaker at 238 rpm. After cultivation, the accumulated 2-methyl-butyric acid was measured using GC analysis (Auxiliary example 1). The accumulated 3-methyl-butyric acid was measured using GC-MS analysis (Auxiliary example 2).

The results of three independent test-tube fermentations are shown in Table 3. As one can see from the Table 3, the modified strain L1201-1 ΔtyrB ΔleuABCD::cat was able to accumulate 3-methyl-butyric acid in a lower amount as compared with the control L1201-1 strain.

TABLE 3

Production of 2-methyl-butyric acid (2 MB) and 3 methyl-butyric acid (3-MB) using *E. coli* strains L1201-1 ΔtyrB::cat and L1201-1 ΔtyrB ΔleuABCD::cat

| Strain | $OD_{600}$ | 2-MB, g/L | 3-MB, g/L | 3-MB/ 2-MB, % |
|---|---|---|---|---|
| L1201-1 ΔtyrB::cat | 9.2 | 5.6 | 1.01 | 18 |
| L1201-1 ΔtyrB ΔleuABCD::cat | 9.0 | 4.7 | 0.23 | 5 |

Auxiliary Example 1. GC Analysis of 2-methyl-butyric acid and isobutyric acid

Shimadzu GC-2014 Gas chromatography system equipped with a flame ionization detector (FID) was used for the analysis of 2-methyl-butyric acid and isobutyric acid in a fermentation medium. Samples were resuspended and mixed with a 1% (v/v) solution of formic acid in ethanol. Then, the samples were agitated on a vortex for 3 minutes and centrifuged at 13,000 rpm for 5 minutes. A supernatant was used for direct analysis of 2-methyl-butyric acid and isobutyric acid. Standards were dissolved directly in a mixture of ethanol and 1% (v/v) of formic acid. Calibration range was from 5 to 160 mg/L. Other parameters were as follows:

Column: InertCap Pure-WAX (GL science Inc.)
Column size: I.D. 0.25 mm, length 30 m, film thickness 0.5 μm
Column gradient: 65° C. (5 min hold)-5° C./min-200° C.-10° C./min-240° C.
Injector temperature: 240° C.
Injection amount: 1.0 μL
Injection mode split: 1:10
Carrier gas: He
Control mode: line velocity
Pressure: 89.0 kPa
Total flow: 14.0 mL/min
Column flow: 1.0 mL/min
Line velocity: 26.1 cm/sec
Purge flow: 3.0 mL/min
Detector: FID 260° C.
Before injection: washing with the sample, 8 μL (3 times)
After injection: washing with ethanol, 8 μL (3 times)

Auxiliary Example 2. GC-MS Analysis of 3-methyl-butyric acid

Supernatants of fermentation media were collected from two tubes, combined to 2 mL, and filtered using 0.2 μm pore size filter to remove cells. Then, 1 mL of diluted sample was used for GC-MS analysis. GC-FID analysis was accomplished on Agilent 7890A chromatograph equipped with SUPELCO β-DEX 120 column. Column size was as follows: I.D. 0.25 mm, length 30 m, film thickness 0.25 μm; limit of detection (LOD) was 0.05 mg/L.

While the invention has been described in detail with reference to exemplary embodiments thereof, it will be apparent to the one of ordinary skill in the art that various changes can be made, and equivalents employed, without departing from the scope of the invention.

INDUSTRIAL APPLICABILITY

The method of the present invention is useful for the production of highly pure 2-methyl-butyric acid by fermentation of a bacterium.

The invention claimed is:

1. A method for producing 2-methyl-butyric acid comprising:
   (i) cultivating in a culture medium a 2-methyl-butyric acid-producing bacterium belonging to the genus *Escherichia* to produce and accumulate 2-methyl-butyric acid in the culture medium or cells of the bacterium, or both, and
   (ii) collecting 2-methyl-butyric acid from the culture medium or the cells of the bacterium, or both,
   wherein said bacterium has been modified to attenuate expression of a gene encoding a protein having tyrosine aminotransferase activity;
   wherein said expression of the gene encoding a protein having tyrosine aminotransferase activity is attenuated due to inactivation of the gene,
   wherein said gene encoding a protein having tyrosine aminotransferase activity is a tyrB gene, and
   wherein said protein having tyrosine aminotransferase activity is selected from the group consisting of:
   (A) a protein comprising the amino acid sequence set forth in SEQ ID NO: 2,
   (B) a protein comprising the amino acid sequence set forth in SEQ ID NO: 2, comprising substitution, deletion, insertion and/or addition of 1 to 30 amino acid residues, and wherein said protein has tyrosine aminotransferase activity, and
   (C) a protein comprising an amino acid sequence having an identity of not less than 90% with respect to the entire amino acid sequence set forth in SEQ ID NO: 2, and wherein said protein has tyrosine aminotransferase activity.

2. The method of claim 1, wherein said gene is selected from the group consisting of:
   (a) a gene comprising the nucleotide sequence set forth in SEQ ID NO: 1,
   (b) a gene comprising a nucleotide sequence that hybridizes under stringent conditions with a nucleotide sequence complementary to the sequence set forth in SEQ ID NO: 1, wherein the stringent conditions comprise washing one or more times at a salt concentration of at least 1×SSC, 0.1% SDS at, at least 60° C., and wherein the gene encodes a protein having tyrosine aminotransferase activity,
   (c) a gene encoding a protein comprising the amino acid sequence set forth in SEQ ID NO: 2, comprising substitution, deletion, insertion and/or addition of 1 to 30 amino acid residues, and wherein said protein has tyrosine aminotransferase activity, and
   (d) a gene comprising a variant nucleotide sequence of SEQ ID NO: 1, wherein the variant nucleotide sequence is due to the degeneracy of the genetic code.

3. The method of claim 1, wherein said gene encoding a protein having tyrosine aminotransferase activity is deleted.

4. The method of claim 1, wherein said bacterium is *Escherichia coli*.

5. The method of claim 1, wherein said bacterium has been modified further to attenuate expression of a gene selected from the group consisting of leuA, leuB, leuC, leuD, and combinations thereof.

6. The method of claim 1, wherein byproduct of the 2-methyl-butyric acid is reduced as compared with a non-modified bacterium.

7. The method of claim 6, wherein the byproduct is selected from the group consisting of 3-methyl-butyric acid, isobutyric acid, L-allo-isoleucine, D-allo-isoleucine, and combinations thereof.

* * * * *

SEQUENCE LISTING

<160> NUMBER OF SEQ ID NOS: 69

<210> SEQ ID NO 1
<211> LENGTH: 1194
<212> TYPE: DNA
<213> ORGANISM: Escherichia coli

<400> SEQUENCE: 1

-continued

```
gtgtttcaaa aagttgacgc ctacgctggc gacccgattc ttacgcttat ggagcgtttt      60
aaagaagacc ctcgcagcga caaagtgaat ttaagtatcg gtctgtacta caacgaagac     120
ggaattattc cacaactgca agccgtggcg gaggcggaag cgcgcctgaa tgcgcagcct     180
catggcgctt cgctttattt accgatggaa gggcttaact gctatcgcca tgccattgcg     240
ccgctgctgt ttggtgcgga ccatccggta ctgaaacaac agcgcgtagc aaccattcaa     300
acccttggcg gctccggggc attgaaagtg gcgcgcgatt tcctgaaacg ctacttcccg     360
gaatcaggcg tctgggtcag cgatcctacc tgggaaaacc acgtagcaat attcgccggg     420
gctggattcg aagtgagtac ttaccccctgg tatgacgaag cgactaacgg cgtgcgcttt     480
```
<br>
(Note: line 8 above reads `gctggattcg aagtgagtac ttaccctgg tatgacgaag cgactaacgg cgtgcgcttt`)

```
aatgacctgt tggcgacgct gaaaacatta cctgcccgca gtattgtgtt gctgcatcca     540
tgttgccaca acccaacggg tgccgatctc actaatgatc agtgggatgc ggtgattgaa     600
attctcaaag cccgcgagct tattccattc ctcgatattg cctatcaagg atttggtgcc     660
ggtatggaag aggatgccta cgctattcgc gccattgcca gcgctggatt acccgctctg     720
gtgagcaatt cgttctcgaa aattttctcc ctttacggcg agcgcgtcgg cggactttct     780
gttatgtgtg aagatgccga agccgctggc cgcgtactgg ggcaattgaa agcaacagtt     840
cgccgcaact actccagccc gccgaatttt ggtgcgcagg tggtggctgc agtgctgaat     900
gacgaggcat tgaaagccag ctggctggcg gaagtagaag agatgcgtac tcgcattctg     960
gcaatgcgtc aggaattggt gaaggtatta agcacagaga tgccagaacg caatttcgat    1020
tatctgctta atcagcgcgg catgttcagt tataccggtt taagtgccgc tcaggttgac    1080
cgactacgtg aagaatttgg tgtctatctc atcgccagcg gtcgcatgtg tgtcgccggg    1140
ttaaatacgg caaatgtaca acgtgtggca aaggcgtttg ctgcggtgat gtaa          1194
```

<210> SEQ ID NO 2
<211> LENGTH: 397
<212> TYPE: PRT
<213> ORGANISM: Escherichia coli

<400> SEQUENCE: 2

```
Met Phe Gln Lys Val Asp Ala Tyr Ala Gly Asp Pro Ile Leu Thr Leu
1               5                   10                  15

Met Glu Arg Phe Lys Glu Asp Pro Arg Ser Asp Lys Val Asn Leu Ser
                20                  25                  30

Ile Gly Leu Tyr Tyr Asn Glu Asp Gly Ile Ile Pro Gln Leu Gln Ala
            35                  40                  45

Val Ala Glu Ala Glu Ala Arg Leu Asn Ala Gln Pro His Gly Ala Ser
        50                  55                  60

Leu Tyr Leu Pro Met Glu Gly Leu Asn Cys Tyr Arg His Ala Ile Ala
65                  70                  75                  80

Pro Leu Leu Phe Gly Ala Asp His Pro Val Leu Lys Gln Gln Arg Val
                85                  90                  95

Ala Thr Ile Gln Thr Leu Gly Gly Ser Gly Ala Leu Lys Val Gly Ala
            100                 105                 110

Asp Phe Leu Lys Arg Tyr Phe Pro Glu Ser Gly Val Trp Val Ser Asp
        115                 120                 125

Pro Thr Trp Glu Asn His Val Ala Ile Phe Ala Gly Ala Gly Phe Glu
    130                 135                 140

Val Ser Thr Tyr Pro Trp Tyr Asp Glu Ala Thr Asn Gly Val Arg Phe
145                 150                 155                 160
```

```
Asn Asp Leu Leu Ala Thr Leu Lys Thr Leu Pro Ala Arg Ser Ile Val
                165                 170                 175

Leu Leu His Pro Cys Cys His Asn Pro Thr Gly Ala Asp Leu Thr Asn
            180                 185                 190

Asp Gln Trp Asp Ala Val Ile Glu Ile Leu Lys Ala Arg Glu Leu Ile
        195                 200                 205

Pro Phe Leu Asp Ile Ala Tyr Gln Gly Phe Gly Ala Gly Met Glu Glu
    210                 215                 220

Asp Ala Tyr Ala Ile Arg Ala Ile Ala Ser Ala Gly Leu Pro Ala Leu
225                 230                 235                 240

Val Ser Asn Ser Phe Ser Lys Ile Phe Ser Leu Tyr Gly Glu Arg Val
                245                 250                 255

Gly Gly Leu Ser Val Met Cys Glu Asp Ala Glu Ala Ala Gly Arg Val
            260                 265                 270

Leu Gly Gln Leu Lys Ala Thr Val Arg Arg Asn Tyr Ser Ser Pro Pro
        275                 280                 285

Asn Phe Gly Ala Gln Val Val Ala Ala Val Leu Asn Asp Glu Ala Leu
    290                 295                 300

Lys Ala Ser Trp Leu Ala Glu Val Glu Glu Met Arg Thr Arg Ile Leu
305                 310                 315                 320

Ala Met Arg Gln Glu Leu Val Lys Val Leu Ser Thr Glu Met Pro Glu
                325                 330                 335

Arg Asn Phe Asp Tyr Leu Leu Asn Gln Arg Gly Met Phe Ser Tyr Thr
            340                 345                 350

Gly Leu Ser Ala Ala Gln Val Asp Arg Leu Arg Glu Glu Phe Gly Val
        355                 360                 365

Tyr Leu Ile Ala Ser Gly Arg Met Cys Val Ala Gly Leu Asn Thr Ala
    370                 375                 380

Asn Val Gln Arg Val Ala Lys Ala Phe Ala Ala Val Met
385                 390                 395

<210> SEQ ID NO 3
<211> LENGTH: 1572
<212> TYPE: DNA
<213> ORGANISM: Escherichia coli

<400> SEQUENCE: 3
atgagccagc aagtcattat tttcgatacc acattgcgcg acggtgaaca ggcgttacag      60
gcaagcttga gtgtgaaaga aaaactgcaa attgcgctgg cccttgagcg tatgggtgtt     120
gacgtgatga agtcgggttt ccccgtctct tcgccgggcg attttgaatc ggtgcaaacc     180
atcgcccgcc aggttaaaaa cagccgcgta tgtgcgttag ctcgctgcgt ggaaaaagat     240
atcgacgtgg cggccgaatc cctgaaagtc gccgaagcct tccgtattca tacctttatt     300
gccacttcgc caatgcacat cgccaccaag ctgcgcagca cgctggacga ggtgatcgaa     360
cgcgctatct atatggtgaa acgcgcccgt aattacaccg atgatgttga attttcttgc     420
gaagatgccg gcgtacacc cattgccgat ctggcgcgag tggtcgaagc ggcgattaat     480
gccggtgcca ccaccatcaa cattccggac accgtgggct acaccatgcc gtttgagttc     540
gccggaatca tcagcggcct gtatgaacgc gtgcctaaca tcgacaaagc cattatctcc     600
gtacataccc acgacgattt gggcctggcg tcggaaact cactggcggc ggtacatgcc     660
ggtgcacgcc aggtggaagg cgcaatgaac gggatcggcg agcgtgccgg aaactgttcc     720
ctggaagaag tcatcatggc gatcaaagtt cgtaaggata ttctcaacgt ccacaccgcc     780
```

-continued

```
attaatcacc aggagatatg gcgcaccagc cagttagtta gccagatttg taatatgccg    840
atcccggcaa acaaagccat tgttggcagc ggcgcattcg cacactcctc cggtatacac    900
caggatggcg tgctgaaaaa ccgcgaaaac tacgaaatca tgacaccaga atctattggt    960
ctgaaccaaa tccagctgaa tctgacctct cgttcggggc gtgcggcggt gaaacatcgc   1020
atggatgaga tgggtataa agaaagtgaa tataatttag acaatttgta cgatgctttc   1080
ctgaagctgg cggacaaaaa aggtcaggtg tttgattacg atctggaggc gctggccttc   1140
atcggtaagc agcaagaaga gccggagcat ttccgtctgg attacttcag cgtgcagtct   1200
ggctctaacg atatcgccac cgccgccgtc aaactggcct gtggcgaaga agtcaaagca   1260
gaagccgcca acggtaacgg tccggtcgat gccgtctatc aggcaattaa ccgcatcact   1320
gaatataacg tcgaactggt gaaatacagc ctgaccgcca aaggccacgg taaagatgcg   1380
ctgggtcagg tggatatcgt cgctaactac aacggtcgcc gcttccacgg cgtcggcctg   1440
gctaccgata ttgtcgagtc atctgccaaa gccatggtgc acgttctgaa caatatctgg   1500
cgtgccgcag aagtcgaaaa agagttgcaa cgcaaagctc aacacaacga aacaacaag    1560
gaaaccgtgt ga                                                       1572
```

<210> SEQ ID NO 4
<211> LENGTH: 523
<212> TYPE: PRT
<213> ORGANISM: Escherichia coli

<400> SEQUENCE: 4

```
Met Ser Gln Gln Val Ile Ile Phe Asp Thr Thr Leu Arg Asp Gly Glu
1               5                   10                  15

Gln Ala Leu Gln Ala Ser Leu Ser Val Lys Glu Lys Leu Gln Ile Ala
            20                  25                  30

Leu Ala Leu Glu Arg Met Gly Val Asp Val Met Glu Val Gly Phe Pro
        35                  40                  45

Val Ser Ser Pro Gly Asp Phe Glu Ser Val Gln Thr Ile Ala Arg Gln
    50                  55                  60

Val Lys Asn Ser Arg Val Cys Ala Leu Ala Arg Cys Val Glu Lys Asp
65                  70                  75                  80

Ile Asp Val Ala Ala Glu Ser Leu Lys Val Ala Glu Ala Phe Arg Ile
                85                  90                  95

His Thr Phe Ile Ala Thr Ser Pro Met His Ile Ala Thr Lys Leu Arg
            100                 105                 110

Ser Thr Leu Asp Glu Val Ile Glu Arg Ala Ile Tyr Met Val Lys Arg
        115                 120                 125

Ala Arg Asn Tyr Thr Asp Asp Val Glu Phe Ser Cys Glu Asp Ala Gly
    130                 135                 140

Arg Thr Pro Ile Ala Asp Leu Ala Arg Val Val Glu Ala Ala Ile Asn
145                 150                 155                 160

Ala Gly Ala Thr Thr Ile Asn Ile Pro Asp Thr Val Gly Tyr Thr Met
                165                 170                 175

Pro Phe Glu Phe Ala Gly Ile Ile Ser Gly Leu Tyr Glu Arg Val Pro
            180                 185                 190

Asn Ile Asp Lys Ala Ile Ile Ser Val His Thr His Asp Asp Leu Gly
        195                 200                 205

Leu Ala Val Gly Asn Ser Leu Ala Ala Val His Ala Gly Ala Arg Gln
    210                 215                 220

Val Glu Gly Ala Met Asn Gly Ile Gly Glu Arg Ala Gly Asn Cys Ser
```

```
                225                 230                 235                 240
Leu Glu Glu Val Ile Met Ala Ile Lys Val Arg Lys Asp Ile Leu Asn
                    245                 250                 255

Val His Thr Ala Ile Asn His Gln Glu Ile Trp Arg Thr Ser Gln Leu
                260                 265                 270

Val Ser Gln Ile Cys Asn Met Pro Ile Pro Ala Asn Lys Ala Ile Val
            275                 280                 285

Gly Ser Gly Ala Phe Ala His Ser Ser Gly Ile His Gln Asp Gly Val
        290                 295                 300

Leu Lys Asn Arg Glu Asn Tyr Glu Ile Met Thr Pro Glu Ser Ile Gly
305                 310                 315                 320

Leu Asn Gln Ile Gln Leu Asn Leu Thr Ser Arg Ser Gly Arg Ala Ala
                325                 330                 335

Val Lys His Arg Met Asp Glu Met Gly Tyr Lys Glu Ser Glu Tyr Asn
                340                 345                 350

Leu Asp Asn Leu Tyr Asp Ala Phe Leu Lys Leu Ala Asp Lys Lys Gly
            355                 360                 365

Gln Val Phe Asp Tyr Asp Leu Glu Ala Leu Ala Phe Ile Gly Lys Gln
        370                 375                 380

Gln Glu Glu Pro Glu His Phe Arg Leu Asp Tyr Phe Ser Val Gln Ser
385                 390                 395                 400

Gly Ser Asn Asp Ile Ala Thr Ala Ala Val Lys Leu Ala Cys Gly Glu
                405                 410                 415

Glu Val Lys Ala Glu Ala Asn Gly Asn Gly Pro Val Asp Ala Val
                420                 425                 430

Tyr Gln Ala Ile Asn Arg Ile Thr Glu Tyr Asn Val Glu Leu Val Lys
            435                 440                 445

Tyr Ser Leu Thr Ala Lys Gly His Gly Lys Asp Ala Leu Gly Gln Val
        450                 455                 460

Asp Ile Val Ala Asn Tyr Asn Gly Arg Arg Phe His Gly Val Gly Leu
465                 470                 475                 480

Ala Thr Asp Ile Val Glu Ser Ser Ala Lys Ala Met Val His Val Leu
                485                 490                 495

Asn Asn Ile Trp Arg Ala Ala Glu Val Glu Lys Glu Leu Gln Arg Lys
                500                 505                 510

Ala Gln His Asn Glu Asn Asn Lys Glu Thr Val
            515                 520

<210> SEQ ID NO 5
<211> LENGTH: 1092
<212> TYPE: DNA
<213> ORGANISM: Escherichia coli

<400> SEQUENCE: 5
atgtcgaaga attaccatat tgccgtattg ccgggggacg gtattggtcc ggaagtgatg      60
acccaggcgc tgaaagtgct ggatgccgtg cgcaaccgct tgcgatgcg catcaccacc     120 agccattacg atgtaggcgg cgcagccatt gataaccacg gcaaccact gccgcctgcg     180 acggttgaag ttgtgagca agccgatgcc gtgctgtttg ctcggtagg cggcccgaag     240 tgggaacatt taccaccaga ccagcaacca gaacgcggcg cgctgctgcc tctgcgtaag     300
cacttcaaat tattcagcaa cctgcgcccg gcaaaactgt atcaggggct ggaagcattc     360
tgtccgctgc gtgcagacat tgccgcaaac ggcttcgaca tcctgtgtgt gcgcgaactg     420
accggcggca tctattcgg tcagccaaaa ggccgcgaag gtagcggaca atatgaaaaa     480
```

-continued

```
gcctttgata ccgaggtgta tcaccgtttt gagatcgaac gtatcgcccg catcgcgttt    540
gaatctgctc gcaagcgtcg ccacaaagtg acgtcgatcg ataaagccaa cgtgctgcaa    600
tcctctattt tatggcggga gatcgttaac gagatcgcca cggaataccc ggatgtcgaa    660
ctggcgcata tgtacatcga caacgccacc atgcagctga ttaaagatcc atcacagttt    720
gacgttctgc tgtgctccaa cctgtttggc gacattctgt ctgacgagtg cgcaatgatc    780
actggctcga tggggatgtt gccttccgcc agcctgaacg agcaaggttt tggactgtat    840
gaaccggcgg gcggctcggc accagatatc gcaggcaaaa acatcgccaa cccgattgca    900
caaatccttt cgctggcact gctgctgcgt tacagcctgg atgccgatga tgcggcttgc    960
gccattgaac gcgccattaa ccgcgcatta aagaaggca ttcgcaccgg ggatttagcc   1020
cgtggcgctg ccgccgttag taccgatgaa atgggcgata tcattgcccg ctatgtagca   1080 gaagggtgt aa                                                        1092
```

<210> SEQ ID NO 6
<211> LENGTH: 363
<212> TYPE: PRT
<213> ORGANISM: Escherichia coli

<400> SEQUENCE: 6

```
Met Ser Lys Asn Tyr His Ile Ala Val Leu Pro Gly Asp Gly Ile Gly
1               5                   10                  15

Pro Glu Val Met Thr Gln Ala Leu Lys Val Leu Asp Ala Val Arg Asn
            20                  25                  30

Arg Phe Ala Met Arg Ile Thr Thr Ser His Tyr Asp Val Gly Gly Ala
        35                  40                  45

Ala Ile Asp Asn His Gly Gln Pro Leu Pro Pro Ala Thr Val Glu Gly
    50                  55                  60

Cys Glu Gln Ala Asp Ala Val Leu Phe Gly Ser Val Gly Gly Pro Lys
65                  70                  75                  80

Trp Glu His Leu Pro Pro Asp Gln Gln Pro Glu Arg Gly Ala Leu Leu
                85                  90                  95

Pro Leu Arg Lys His Phe Lys Leu Phe Ser Asn Leu Arg Pro Ala Lys
            100                 105                 110

Leu Tyr Gln Gly Leu Glu Ala Phe Cys Pro Leu Arg Ala Asp Ile Ala
        115                 120                 125

Ala Asn Gly Phe Asp Ile Leu Cys Val Arg Glu Leu Thr Gly Gly Ile
    130                 135                 140

Tyr Phe Gly Gln Pro Lys Gly Arg Glu Gly Ser Gly Gln Tyr Glu Lys
145                 150                 155                 160

Ala Phe Asp Thr Glu Val Tyr His Arg Phe Glu Ile Glu Arg Ile Ala
                165                 170                 175

Arg Ile Ala Phe Glu Ser Ala Arg Lys Arg Arg His Lys Val Thr Ser
            180                 185                 190

Ile Asp Lys Ala Asn Val Leu Gln Ser Ser Ile Leu Trp Arg Glu Ile
        195                 200                 205

Val Asn Glu Ile Ala Thr Glu Tyr Pro Asp Val Glu Leu Ala His Met
    210                 215                 220

Tyr Ile Asp Asn Ala Thr Met Gln Leu Ile Lys Asp Pro Ser Gln Phe
225                 230                 235                 240

Asp Val Leu Leu Cys Ser Asn Leu Phe Gly Asp Ile Leu Ser Asp Glu
                245                 250                 255
```

```
Cys Ala Met Ile Thr Gly Ser Met Gly Met Leu Pro Ser Ala Ser Leu
            260                 265                 270

Asn Glu Gln Gly Phe Gly Leu Tyr Glu Pro Ala Gly Gly Ser Ala Pro
        275                 280                 285

Asp Ile Ala Gly Lys Asn Ile Ala Asn Pro Ile Ala Gln Ile Leu Ser
    290                 295                 300

Leu Ala Leu Leu Leu Arg Tyr Ser Leu Asp Asp Asp Ala Ala Cys
305                 310                 315                 320

Ala Ile Glu Arg Ala Ile Asn Arg Ala Leu Glu Glu Gly Ile Arg Thr
                325                 330                 335

Gly Asp Leu Ala Arg Gly Ala Ala Ala Val Ser Thr Asp Glu Met Gly
            340                 345                 350

Asp Ile Ile Ala Arg Tyr Val Ala Glu Gly Val
            355                 360
```

<210> SEQ ID NO 7
<211> LENGTH: 1401
<212> TYPE: DNA
<213> ORGANISM: Escherichia coli

<400> SEQUENCE: 7

```
atggctaaga cgttatacga aaaattgttc gacgctcacg ttgtgtacga agccgaaaac      60
gaaaccccac tgttatatat cgaccgccac ctggtgcatg aagtgacctc accgcaggcg    120
ttcgatggtc tgcgcgccca cggtcgcccg gtacgtcagc cgggcaaaac cttcgctacc    180
atggatcaca acgtctctac ccagaccaaa gacattaatg cctgcggtga atggcgcgt    240
atccagatgc aggaactgat caaaaactgc aaagaatttg gcgtcgaact gtatgacctg    300
aatcacccgt atcaggggat cgtccacgta atggggccgg aacagggcgt caccttgccg    360
gggatgacca ttgtctgcgg cgactcgcat accgccaccc acggcgcgtt tggcgcactg    420
gcctttggta tcggcacttc cgaagttgaa cacgtactgg caacgcaaac cctgaaacag    480
ggccgcgcaa aaaccatgaa aattgaagtc cagggcaaag ccgcgccggg cattaccgca    540
aaagatatcg tgctggcaat tatcggtaaa accggtagcg caggcggcac cgggcatgtg    600
gtggagtttt gcggcgaagc aatccgtgat ttaagcatgg aaggtcgtat gaccctgtgc    660
aatatggcaa tcgaaatggg cgcaaaagcc ggtctggttg caccggacga aaccaccttt    720
aactatgtca aaggccgtct gcatgcgccg aaaggcaaag atttcgacga cgccgttgcc    780
tactggaaaa ccctgcaaac cgacgaaggc gcaactttcg ataccgttgt cactctgcaa    840
gcagaagaaa tttcaccgca ggtcacctgg ggcaccaatc ccggccaggt gatttccgtg    900
aacgacaata ttcccgatcc ggcttcgttt gccgatccgg ttgaacgcgc gtcggcagaa    960
aaagcgctgg cctatatggg gctgaaaccg gtattccgc tgaccgaagt ggctatcgac   1020
aaagtgttta tcggttcctg taccaactcg cgcattgaag atttacgcgc ggcagcggag   1080
atcgccaaag gcgaaaagt cgcgccaggc gtgcaggcac tggtggttcc cggctctggc   1140
ccggtaaaag cccaggcgga agcggaaggt ctggataaaa tctttattga gccggttttt   1200
gaatggcgct tgcctggctg ctcaatgtgt ctggcgatga caacgaccg tctgaatccg   1260
ggcgaacgtt gtgcctccac cagcaaccgt aactttgaag ccgcagggg gcgcggcggg   1320
cgcacgcatc tggtcagccc ggcaatggct gccgctgctg ctgtgaccgg acatttcgcc   1380
gacattcgca acattaaata a                                             1401
```

<210> SEQ ID NO 8

```
<211> LENGTH: 466
<212> TYPE: PRT
<213> ORGANISM: Escherichia coli

<400> SEQUENCE: 8
```

| | | | | | | | | | | | | | | |
|---|---|---|---|---|---|---|---|---|---|---|---|---|---|---|
| Met | Ala | Lys | Thr | Leu | Tyr | Glu | Lys | Leu | Phe | Asp | Ala | His | Val | Val | Tyr |
| 1 | | | | 5 | | | | | 10 | | | | | 15 | |
| Glu | Ala | Glu | Asn | Glu | Thr | Pro | Leu | Leu | Tyr | Ile | Asp | Arg | His | Leu | Val |
| | | | 20 | | | | | 25 | | | | | 30 | | |
| His | Glu | Val | Thr | Ser | Pro | Gln | Ala | Phe | Asp | Gly | Leu | Arg | Ala | His | Gly |
| | | 35 | | | | | 40 | | | | | 45 | | | |
| Arg | Pro | Val | Arg | Gln | Pro | Gly | Lys | Thr | Phe | Ala | Thr | Met | Asp | His | Asn |
| 50 | | | | | 55 | | | | | 60 | | | | | |
| Val | Ser | Thr | Gln | Thr | Lys | Asp | Ile | Asn | Ala | Cys | Gly | Glu | Met | Ala | Arg |
| 65 | | | | | 70 | | | | | 75 | | | | | 80 |
| Ile | Gln | Met | Gln | Glu | Leu | Ile | Lys | Asn | Cys | Lys | Glu | Phe | Gly | Val | Glu |
| | | | | 85 | | | | | 90 | | | | | 95 | |
| Leu | Tyr | Asp | Leu | Asn | His | Pro | Tyr | Gln | Gly | Ile | Val | His | Val | Met | Gly |
| | | | 100 | | | | | 105 | | | | | 110 | | |
| Pro | Glu | Gln | Gly | Val | Thr | Leu | Pro | Gly | Met | Thr | Ile | Val | Cys | Gly | Asp |
| | | 115 | | | | | 120 | | | | | 125 | | | |
| Ser | His | Thr | Ala | Thr | His | Gly | Ala | Phe | Gly | Ala | Leu | Ala | Phe | Gly | Ile |
| 130 | | | | | 135 | | | | | 140 | | | | | |
| Gly | Thr | Ser | Glu | Val | Glu | His | Val | Leu | Ala | Thr | Gln | Thr | Leu | Lys | Gln |
| 145 | | | | | 150 | | | | | 155 | | | | | 160 |
| Gly | Arg | Ala | Lys | Thr | Met | Lys | Ile | Glu | Val | Gln | Gly | Lys | Ala | Ala | Pro |
| | | | | 165 | | | | | 170 | | | | | 175 | |
| Gly | Ile | Thr | Ala | Lys | Asp | Ile | Val | Leu | Ala | Ile | Ile | Gly | Lys | Thr | Gly |
| | | | 180 | | | | | 185 | | | | | 190 | | |
| Ser | Ala | Gly | Gly | Thr | Gly | His | Val | Val | Glu | Phe | Cys | Gly | Glu | Ala | Ile |
| | | 195 | | | | | 200 | | | | | 205 | | | |
| Arg | Asp | Leu | Ser | Met | Glu | Gly | Arg | Met | Thr | Leu | Cys | Asn | Met | Ala | Ile |
| 210 | | | | | 215 | | | | | 220 | | | | | |
| Glu | Met | Gly | Ala | Lys | Ala | Gly | Leu | Val | Ala | Pro | Asp | Glu | Thr | Thr | Phe |
| 225 | | | | | 230 | | | | | 235 | | | | | 240 |
| Asn | Tyr | Val | Lys | Gly | Arg | Leu | His | Ala | Pro | Lys | Gly | Lys | Asp | Phe | Asp |
| | | | | 245 | | | | | 250 | | | | | 255 | |
| Asp | Ala | Val | Ala | Tyr | Trp | Lys | Thr | Leu | Gln | Thr | Asp | Glu | Gly | Ala | Thr |
| | | | 260 | | | | | 265 | | | | | 270 | | |
| Phe | Asp | Thr | Val | Val | Thr | Leu | Gln | Ala | Glu | Glu | Ile | Ser | Pro | Gln | Val |
| | | 275 | | | | | 280 | | | | | 285 | | | |
| Thr | Trp | Gly | Thr | Asn | Pro | Gly | Gln | Val | Ile | Ser | Val | Asn | Asp | Asn | Ile |
| | 290 | | | | | 295 | | | | | 300 | | | | |
| Pro | Asp | Pro | Ala | Ser | Phe | Ala | Asp | Pro | Val | Glu | Arg | Ala | Ser | Ala | Glu |
| 305 | | | | | 310 | | | | | 315 | | | | | 320 |
| Lys | Ala | Leu | Ala | Tyr | Met | Gly | Leu | Lys | Pro | Gly | Ile | Pro | Leu | Thr | Glu |
| | | | | 325 | | | | | 330 | | | | | 335 | |
| Val | Ala | Ile | Asp | Lys | Val | Phe | Ile | Gly | Ser | Cys | Thr | Asn | Ser | Arg | Ile |
| | | | 340 | | | | | 345 | | | | | 350 | | |
| Glu | Asp | Leu | Arg | Ala | Ala | Ala | Glu | Ile | Ala | Lys | Gly | Arg | Lys | Val | Ala |
| | | | 355 | | | | | 360 | | | | | 365 | | |
| Pro | Gly | Val | Gln | Ala | Leu | Val | Val | Pro | Gly | Ser | Gly | Pro | Val | Lys | Ala |
| | 370 | | | | | 375 | | | | | 380 | | | | |
| Gln | Ala | Glu | Ala | Glu | Gly | Leu | Asp | Lys | Ile | Phe | Ile | Glu | Ala | Gly | Phe |

```
                385                 390                 395                 400
Glu Trp Arg Leu Pro Gly Cys Ser Met Cys Leu Ala Met Asn Asn Asp
                    405                 410                 415

Arg Leu Asn Pro Gly Glu Arg Cys Ala Ser Thr Ser Asn Arg Asn Phe
                420                 425                 430

Glu Gly Arg Gln Gly Arg Gly Arg Thr His Leu Val Ser Pro Ala
            435                 440                 445

Met Ala Ala Ala Ala Val Thr Gly His Phe Ala Asp Ile Arg Asn
450                 455                 460

Ile Lys
465

<210> SEQ ID NO 9
<211> LENGTH: 606
<212> TYPE: DNA
<213> ORGANISM: Escherichia coli

<400> SEQUENCE: 9
atggcagaga aatttatcaa acacacaggc ctggtggttc cgctggatgc cgccaatgtc      60
gataccgatg caatcatccc gaaacagttt ttgcagaaag tgacccgtac gggttttggc     120
gcgcatctgt ttaacgactg gcgttttctg atgaaaaag gccaacagcc aaacccggac     180
ttcgtgctga acttcccgca gtatcagggc gcttccattt tgctggcacg agaaaacttc     240
ggctgtggct cttcgcgtga gcacgcgccc tgggcattga ccgactacgg ttttaaagtg     300
gtgattgcgc cgagttttgc tgacatcttc tacggcaata gctttaacaa ccagctgctg     360
ccggtgaaat taagcgatgc agaagtggac gaactgtttg cgctggtgaa agctaatccg     420
gggatccatt tcgacgtgga tctggaagcg caagaggtga agcgggaga gaaaaccctat    480 cgctttacca tcgatgcctt ccgccgccac tgcatgatga acggtctgga cagtattggg     540
cttaccttgc agcacgacga cgccattgcc gcttatgaag caaaacaacc tgcgtttatg     600
aattaa                                                                606

<210> SEQ ID NO 10
<211> LENGTH: 201
<212> TYPE: PRT
<213> ORGANISM: Escherichia coli

<400> SEQUENCE: 10

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Leu Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu His Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125
```

```
Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 11
<211> LENGTH: 399
<212> TYPE: DNA
<213> ORGANISM: Artificial Sequence
<220> FEATURE:
<223> OTHER INFORMATION: tdh::attB

<400> SEQUENCE: 11
tttcttctat ccggtcgttc cgaaaggtca ggcgcgtatt cgtacccaga tgtctgcggc      60
gcatacccct gagcaaatta cgcgtgcagt agaagcattt acgcgtattg gtaaacaact     120
gggcgttatc gcctgaggat gtgagatgaa agcgttatcc aaactgaaag cggaagaggc     180
gctcaagtta gtataaaaaa gcaggcttca ggccagtccg ggaaagttat tctgagctgg     240
gattaacacg aacaagggct ggtattccag ccctttatc tgaggataat ctgttaaata      300
tgtaaaatcc tgtcagtgta ataaagagtt cgtaattgtg ctgatctctt atatagctgc     360
tctcattatc tctctaccct gaagtgactc tctcacctg                            399

<210> SEQ ID NO 12
<211> LENGTH: 5991
<212> TYPE: DNA
<213> ORGANISM: Artificial Sequence
<220> FEATURE:
<223> OTHER INFORMATION: mini-Mu::Plac-lacI-ilvA*-kan

<400> SEQUENCE: 12
tgtattgatt cacttgaagt acgaaaaaaa ccgggaggac attggattat tcgggatctg      60
atgggattag atttggtggg gcttgcaagc ctgtagtgca aattttagtc gttaatcaat     120
gaaacgcgaa agatagtaaa aaattgcttt tgtttcattg aaaatacgaa aaacaaaaac     180
actgcaaatc atttcaataa cagcttcaaa aaacgttcaa aaccgataac aaccaagctg     240
tcaccaaatg actcatatca caaatcagct tatgccgttt aggtatgtta catgtgtgat     300
tatgtgaggt gaagtatgtt ttagctggtt catggttgtt atacggcttt ttttacctcc     360
tgtggttcct gtgaaggtac tacaacactt tcctgttcat gaatcccata ctttgacaaa     420
atctctttgc gttttcttc aggtaatgca gtggtcgaaa aaaaagccc gcactgtcag      480 gtgcgggctt ttttctgtgt taagcttgca tgcaaggaga tggcgcccaa cagtcccccg     540
gccacggggc ctgccaccat acccacgccg aaacaagcgc tcatgagccc gaagtggcga     600
gcccgatctt ccccatcggt gatgtcggcg ataggcgc cagcaaccgc acctgtggcg     660
ccggtgatgc cggccacgat gcgtccggcg tagaggatcg agatcctttg cctggcggca     720
gtagcgcggt ggtcccacct gaccccatgc cgaactcaga agtgaaacgc cgtagcgccg     780
atggtagtgt ggggtctccc catgcgagag taggaactg ccaggcatca aataaaacga     840
aaggctcagt cgaaagactg ggcctttcgt tttatctgtt gtttgtcggt gaacgctctc     900
```

```
ctgagtagga caaatccgcc gggagcggat ttgaacgttg cgaagcaacg gcccggaggg      960
tggcgggcag gacgcccgcc ataaactgcc aggcatcaaa ttaagcagaa ggccatcctg     1020
acggatggcc ttttttgcgtt tctacaaact cttttttgctg cagagatctg cgggcagtga     1080
gcgcaacgca attaatgtga gttagctcac tcattaggca ccccaggctt tacactttat     1140
gcttccggct cgtataatgt gtggaattgt gagcggataa caatttcaca caggatctag     1200
aaataatttt gtttaacttt aagaaggaga tatacatatg aaaccagtaa cgttatacga     1260
tgtcgcagag tatgccggtg tctcttatca gaccgtttcc cgcgtggtga accaggccag     1320
ccacgtttct gcgaaaacgc gggaaaaagt ggaagcggcg atggcggagc tgaattacat     1380
tcccaaccgc gtggcacaac aactggcggg caaacagtcg ttgctgattg cgttgccac     1440 ctccagtctg gccctgcacg cgccgtcgca aattgtcgcg gcgattaaat ctcgcgccga     1500
tcaactgggt gccagcgtgg tggtgtcgat ggtagaacga agcggcgtcg aagcctgtaa     1560
agcggcggtg cacaatcttc tcgcgcaacg cgtcagtggg ctgatcatta actatccgct     1620
ggatgaccag gatgccattg ctgtggaagc tgcctgcact aatgttccgg cgttatttct     1680
tgatgtctct gaccagacac ccatcaacag tattattttc tcccatgaag acggtacgcg     1740
actgggcgtg gagcatctgg tcgcattggg tcaccagcaa atcgcgctgt tagcgggccc     1800
attaagttct gtctcggcgc gtctgcgtct ggctggctgg cataaatatc tcactcgcaa     1860
tcaaattcag ccgatagcgg aacgggaagg cgactgagt gccatgtccg ttttcaaca     1920 aaccatgcaa atgctgaatg agggcatcgt tcccactgcg atgctggttg ccaacgatca     1980
gatggcgctg ggcgcaatgc gcgccattac cgagtccggg ctgcgcgttg gtgcggatat     2040
ctcggtagtg ggatacgacg ataccgaaga cagctcatgt tatatcccgc cgttaaccac     2100
catcaaacag gattttcgcc tgctggggca accagcgtg gaccgcttgc tgcaactctc     2160
tcagggccag gcggtgaagg gcaatcagct gttgcccgtc tcactggtga aaagaaaaac     2220
caccctggcg cccaatacgc aaaccgcctc tccccgcgcg ttggccgatt cattaatgca     2280
gctggcacga caggtttccc gactggaaag cgggcagtga gcggatctcg atcccgcgaa     2340
attaatacga ctcactatag gggaattgtg agcggataac aattcccctc tagaaataat     2400 tttgttttaac tttaagaagg agatatacat atggctgact cgcaaccccct gtccggtgct     2460 ccggaaggtg ccgaatattt aagagcagtg ctgcgcgcgc cggtttacga ggcggcgcag     2520
gttacgccgc tacaaaaaat ggaaaaactg tcgtcgcgtc ttgataacgt cattctggtg     2580
aagcgcgaag atcgccagcc agtgcacagc tttaagctgc gcggcgcata cgccatgatg     2640
gcgggcctga cggaagaaca gaaagcgcac ggcgtgatca ctgcttctgc gggtaaccac     2700
gcgcagggcc tcgcgttttc ttctgcgcgg ttaggcgtga aggccctgat cgttatgcca     2760
accgccaccg ccgacatcaa agtcgacgcg gtgcgcggct tcggcggcga agtgctgctc     2820
aacggcgcga actttgatga agcgaaagcc aaagcgatcg aactgtcaca gcagcagggg     2880
ttcacctggg tgccgccgtt cgaccatccg atggtgattg ccgggcaagg cacgctggcg     2940
ctggaactgc tccagcagga cgcccatctc gaccgcgtat tgtgccagt cggcggcggc     3000 ggtctggctg ctggcgtggc ggtgctgatc aaacaactga tgccgcaaat caaagtgatc     3060
gccgtagaag cggaagactc cgcctgcctg aaagcagcgc tggatgcggg tcatccggtt     3120
gatctgccgc gcgtagggct attttgctgaa ggcgtagcgg taaaacgcat cggtgacgaa     3180
accttccgtt tatgccagga gtatctcgac gacatcatca ccgtcgatag cgatgcgatc     3240
tgtgcggcga tgaaggattt attcgaagat gtgcgcgcgg tggcggaacc ctctggcgcg     3300
```

```
ctggcgctgg cgggaatgaa aaaatatatc gccctgcaca acattcgcgg cgaacggctg    3360
gcgcatattc tttccggtgc caacgtgaac ttccacggcc tgcgctacgt ctcagaacgc    3420
tgcgaactgg gcgaacagcg tgaagcgttg ttggcggtga ccattccgga agaaaaaggc    3480
agcttcctca aattctgcca actgcttggc gggcgttcgg tcaccgagtt caactaccgt    3540
tttgccgatg ccaaaaacgc ctgcatcttt gtcggtgtgc gcctgagccg cggcctcgaa    3600
gagcgcaaag aaattttgca gatgctcaac gacggcggct acagcgtggt tgatctctcc    3660
gacgacgaaa tggcgaagct acacgtgcgc tatatggtcg gcggacgtcc atcgcatccg    3720
ttgcaggaac gcctctacag cttcgaattc ccggaatcac cgggcgcgct gctgcgcttc    3780
ctcaacacgc tgggtacgta ctggaacatt tctttgttcc actatcgcag ccatggcacc    3840
gactacgggc gcgtactggc ggcgttcgaa cttggcgacc atgaaccgga tttcgaaacc    3900
cggctgaatg agctgggcta cgattgccac gacgaaacca ataacccggc gttcaggttc    3960
tttttggcgg gttagggtcc gtcgacctgc agggggggggg gggaaagcca cgttgtgtct    4020
caaaatctct gatgttacat tgcacaagat aaaaatatat catcatgaac aataaaactg    4080
tctgcttaca taaacagtaa tacaaggggg gttatgagcc atattcaacg ggaaacgtct    4140
tgctcgaggc cgcgattaaa ttccaacatg gatgctgatt tatatgggta taaatgggct    4200
cgcgataatg tcgggcaatc aggtgcgaca atctatcgat tgtatgggaa gcccgatgcg    4260
ccagagttgt ttctgaaaca tggcaaaggt agcgttgcca atgatgttac agatgagatg    4320
gtcagactaa actggctgac ggaatttatg cctcttccga ccatcaagca ttttatccgt    4380
actcctgatg atgcatggtt actcaccact gcgatccccg ggaaaacagc attccaggta    4440
ttagaagaat atcctgattc aggtgaaaat attgttgatg cgctggcagt gttcctgcgc    4500
cggttgcatt cgattcctgt ttgtaattgt ccttttaaca gcgatcgcgt atttcgtctc    4560
gctcaggcgc aatcacgaat gaataacggt ttggttgatg cgagtgattt tgatgacgag    4620
cgtaatggct ggcctgttga acaagtctgg aaagaaatgc ataagctttt gccattctca    4680
ccggattcag tcgtcactca tggtgatttc tcacttgata accttatttt tgacgagggg    4740
aaattaatag gttgtattga tgttggacga gtcggaatcg cagaccgata ccaggatctt    4800
gccatcctat ggaactgcct cggtgagttt tctccttcat tacagaaacg gcttttttcaa    4860 aaatatggta ttgataatcc tgatatgaat aaattgcagt ttcatttgat gctcgatgag    4920
tttttctaat cagaattggt taattggttg taacactggc agagcattac gctgacttga    4980
cgggacggcg gctttgttga ataaatcgaa cttttgctga gttgaaggat cagatcacgc    5040
atcttcccga caacgcagac cgttccgtgg caaagcaaaa gttcaaaatc accaactggt    5100
ccacctacaa caaagctctc atcaaccgtg gctccctcac tttctggctg gatgatgggg    5160
cgattcaggc ctggtatgag tcagcaacac cttcttcacg aggcagacct tagggccccc    5220
ccccccctgc aggtcgacgg atccgaattc tagtagaggt cgaaattcac ctcgaaagca    5280
agctgataaa ccgatacaat taaaggctcc ttttggagcc tttttttttg gagattttca    5340
acgtgaaaaa attattattc gcaattccaa gctaattcac ctcgaaagca agctgataaa    5400
ccgatacaat taaaggctcc ttttggagcc tttttttttg gagattttca acgtgaaaaa    5460
attattattc gcaattccaa gctctgcctc gcgcgtttcg gtgatgacgg tgaaaacctc    5520
tgacacatgc agctcccgga gacggtcaca gcttgtctgt aagcggatgc cgggagcaga    5580
caagcccgtc agggcgcgtc agcgggtgtt ggcgggtgtc ggggcgcagc catgacccag    5640
```

```
tcacgtagcg atagcggagt gtatgggctc gatcccctcg cgagttggtt cagctgctgc    5700
ctgaggctgg acgacctcgc ggagttctac cggcagtgca atccgtcgg catccaggaa     5760 accagcagcg gctatccgcg catccatgcc cccgaacgat ccccatgtaa tgaataaaaa    5820
gcagtaatta atacatctgt ttcatttgaa gcgcgaaagc taaagtttcg catggatccc    5880
catgtaatga ataaaaagca gtaattaata catctgtttc atttgaagcg cgaaagctaa    5940
agttttcgca tttatcgtga aacgctttcg cgttttcgt gcgccgcttc a              5991
```

<210> SEQ ID NO 13
<211> LENGTH: 6758
<212> TYPE: DNA
<213> ORGANISM: Artificial Sequence
<220> FEATURE:
<223> OTHER INFORMATION: PL-SD1-ilvG*MEDA

<400> SEQUENCE: 13

```
tgcaagtgaa gttgagttgt tctggcggtg gaatgatgct cgcaaaaatg cagcggacaa      60
aggatgaact acgaggaagg gaacaacatt catacgctca agttagtata aaaaagcagg    120
cttcaagatc ttcacctacc aaacaatgcc ccctgcaaa aataaattc atataaaaaa     180 catacagata accatctgcg gtgataaatt atctctggcg gtgttgacat aaataccact    240
ggcggtgata ctgagcacat cagcaggacg cactgaccac catgaaggtg acgctcttaa    300
aaattaagcc ctgaagaagg gcagcattca agcagaagg cttggggtg tgtgatacga     360 aacgaagcat ggccggaag gagaactaac tatgaatggc gcacagtggg tggtacatgc     420
gttgcgggca cagggtgtga acaccgtttt cggttatccg ggtggcgcaa ttatgccggt    480
ttacgatgca ttgtatgacg gcggcgtgga gcacttgcta tgccgacatg agcagggtgc    540
ggcaatggcg gctatcggtt atgctcgtgc taccggcaaa actggcgtat gtatcgccac    600
gtctggtccg ggcgcaacca acctgataac cgggcttgcg gacgcactgt tagattccat    660
ccctgttgtt gccatcaccg gtcaagtgtc cgcaccgttt atcggcactg acgcatttca    720
ggaagtggat gtcctgggat gtcgttagc ctgtaccaag cacagctttc tggtgcagtc     780 gctgaagag ttgccgcgca tcatggctga agcattcgac gttgcctgct caggtcgtcc     840
tggtccggtt ctggtcgata tcccaaaaga tatccagtta gccagcggtg acctggaacc    900
gtggttcacc accgttgaaa acgaagtgac ttctccacat gccgaagttg agcaagcgcg    960
ccagatgctg gcaaaagcgc aaaaaccgat gctgtacgtt ggcggtggcg tgggtatggc    1020
gcaggcagtt ccggctttgc gtgaatttct cgctgccaca aaaatgcctg ccacctgtac    1080
gctgaaaggg ctgggcgcag tagaagcaga ttatccgtac tatctgggca tgctggggat    1140
gcacggcacc aaaagcggca acttcgcggt gcaggagtgt gacctgctga tcgccgtggg    1200
cgcacgtttt gatgaccggg tgaccggcaa actgaacacc ttcgcgccac acgccagtgt    1260
tatccatatg gatatcgacc cggcagaaat gaacaagctg cgtcaggcac atgtggcatt    1320
acaaggtgat ttaaatgctc tgttaccagc attacagcag ccgttaaatc aaaatgactg    1380
gcagcaacac tgcgcgcagc tgcgtgatga acattcctgg cgttacgacc atccggtgga    1440
cgctatctac gcgccgttgt tgttaaaaca actgtcggat cgtaaacctg cggattgcgt    1500
cgtgaccaca gatgtggggc agcaccagat gtgggctgcg cagcacatcg cccacactcg    1560
cccggaaaat ttcatcacct ccagcggttt aggtaccatg ggttttggtt taccggcggc    1620
ggttggcgca caagtcgcgc gaccgaacga taccgttgtc tgtatctccg gtgacggctc    1680
tttcatgatg aatgtgcaag agctgggcac cgtaaaacgc aagcagttac gttgaaaat   1740
```

```
cgtcttactc gataaccaac ggttagggat ggttcgacaa tggcagcaac tgttttttca    1800
ggaacgatac agcgaaacca cccttactga taaccccgat ttcctcatgt tagccagcgc    1860
cttcggcatc catggccaac acatcacccg gaaagaccag gttgaagcgg cactcgacac    1920
catgctgaac agtgatgggc atacctgct tcatgtctca atcgacgaac ttgagaacgt    1980
ctggccgctg gtgccgcctg cgccagtaa ttcagaaatg ttggagaaat tatcatgatg    2040
caacatcagg tcaatgtatc ggctcgcttc aatccagaaa ccttagaacg tgttttacgc    2100
gtggtgcgtc atcgtggttt ccacgtctgc tcaatgaata tggccgccgc cagcgatgca    2160
caaaatataa atatcgaatt gaccgttgcc agcccacggt cggtcgactt actgtttagt    2220
cagttaaata aactggtgga cgtcgcacac gttgccatct gccagagcac aaccacatca    2280
caacaaatcc gcgcctgagc gcaaaaggaa tataaaaatg accacgaaga aagctgatta    2340
catttggttc aatggggaga tggttcgctg gaagacgcg aaggtgcatg tgatgtcgca    2400
cgcgctgcac tatggcactt cggttttga aggcatccgt tgctacgact cgcacaaagg    2460
accggttgta ttccgccatc gtgagcatat gcagcgtctg catgactccg ccaaaatcta    2520
tcgcttcccg gtttcgcaga gcattgatga gctgatggaa gcttgtcgtg acgtgatccg    2580
caaaacaat ctcaccagcg cctatatccg tccgctgatc ttcgtcggtg atgttggcat    2640
gggagtaaac ccgccagcgg atactcaacc gacgtgatt atcgctgctt cccgtgggg    2700
agcgtatctg ggcgcagaag cgctggagca ggggatcgat gcgatggttt cctcctggaa    2760
ccgcgcacga ccaaacacca tcccgacggc ggcaaaagcc ggtggtaact acctctcttc    2820
cctgctggtg ggtagcgaag cgcgccgcca cggttatcag gaaggtatcg cgctggatgt    2880
gaacggttat atctctgaag cgcaggcga aaacctgttt gaagtgaaag atggtgtgct    2940
gttcacccca ccgttcacct cctccgcgct gccgggtatt acccgtgatg ccatcatcaa    3000
actggcgaaa gagctgggaa ttgaagtacg tgagcaggtg ctgtcgcgcg aatccctgta    3060
cctggcggat gaagtgttta tgtccggtac ggcggcagaa atcacgccag tgcgcagcgt    3120
agacggtatt caggttggcg aaggccgttg tggcccggtt accaaacgca ttcagcaagc    3180
cttcttcggc ctcttcactg gcgaaaccga agataaatgg ggctggttag atcaagttaa    3240
tcaataaata caaaaaatgg gacggcacgc accgtcccat ttacgagaca gacactggga    3300
gtaaataaag tatgcctaag taccgttccg ccaccaccac tcatggtcgt aatatggcgg    3360
gtgctcgtgc gctgtgggcc caccggaatg accgacgccg atttcggtaa gccgattatc    3420
gcggttgtga actcgttcac ccaatttgta ccgggtcacg tccatctgcg cgatctcggt    3480
aaactggtcg ccgaacaaat tgaagcggct ggcggcgttg ccaaagagtt caacaccatt    3540
gcggtggatg atgggattgc catgggccac gggggatgc tttattcact gccatctcgc    3600
gaactgatcg ctgattccgt tgagtatatg gtcaacgccc actgcgccga cgccatggtc    3660
tgcatctcta actgcgacaa aatcaccccg gggatgctga tggcttccct gcgcctgaat    3720
attccggtga tctttgtttc cggcggcccg atggaggccg ggaaaaccaa actttccgat    3780
cagatcatca agctcgatct ggttgatgcg atgatccagg cgcagaccc gaaagtatct    3840
gactcccaga gcgatcaggt tgaacgttcc gcgtgtccga cctgcggttc ctgctccggg    3900
atgtttaccg ctaactcaat gaactgcctg accgaagcgc tgggcctgtc gcagccgggc    3960
aacggctcgc tgctggcaac ccacgccgac cgtaagcagc tgttccttaa tgctggtaaa    4020
cgcattgttg aattgaccaa acgttattac gagcaaaacg acgaaagtgc actgccgcgt    4080
```

```
aatatcgcca gtaaggcggc gttttgaaaac gccatgacgc tggatatcgc gatgggtgga      4140
tcgactaaca ccgtacttca cctgctggcg gcggcgcagg aagcggaaat cgacttcacc      4200
atgagtgata tcgataagct ttcccgcaag gttccacagc tgtgtaaagt tgcgccgagc      4260
acccagaaat accatatgga agatgttcac cgtgctggtg gtgttatcgg tattctcggc      4320
gaactggatc gcgcggggtt actgaaccgt gatgtgaaaa acgtacttgg cctgacgttg      4380
ccgcaaacgc tggaacaata cgacgttatg ctgacccagg atgacgcggt aaaaaatatg      4440
ttccgcgcag gtcctgcagg cattcgtacc acacaggcat tctcgcaaga ttgccgttgg      4500
gatacgctgg acgacgatcg cgccaatggc tgtatccgct cgctggaaca cgcctacagc      4560
aaagacggcg gcctggcggt gctctacggt aactttgcgg aaaacggctg catcgtgaaa      4620
acggcaggcg tcgatgacag catcctcaaa ttcaccggcc cggcgaaagt gtacgaaagc      4680
caggacgatg cggtagaagc gattctcggc ggtaaagttg tcgccggaga tgtggtagta      4740
attcgctatg aaggcccgaa aggcggtccg gggatgcagg aaatgctcta cccaaccagc      4800
ttcctgaaat caatgggtct cggcaaagcc tgtgcgctga tcaccgacgg tcgtttctct      4860
ggtggcacct ctggtctttc catcggccac gtctcaccgg aagcggcaag cggcggcagc      4920
attggcctga ttgaagatgg tgacctgatc gctatcgaca tcccgaaccg tggcattcag      4980
ttacaggtaa gcgatgccga actggcggcg cgtcgtgaag cgcaggacgc tcgaggtgac      5040
aaagcctgga cgccgaaaaa tcgtgaacgt caggtctcct tgccctgcg tgcttatgcc       5100 agcctggcaa ccagcgccga caaaggcgcg gtgcgcgata aatcgaaact gggggggttaa      5160 taatggctga ctcgcaaccc ctgtccggtg ctccggaagg tgccgaatat ttaagagcag      5220
tgctgcgcgc gccggtttac gaggcggcgc aggttacgcc gctacaaaaa atggaaaaac      5280
tgtcgtcgcg tcttgataac gtcattctgg tgaagcgcga agatcgccag ccagtgcaca      5340
gctttaagct gcgcggcgca tacgccatga tggcgggcct gacggaagaa cagaaagcgc      5400
acggcgtgat cactgcttct gcgggtaacc acgcgcaggg cgtcgcgttt tcttctgcgc      5460
ggttaggcgt gaaggccctg atcgttatgc caaccgccac cgccgacatc aaagtcgacg      5520
cggtgcgcgc cttcggcggc gaagtgctgc tccacgcgc gaactttgat gaagcgaaag      5580
ccaaagcgat cgaactgtca cagcagcagg ggttcacctg ggtgccgccg ttcgaccatc      5640
cgatggtgat tgccgggcaa ggcacgctgg cgctggaact gctccagcag gacgcccatc      5700
tcgaccgcgt atttgtgcca gtcggcggcg gcggtctggc tgctggcgtg gcggtgctga      5760
tcaaacaact gatgccgcaa atcaaagtga tcgccgtaga agcggaagac tccgcctgcc      5820
tgaaagcagc gctggatgcg ggtcatccgg ttgatctgcc gcgcgtaggg ctatttgctg      5880
aaggcgtagc ggtaaaacgc atcggtgacg aaaccttccg tttatgccag gagtatctcg      5940
acgacatcat caccgtcgat agcgatgcga tctgtgcggc gatgaaggat ttattcgaag      6000
atgtgcgcgc ggtggcggaa ccctctggcg cgctggcgct ggcgggaatg aaaaaatata      6060
tcgccctgca caacattcgc ggcgaacggc tggcgcatat tctttccggt gccaacgtga      6120
acttccacgg cctgcgctac gtctcagaac gctgcgaact gggcgaacag cgtgaagcgt      6180
tgttggcggt gaccattccg gaagaaaaag gcagcttcct caaattctgc caactgcttg      6240
gcgggcgttc ggtcaccgag ttcaactacc gttttgccga tgccaaaaac gcctgcatct      6300
ttgtcggtgt gcgcctgagc cgcggcctcg aagagcgcaa agaaattttg cagatgctca      6360 acgacggcg ctcagcgtg gttgatctct ccgacgacga aatggcgaag ctacacgtgc      6420
gctatatggt cggcggacgt ccatcgcatc cgttgcagga acgcctctac agcttcgaat      6480
```

```
tcccggaatc accgggcgcg ctgctgcgct tcctcaacac gctgggtacg tactggaaca    6540
tttctttgtt ccactatcgc agccatggca ccgactacgg gcgcgtactg gcggcgttcg    6600
aacttggcga ccatgaaccg gatttcgaaa cccggctgaa tgagctgggc tacgattgcc    6660
acgacgaaac caataacccg gcgttcaggt tcttttttggc gggttaggga aaaatgcctg    6720
atagcgcttc gcttatcagg cctacccgcg cgacaacg                            6758
```

<210> SEQ ID NO 14
<211> LENGTH: 6498
<212> TYPE: DNA
<213> ORGANISM: Artificial Sequence
<220> FEATURE:
<223> OTHER INFORMATION: dacA::mini-Mu::cat-Pthr-attB-thrA*BC

<400> SEQUENCE: 14

```
agcttttcat tctgactgca acgggcaata tgtctctgtg tggattaaaa aaagagtgtc     60
tgatagcagc ttctgaactg gttacctgcc gtgagtaaat taaaatttta ttgacttagg    120
tcactaaata ctttaaccaa tataggcata gcgcacagac agataaagac tctagagtcc    180
gaccaaaggt aacgaggtaa caaccatgcg agtgttgaag ttcggcggta catcagtggc    240
aaatgcagaa cgttttctgc gtgttgccga tattctggaa agcaatgcca ggcaggggca    300
ggtggccacc gtcctctctg cccccgccaa aatcaccaac cacctggtgg cgatgattga    360
aaaaaccatt agcggccagg atgctttacc caatatcagc gatgccgaac gtattttgc     420 cgaacttttg acgggactcg ccgccgccca gccggggttc cgctggcgc aattgaaaac    480 tttcgtcgat caggaatttg cccaaataaa acatgtcctg catggcatta gtttgttggg    540
gcagtgcccg gatagcatca acgctgcgct gatttgccgt ggcgagaaaa tgtcgatcgc    600
cattatggcc ggcgtattag aagcgcgcgg tcacaacgtt actgttatcg atccggtcga    660
aaaactgctg gcagtggggc attacctcga atctaccgtc gatattgctg agtccacccg    720
ccgtattgcg gcaagccgca ttccggctga tcacatggtg ctgatggcag gtttcaccgc    780
cggtaatgaa aaaggcgaac tggtggtgct tggacgcaac ggttccgact actctgctgc    840
ggtgctggct gcctgtttac gcccgattg ttgcagatt tggacggacg ttgacggggt    900
ctatacctgc gacccgcgtc aggtgcccga tgcgaggttg ttgaagtcga tgtcctacca    960
ggaagcgatg gagctttcct acttcggcgc taaagttctt caccccccgca ccattacccc   1020 catcgcccag ttccagatcc cttgcctgat aaaaatacc ggaaatcctc aagcaccagg    1080
tacgctcatt ggtgccagcc gtgatgaaga cgaattaccg gtcaagggca tttccaatct    1140
gaataacatg gcaatgttca gcgtttctgg tccggggatg aaagggatgg tcggcatggc    1200
ggcgcgcgtc tttgcagcga tgtcacgcgc ccgtatttcc gtggtgctga ttacgcaatc    1260
atcttccgaa tacagcatca gtttctgcgt tccacaaagc gactgtgtgc gagctgaacg    1320
ggcaatgcag gaagagttct acctggaact gaaagaaggc ttactggagc cgctggcagt    1380
gacggaacgg ctggccatta tctcggtggt aggtgatggt atgcgcacct tgcgtgggat    1440
ctcggcgaaa ttctttgccg cactggcccg cgccaatatc aacattgtcg ccattgctca    1500
gagatcttct gaacgctcaa tctctgtcgt ggtaaataac gatgatgcga ccactggcgt    1560
gcgcgttact catcagatgc tgttcaatac cgatcaggtt atcgaagtgt ttgtgattgg    1620
cgtcggtggc gttggcggtg cgctgctgga gcaactgaag cgtcagcaaa gctggctgaa    1680
gaataaacat atcgacttac gtgtctgcgg tgttgccaac tcgaaggctc tgctcaccaa    1740
```

```
tgtacatggc cttaatctgg aaaactggca ggaagaactg gcgcaagcca aagagccgtt   1800
taatctcggg cgcttaattc gcctcgtgaa agaatatcat ctgctgaacc cggtcattgt   1860
tgactgcact tccagccagg cagtggcgga tcaatatgcc gacttcctgc gcgaaggttt   1920
ccacgttgtc acgccgaaca aaaaggccaa cacctcgtcg atggattact accatcagtt   1980
gcgttatgcg gcggaaaaat cgcggcgtaa attcctctat gacaccaacg ttggggctgg   2040
attaccggtt attgagaacc tgcaaaatct gctcaatgca ggtgatgaat tgatgaagtt   2100
ctccggcatt ctttctggtt cgcttttctta tatcttcggc aagttagacg aaggcatgag   2160
tttctccgag cgaccacgc tggcgcggga atgggttat accgaaccgg acccgcgaga     2220
tgatcttcct ggtatggatg tggcgcgtaa actattgatt ctcgctcgtg aaacgggacg    2280
tgaactggag ctggcggata ttgaaattga acctgtgctg cccgcagagt ttaacgccga    2340
gggtgatgtt gccgctttta tggcgaatct gtcacaactc gacgatctct ttgccgcgcg    2400
cgtggcgaag gcccgtgatg aaggaaaagt tttgcgctat gttggcaata ttgatgaaga    2460
tggcgtctgc cgcgtgaaga ttgccgaagt ggatggtaat gatccgctgt tcaaagtgaa    2520
aaatggcgaa aacgccctgg ccttctatag ccactattat cagccgctgc cgttggtact    2580
gcgcggatat ggtgcgggca atgacgttac agctgccggt gtctttgctg atctgctacg    2640
taccctctca tggaagttag gagtctgaca tggttaaagt ttatgccccg gcttccagtg    2700
ccaatatgag cgtcgggttt gatgtgctcg ggcggcggt gacacctgtt gatggtgcat     2760
tgctcggaga tgtagtcacg gttgaggcgg cagagacatt cagtctcaac aacctcggac    2820
gctttgccga taagctgccg tcagaaccac gggaaaatat cgtttatcag tgctgggagc    2880
gtttttgcca ggaactgggt aagcaaattc cagtggcgat gaccctggaa agaatatgc    2940
cgatcggttc gggcttaggc tccagtgcct gttcggtggt cgcggcgctg atggcgatga    3000
atgaacactg cggcaagccg cttaatgaca ctcgtttgct ggctttgatg ggcgagctgg    3060
aaggccgtat ctccggcagc attcattacg acaacgtggc accgtgtttt tcggtggta    3120
tgcagttgat gatcgaagaa acgacatca tcagccagca agtgccaggg tttgatgagt    3180
ggctgtgggt gctggcgtat ccggggatta aagtctcgac ggcagaagcc agggctattt    3240
taccggcgca gtatcgccgc caggattgca ttgcgcacgg gcgacatctg gcaggcttca    3300
ttcacgcctg ctattcccgt cagcctgagc ttgccgcgaa gctgatgaaa gatgttatcg    3360
ctgaacccta ccgtgaacgg ttactgccag gcttccggca ggcgcggcag gcggtcgcgg    3420
aaatcggcgc ggtagcgagc ggtatctccg gctccggccc gaccttgttc gctctgtgtg    3480
acaagccgga aaccgcccag cgcgttgccg actggttggg taagaactac ctgcaaaatc    3540
aggaaggttt tgttcatatt tgccggctgg atacggcggg cgcacgagta ctggaaaact    3600
aaatgaaact ctacaatctg aaagatcaca acgagcaggt cagctttgcg caagccgtaa    3660
cccaggggtt gggcaaaaat caggggctgt tttttccgca cgacctgccg gaattcagcc    3720
tgactgaaat tgatgagatg ctgaagctgg attttgtcac ccgcagtgcg aagatcctct    3780
cggcgtttat tggtgatgaa atcccacagg aaatcctgga agagcgcgtg cgcgcggcgt    3840
ttgccttccc ggctccggtc gccaatgttg aaagcgatgt cggttgtctg gaattgttcc    3900
acgggccaac gctggcattt aaagatttcg gcggtcgctt tatggcacaa atgctgaccc    3960
atattgcggg tgataagcca gtgaccattc tgaccgcgac ctccggtgat accggagcgg    4020
cagtggctca tgctttctac ggtttaccga atgtgaaagt ggttatcctc tatccacgag    4080
gcaaaatcag tccactgcaa gaaaaactgt tctgtacatt gggcggcaat atcgaaactg    4140
```

-continued

```
ttgccatcga cggcgatttc gatgcctgtc aggcgctggt gaagcaggcg tttgatgatg    4200
aagaactgaa agtggcgcta gggttaaact cggctaactc gattaacatc agccgtttgc    4260
tggcgcagat ttgctactac tttgaagctg ttgcgcagct gccgcaggag acgcgcaacc    4320
agctggttgt ctcggtgcca agcggaaact tcggcgattt gacggcgggt ctgctggcga    4380
agtcactcgg tctgccggtg aaacgttttta ttgctgcgac caacgtgaac gataccgtgc    4440
cacgtttcct gcacgacggt cagtggtcac ccaaagcgac tcaggcgacg ttatccaacg    4500
cgatggacgt gagtcagccg aacaactggc cgcgtgtgga agagttgttc cgccgcaaaa    4560
tctggcaact gaaagagctg ggttatgcag ccgtggatga tgaaaccacg caacagacaa    4620
tgcgtgagtt aaaagaactg gctacacttc ggagccgca cgctgccgta gcttatcgtg     4680
cgctgcgtga tcagttgaat ccaggcgaat atggcttgtt cctcggcacc gcgcatccgg    4740
cgaaatttaa agagagcgtg gaagcgattc tcggtgaaac gttggatctg ccaaaagagc    4800
tggcagaacg tgctgattta cccttgcttt cacataatct gcccgccgat tttgctgcgt    4860
tgcgtaaatt gatgatgaat catcagtaaa atctattcat tatctcaatc aggccgggtt    4920
tgcttttatg cagcccggct ttttatgaa gaaattatgg agaaaaatga cagggaaaaa    4980
ggagaaattc tcaataaatg cggtaactta gagattagga ttgcggagaa taacaaccgc    5040
cgttctcatc gagtaatctc ggatatcgac cataacggga atgataaaag gagtaacctg    5100
tgaaaaagat gcaatctatc gtactcgcac tttccctggt tctggtcgct cccatggcag    5160
cacaggctgc ggaaattacg ttagtcccgt cagtaaaatt acagataggc gatcgtgata    5220
atcgtggcta ttactgggat ggaggtcact ggcgcgacca cggctggtgg aaacaacatt    5280
atgaatggcg aggcaatcgc tggcacctac acggaccgcc gccaccgccg cgccaccata    5340
agaaagctcc tcatgatcat cacggcggtc atggtcctgg caaacatcac cgctaaatga    5400
caaatgccgg gtaacaatcc ggcattcagc gcctgatgcg acgctggcgc gtcttatcag    5460
gcctacgtta attctgcaat atattgaatc tgcatgcttt tgtaggcagg ataaggcgtt    5520
cacgccgcat ccggcattga ctgcaaactt aacgctgctc gtagcgttta aacaccagtt    5580
cgccattgct ggaggaatct tcatcaaaga agtaaccttc gctattaaaa ccagtcagtt    5640
gctctggttt ggtcagccga ttttcaataa tgaaacgact catcagaccg cgtgctttct    5700
tagcgtagaa gctgatgatc ttaaatttgc cgttcttctc atcgaggaac accggcttga    5760
taatctcggc attcaatttc ttcggcttca ccgatttaaa atactcatct gacgccagat    5820
taatcaccac attatcgcct tgtgctgcga gcgcctcgtt cagcttgttg gtgatgatat    5880
ctccccagaa ttgatacaga tcttccctc gggcattctc aagacggatc cccgggtacc    5940
gagctcggta cccggggatc tctagagtc gaaattcacc tcgaaagcaa gctgataaac    6000
cgatacaatt aaaggctcct tttggagcct ttttttttgg agattttcaa cgtgaaaaaa    6060
ttattattcg caattcaagc taattcacct cgaaagcaag ctgataaacc gatcaatta     6120 aaggctcctt ttggagcctt ttttttgga gattttcaac gtgaaaaaat tattattcgc     6180
aattctgcct cgcgcgtttc ggtgatgacg gtgaaaacct ctgacacatg cagctcccgg    6240
agacggtcac agcttgtctg taagcggatg ccggagcag acaagcccgt cagggcgcgt     6300
cagcgggtgt tggcgggtgt cggggcgcag ccatgaccca gtcacgtagc gatagcggag    6360
tgtatgggct cgatccctc ggatccccat gtaatgaata aaaagcagta attaatacat     6420
ctgtttcatt tgaagcgcga aagctaaagt tttcgcattt atcgtgaaac gctttcgcgt    6480
```

```
ttttcgtgcg ccgcttca                                              6498

<210> SEQ ID NO 15
<211> LENGTH: 21
<212> TYPE: DNA
<213> ORGANISM: Artificial Sequence
<220> FEATURE:
<223> OTHER INFORMATION: Primer P1

<400> SEQUENCE: 15
atacaaaacg gcatctccgt g                                            21

<210> SEQ ID NO 16
<211> LENGTH: 20
<212> TYPE: DNA
<213> ORGANISM: Artificial Sequence
<220> FEATURE:
<223> OTHER INFORMATION: Primer P2

<400> SEQUENCE: 16
ctgcctggca ttgctttcca                                              20

<210> SEQ ID NO 17
<211> LENGTH: 1256
<212> TYPE: DNA
<213> ORGANISM: Artificial Sequence
<220> FEATURE:
<223> OTHER INFORMATION: DNA fragment 1

<400> SEQUENCE: 17
atacaaaacg gcatctccgt ggagaatgag taaaagtggg ggaaaagtat atcacagcga    60
ggagagggga gttacccgac caggagccgg gtaacggaga agcgagttac agaaccatgc   120
ggacaatatc gattttgccc agttcttcat acagtgtttc aacctgctcg atatgagtgg   180
cgttgatagt gatagatacc gagtggtagt tgcctttgct gcttggtttt accgttgggg   240
tgtagtcacc tggcgcatgg cgctgtacca cttcaaccac ctgatcaacc agctcaggta   300
acgcctgccc cataactttg taagtaaaag gagtagggaa ttcaagcagt tcgttaagtt   360
tggttttcat gtcagctccg gcgtaacgta attaaatagc aactcccgcc agaaggcggg   420
agttttttac tgatgcttag tatatgggga cggaaattac actttcaagt gtttaatttt   480
taaccaaacc agtgatggaa cattaattta atgtaatgta ttgattcact tgaagtacga   540 aaaaaccgg gaggacattg gattattcgg gatctgatgg gattagattt ggtggggctt   600
gcaagcctgt agtgcaaatt ttagtcgtta atcaatgaaa cgcgaaagat agtaaaaaat   660
tgcttttgtt tcattgaaaa tacgaaaaac aaaaacactg caaatcattt caataacagc   720
ttcaaaaaac gttcaaaacc gataacaacc aagctgtcac caaatgactc atatcacaaa   780
tcagcttatg ccgtttaggt atgttacatg tgtgattatg tgaggtgaag tatgttttag   840
ctggttcatg gttgttatac ggctttttt acctcctgtg gttcctgtga aggtactaca   900
acactttcct gttcatgaat cccatacttt gacaaaatct ctttgcgttt ttcttcaggt   960
aagcttttca ttctgactgc aacgggcaat atgtctctgt gtggattaaa aaaagagtgt  1020
ctgatagcag cttctgaact ggttacctgc cgtgagtaaa ttaaattttt attgacttag  1080
gtcactaaat actttaacca atataggcat agcgcacaga cagataaaga ctctagagtc  1140
cgaccaaagg taacgaggta acaaccatgc gagtgttgaa gttcggcggt acatcagtgg  1200
caaatgcaga acgttttctg cgtgttgccg atattctgga aagcaatgcc aggcag      1256
```

<210> SEQ ID NO 18
<211> LENGTH: 2452
<212> TYPE: DNA
<213> ORGANISM: Artificial Sequence
<220> FEATURE:
<223> OTHER INFORMATION: DNA fragment 2

<400> SEQUENCE: 18

| | | | | | |
|---|---|---|---|---|---|
| atacaaaacg | gcatctccgt | ggagaatgag | taaaagtggg | ggaaaagtat atcacagcga | 60 |
| ggagagggga | gttacccgac | caggagccgg | gtaacggaga | agcgagttac agaaccatgc | 120 |
| ggacaatatc | gatttttgccc | agttcttcat | acagtgtttc | aacctgctcg atatgagtgg | 180 |
| cgttgatagt | gatagatacc | gagtggtagt | tgcctttgct | gcttggtttt accgttgggg | 240 |
| tgtagtcacc | tggcgcatgg | cgctgtacca | cttcaaccac | ctgatcaacc agctcaggta | 300 |
| acgcctgccc | cataactttg | taagtaaaag | gagtagggaa | ttcaagcagt tcgttaagtt | 360 |
| tggttttcat | gtcagctccg | gcgtaacgta | attaaatagc | aactcccgcc agaaggcggg | 420 |
| agttttttac | tgatgcttag | tatatgggga | cggaaattac | actttcaagt gtttaattttt | 480 |
| taaccaaacc | agtgatggaa | cattaattta | atgtaatgaa | gcctgctttt ttatactaag | 540 |
| ttggcattat | aaaaaagcat | tgcttatcaa | tttgttgcaa | cgaacaggtc actatcagtc | 600 |
| aaaataaaat | cattatttga | tttcgaattc | tcatgtttga | cagcttatca tcgataagct | 660 |
| ttaatgcggt | agtttatcac | agttaaattg | ctaacgcagt | caggcaccgt gtatgaaatc | 720 |
| taacaatgcg | ctcatcgtca | tcctcggcac | cgtcaccctg | gatgctgtag gcataggctt | 780 |
| ggttatgccg | gtactgccgg | gcctcttgcg | ggatatcgtc | cattccgaca gcatcgccag | 840 |
| tcactatggc | gtgctgctag | cgctatatgc | gttgatgcaa | tttctatgcg cacccgttct | 900 |
| cggagcactg | tccgaccgct | ttggccgccg | cccagtcctg | ctcgcttcgc tacttggagc | 960 |
| cactatcgac | tacgcgatca | tggcgaccac | acccgtcctg | tggatctccg gataagtaga | 1020 |
| cagcctgata | gtcgcacga | aaaacaggta | ttgacaacat | gaagtaacat gcagtaagat | 1080 |
| acaaatcgct | aggtaacact | agcagcgtca | accgggcgct | ctagctagag ccaagctagc | 1140 |
| ttggccggat | ccgagatttt | caggagctaa | ggaagctaaa | atggagaaaa aaatcactgg | 1200 |
| atataccacc | gttgatatat | cccaatggca | tcgtaaagaa | catttttgagg catttcagtc | 1260 |
| agttgctcaa | tgtacctata | accagaccgt | tcagctggat | attacggcct ttttaaagac | 1320 |
| cgtaaagaaa | aataagcaca | agttttatcc | ggcctttatt | cacattcttg cccgcctgat | 1380 |
| gaatgctcat | ccggaattcc | gtatggcaat | gaaagacggt | gagctggtga tatgggatag | 1440 |
| tgttcacccct | tgttacaccg | ttttccatga | gcaaactgaa | acgttttcat cgctctggag | 1500 |
| tgaataccac | gacgatttcc | ggcagtttct | acacatatat | tcgcaagatg tggcgtgtta | 1560 |
| cggtgaaaac | ctggcctatt | tccctaaagg | gtttattgag | aatatgtttt tcgtctcagc | 1620 |
| caatccctgg | gtgagtttca | ccagttttga | tttaaacgtg | gccaatatgg acaacttctt | 1680 |
| cgcccccgtt | ttcaccatgg | gcaaatatta | tacgcaaggc | gacaaggtgc tgatgccgct | 1740 |
| ggcgattcag | gttcatcatg | ccgtctgtga | tggcttccat | gtcggcagaa tgcttaatga | 1800 |
| attacaacag | tactgcgatg | agtggcaggg | cggggcgtaa | ttttttttaag gcagttattg | 1860 |
| gtgcccttaa | acgcctggtg | ctacgcctga | ataagtgata | ataagcggat gaatggcaga | 1920 |
| aattcgtcga | agcttaacac | agaaaaaagc | ccgcacctga | cagtgcgggc ttttttttttc | 1980 |
| gaccactgca | gtctgttaca | ggtcactaat | accatctaag | tagttgattc atagtgactg | 2040 |
| catatgttgt | gttttacagt | attatgtagt | ctgttttttta | tgcaaaatct aatttaatat | 2100 |

| | |
|---|---|
| attgatattt atatcatttt acgtttctcg ttcagctttt ttatactaac ttgagcgagc | 2160 |
| ttttcattct gactgcaacg ggcaatatgt ctctgtgtgg attaaaaaaa gagtgtctga | 2220 |
| tagcagcttc tgaactggtt acctgccgtg agtaaattaa aattttattg acttaggtca | 2280 |
| ctaaatactt taaccaatat aggcatagcg cacagacaga taaagactct agagtccgac | 2340 |
| caaaggtaac gaggtaacaa ccatgcgagt gttgaagttc ggcggtacat cagtggcaaa | 2400 |
| tgcagaacgt tttctgcgtg ttgccgatat tctggaaagc aatgccaggc ag | 2452 |

<210> SEQ ID NO 19
<211> LENGTH: 842
<212> TYPE: DNA
<213> ORGANISM: Artificial Sequence
<220> FEATURE:
<223> OTHER INFORMATION: DNA fragment 3

<400> SEQUENCE: 19

| | |
|---|---|
| atacaaaacg gcatctccgt ggagaatgag taaaagtggg ggaaaagtat atcacagcga | 60 |
| ggagagggga gttacccgac caggagccgga gtaacgagaa agcgagttac agaaccatgc | 120 |
| ggacaatatc gattttgccc agttcttcat acagtgtttc aacctgctcg atatgagtgg | 180 |
| cgttgatagt gatagatacc gagtggtagt tgcctttgct gcttggtttt accgttgggg | 240 |
| tgtagtcacc tggcgcatgg cgctgtacca cttcaaccac ctgatcaacc agctcaggta | 300 |
| acgcctgccc cataactttg taagtaaaag gagtagggaa ttcaagcagt tcgttaagtt | 360 |
| tggttttcat gtcagctccg gcgtaacgta attaaatagc aactcccgcc agaaggcggg | 420 |
| agttttttac tgatgcttag tatatgggga cggaaattac actttcaagt gtttaatttt | 480 |
| taaccaaacc agtgatggaa cattaattta atgtaatgaa gcctgctttt ttatactaac | 540 |
| ttgagcgagc ttttcattct gactgcaacg ggcaatatgt ctctgtgtgg attaaaaaaa | 600 |
| gagtgtctga tagcagcttc tgaactggtt acctgccgtg agtaaattaa aattttattg | 660 |
| acttaggtca ctaaatactt taaccaatat aggcatagcg cacagacaga taaagactct | 720 |
| agagtccgac caaaggtaac gaggtaacaa ccatgcgagt gttgaagttc ggcggtacat | 780 |
| cagtggcaaa tgcagaacgt tttctgcgtg ttgccgatat tctggaaagc aatgccaggc | 840 |
| ag | 842 |

<210> SEQ ID NO 20
<211> LENGTH: 3539
<212> TYPE: DNA
<213> ORGANISM: Artificial Sequence
<220> FEATURE:
<223> OTHER INFORMATION: cynX::cat-PL-ilvA*

<400> SEQUENCE: 20

| | |
|---|---|
| tgcaccagta cgttttccgc agctgtgggt caaagacgct caagttagta taaaaaagct | 60 |
| gaacgagaaa cgtaaaatga tataaatatc aatatattaa attagatttt gcataaaaaa | 120 |
| cagactacat aatactgtaa aacacaacat atgcagtcac tatgaatcaa ctacttagat | 180 |
| ggtattagtg acctgtaaca gactgcagtg gtcgaaaaaa aaagcccgca ctgtcaggtg | 240 |
| cgggcttttt tctgtgttaa gcttcgacga atttctgcca ttcatccgct tattatcact | 300 |
| tattcaggcg tagcaccagg cgtttaaggg caccaataac tgccttaaaa aaattacgcc | 360 |
| ccgccctgcc actcatcgca gtactgttgt aattcattaa gcattctgcc gacatggaag | 420 |
| ccatcacaga cggcatgatg aacctgaatc gccagcggca tcagcacctt gtcgccttgc | 480 |
| gtataatatt tgcccatggt gaaaacgggg gcgaagaagt tgtccatatt ggccacgttt | 540 |

```
aaatcaaaac tggtgaaact cacccaggga ttggctgaga cgaaaaacat attctcaata    600 aacccttttag ggaaataggc caggttttca ccgtaacacg ccacatcttg cgaatatatg   660
tgtagaaact gccggaaatc gtcgtggtat tcactccaga gcgatgaaaa cgtttcagtt   720
tgctcatgga aaacggtgta acaagggtga acactatccc atatcaccag ctcaccgtct   780
ttcattgcca tacggaattc cggatgagca ttcatcaggc gggcaagaat gtgaataaag   840
gccggataaa acttgtgctt attttttcttt acggtcttta aaaaggccgt aatatccagc   900
tgaacggtct ggttataggt acattgagca actgactgaa atgcctcaaa atgttcttta   960
cgatgccatt gggatatatc aacggtggta tatccagtga ttttttttctc cattttagct  1020 tccttagctc ctgaaaatct cggatccgat atctagctag agcgcccggt tgacgctgct  1080
agtgttacct agcgatttgt atcttactgc atgttacttc atgttgtcaa tacctgttt   1140 tcgtgcgact tatcaggctg tctacttatc cggagatcca caggacgggt gtggtcgcca  1200
tgatcgcgta gtcgatagtg gctccaagta gcgaagcgag caggactggg cggcggccaa  1260
agcggtcgga cagtgctccg agaacgggtg cgcatagaaa ttgcatcaac gcatatagcg  1320
ctagcagcac gccatagtga ctggcgatgc tgtcggaatg gacgatatcc cgcaagaggc  1380
ccggcagtac cggcataacc aagcctatgc ctacagcatc cagggtgacg gtgccgagga  1440
tgacgatgag cgcattgtta gatttcatac acggtgcctg actgcgttag caatttaact  1500
gtgataaact accgcattaa agcttatcga tgataagctg tcaaacatga gaattcgaaa  1560
tcaaataatg attttatttt gactgatagt gacctgttcg ttgcaacaaa ttgataagca  1620
atgctttttt ataatgccaa cttagtataa aaaagcaggc ttcaagatct tcacctacca  1680
aacaatgccc ccctgcaaaa aataaattca tataaaaaac atacagataa ccatctgcgg  1740
tgataaatta tctctggcgg tgttgacata aataccactg gcggtgatac tgagcacatc  1800
agcaggacgc actgaccacc atgaaggtga cgctcttaaa aattaagccc tgaagaaggg  1860
cagcattcaa agcagaaggc tttggggtgt gtgatacgaa acgaagcatt ggccggaagg  1920
agaactaact atggctgact cgcaacccct gtccggtgct ccggaaggtg ccgaatattt  1980
aagagcagtg ctgcgcgcgc cggtttacga ggcggcgcag gttacgccgc tacaaaaaat  2040
ggaaaaactg tcgtcgcgtc ttgataacgt cattctggtg aagcgcgaag atcgccagcc  2100
agtgcacagc tttaagctgc gcggcgcata cgccatgatg gcgggcctga cggaagaaca  2160
gaaagcgcac ggcgtgatca ctgcttctgc gggtaaccac gcgcagggcg tcgcgttttc  2220
ttctgcgcgg ttaggcgtga aggccctgat cgttatgcca accgccaccg ccgacatcaa  2280
agtcgacgcg gtgcgcggct tcggcggcga agtgctgctc cacggcgcga actttgatga  2340
agcgaaagcc aaagcgatcg aactgtcaca gcagcagggg ttcacctggg tgccgccgtt  2400
cgaccatccg atggtgattg ccgggcaagg cacgctggcg ctggaactgc tccagcagga  2460
cgcccatctc gaccgcgtat tgtgccagt cggcggcggc ggtctggctg ctggcgtggc  2520
ggtgctgatc aaacaactga tgccgcaaat caaagtgatc gccgtagaag cggaagactc  2580
cgcctgcctg aaagcagcgc tggatgcggg tcatccggtt gatctgccgc gcgtagggct  2640
atttgctgaa ggcgtagcgg taaaacgcat cggtgacgaa accttccgtt tatgccagga  2700
gtatctcgac gacatcatca ccgtcgatag cgatgcgatc tgtgcggcga tgaaggattt  2760
attcgaagat gtgcgcgcgg tggcggaacc ctctggcgcg ctggcgctgg cgggaatgaa  2820
aaaatatatc gccctgcaca acattcgcgg cgaacggctg cgcatattc tttccggtgc  2880
```

-continued

| | |
|---|---|
| caacgtgaac ttccacggcc tgcgctacgt ctcagaacgc tgcgaactgg gcgaacagcg | 2940 |
| tgaagcgttg ttggcggtga ccattccgga agaaaaaggc agcttcctca aattctgcca | 3000 |
| actgcttggc gggcgttcgg tcaccgagtt caactaccgt tttgccgatg ccaaaaacgc | 3060 |
| ctgcatcttt gtcggtgtgc gcctgagccg cggcctcgaa gagcgcaaag aaattttgca | 3120 |
| gatgctcaac gacggcggct acagcgtggt tgatctctcc gacgacaaaa tggcgaagct | 3180 |
| acacgtgcgc tatatggtcg gcggacgtcc atcgcatccg ttgcaggaac gcctctacag | 3240 |
| cttcgaattc ccggaatcac cgggcgcgct gctgcgcttc ctcaacacgc tgggtacgta | 3300 |
| ctggaacatt tctttgttcc actatcgcag ccatggcacc gactacgggc gcgtactggc | 3360 |
| ggcgttcgaa cttggcgacc atgaaccgga tttcgaaacc cggctgaatg agctgggcta | 3420 |
| cgattgccac gacgaaacca ataacccggc gttcaggttc tttttggcgg ttagggaaa | 3480 |
| aatgcctgat agcgcttcgc ttaggcatga tgcgacgctt gttcctgcgc tttgttcat | 3539 |

<210> SEQ ID NO 21
<211> LENGTH: 20
<212> TYPE: DNA
<213> ORGANISM: Artificial Sequence
<220> FEATURE:
<223> OTHER INFORMATION: Primer 3

<400> SEQUENCE: 21

| | |
|---|---|
| aagctggtgg cgtttatgca | 20 |

<210> SEQ ID NO 22
<211> LENGTH: 20
<212> TYPE: DNA
<213> ORGANISM: Artificial Sequence
<220> FEATURE:
<223> OTHER INFORMATION: Primer 4

<400> SEQUENCE: 22

| | |
|---|---|
| attcggcacc ttccggagca | 20 |

<210> SEQ ID NO 23
<211> LENGTH: 2131
<212> TYPE: DNA
<213> ORGANISM: Artificial Sequence
<220> FEATURE:
<223> OTHER INFORMATION: DNA fragment 4

<400> SEQUENCE: 23

| | |
|---|---|
| aagctggtgg cgtttatgca gggaatcggt tttatcatcg ccgggcttgc cccgtggttt | 60 |
| tctggcgtgc tgcgtagtat cagcggcaat tacctgatgg actgggcatt tcatgcgctg | 120 |
| tgcgtcgttg ggctgatgat cataaccctg cgttttgcac cagtacgttt tccgcagctg | 180 |
| tgggtcaaag acgctcaagt tagtataaaa aagctgaacg agaaacgtaa aatgatataa | 240 |
| atatcaatat attaaattag attttgcata aaaaacagac tacataatac tgtaaaacac | 300 |
| aacatatgca gtcactatga atcaactact tagatggtat tagtgacctg taacagactg | 360 |
| cagtggtcga aaaaaaagc ccgcactgtc aggtgcgggc ttttttctgt gttaagcttc | 420 |
| gacgaatttc tgccattcat ccgcttatta tcacttattc aggcgtagca ccaggcgttt | 480 |
| aagggcacca ataactgcct taaaaaaatt acgccccgcc ctgccactca tcgcagtact | 540 |
| gttgtaattc attaagcatt ctgccgacat ggaagccatc acagacggca tgatgaacct | 600 |
| gaatcgccag cggcatcagc accttgtcgc cttgcgtata atatttgccc atggtgaaaa | 660 |
| cgggggcgaa gaagttgtcc atattggcca cgtttaaatc aaaactggtg aaactcaccc | 720 |

```
agggattggc tgagacgaaa aacatattct caataaaccc tttagggaaa taggccaggt    780
tttcaccgta acacgccaca tcttgcgaat atatgtgtag aaactgccgg aaatcgtcgt    840
ggtattcact ccagagcgat gaaaacgttt cagtttgctc atggaaaacg gtgtaacaag    900
ggtgaacact atcccatatc accagctcac cgtctttcat tgccatacgg aattccggat    960
gagcattcat caggcgggca agaatgtgaa taaaggccgg ataaaacttg tgcttatttt   1020
tctttacggt ctttaaaaag gccgtaatat ccagctgaac ggtctggtta taggtacatt   1080
gagcaactga ctgaaatgcc tcaaaatgtt ctttacgatg ccattgggat atatcaacgg   1140
tggtatatcc agtgattttt ttctccattt tagcttcctt agctcctgaa aatctcggat   1200
ccgatatcta gctagagcgc ccggttgacg ctgctagtgt tacctagcga tttgtatctt   1260
actgcatgtt acttcatgtt gtcaatacct gtttttcgtg cgacttatca ggctgtctac   1320
ttatccggag atccacagga cgggtgtggt cgccatgatc gcgtagtcga tagtggctcc   1380
aagtagcgaa gcgagcagga ctgggcggcg gccaaagcgg tcggacagtg ctccgagaac   1440
gggtgcgcat agaaattgca tcaacgcata tagcgctagc agcacgccat agtgactggc   1500
gatgctgtcg gaatggacga tatcccgcaa gaggcccggc agtaccggca taaccaagcc   1560
tatgcctaca gcatccaggg tgacggtgcc gaggatgacg atgagcgcat tgttagattt   1620
catacacggt gcctgactgc gttagcaatt taactgtgat aaactaccgc attaaagctt   1680
atcgatgata agctgtcaaa catgagaatt cgaaatcaaa taatgatttt attttgactg   1740
atagtgacct gttcgttgca acaaattgat aagcaatgct ttttttataat gccaacttag   1800
tataaaaaag caggcttcaa gatcttcacc taccaaacaa tgccccctg caaaaaataa    1860
attcatataa aaacataca gataaccatc tgcggtgata aattatctct ggcggtgttg   1920
acataaatac cactggcggt gatactgagc acatcagcag gacgcactga ccaccatgaa   1980
ggtgacgctc ttaaaaatta gccctgaag aagggcagca ttcaaagcag aaggctttgg    2040
ggtgtgtgat acgaaacgaa gcattggccg gaaggagaac taactatggc tgactcgcaa   2100
cccctgtccg gtgctccgga aggtgccgaa t                                  2131
```

<210> SEQ ID NO 24
<211> LENGTH: 534
<212> TYPE: DNA
<213> ORGANISM: Artificial Sequence
<220> FEATURE:
<223> OTHER INFORMATION: DNA fragment 5

<400> SEQUENCE: 24

```
aagctggtgg cgtttatgca gggaatcggt tttatcatcg ccgggcttgc cccgtggttt     60
tctggcgtgc tgcgtagtat cagcggcaat tacctgatgg actgggcatt tcatgcgctg    120
tgcgtcgttg ggctgatgat cataaccctg cgttttgcac cagtacgttt tccgcagctg    180
tgggtcaaag acgctcaagt tagtataaaa aagcaggctt caagatcttc acctaccaaa    240
caatgccccc ctgcaaaaaa taaattcata taaaaaacat acagataacc atctgcggtg    300
ataaattatc tctggcggtg ttgacataaa taccactggc ggtgatactg agcacatcag    360
caggacgcac tgaccaccat gaaggtgacg ctcttaaaaa ttaagccctg aagaagggca    420
gcattcaaag cagaaggctt tggggtgtgt gatacgaaac gaagcattgg ccggaaggag    480
aactaactat ggctgactcg caaccccctgt ccggtgctcc ggaaggtgcc gaat          534
```

<210> SEQ ID NO 25

<211> LENGTH: 3195
<212> TYPE: DNA
<213> ORGANISM: Artificial Sequence
<220> FEATURE:
<223> OTHER INFORMATION: kdcA-aldH

<400> SEQUENCE: 25

| | | | | | |
|---|---|---|---|---|---|
| ctcggtaccg | aaggagggaa | tgtgatgtat | acggtaggag | attacctgtt | agaccgctta | 60 |
| cacgagttgg | gaattgaaga | aattttttgga | gttccgggtg | actataactt | acaattttta | 120 |
| gatcaaatta | tttcacgcga | agatatgaaa | tggattggaa | atgctaatga | attaaatgct | 180 |
| tcttatatgg | ctgatggtta | tgctcgtact | aaaaaagctg | ccgcatttct | caccacgttt | 240 |
| ggagtcggcg | aattgagtgc | gatcaatgga | ctggcaggaa | gttatgccga | aaatttaccg | 300 |
| gtagtagaaa | ttgttggttc | accgacttca | aaagtacaaa | atgacggaaa | atttgtccat | 360 |
| catacgctgg | cagatggtga | ttttaaacac | tttatgaaga | tgcatgaacc | ggttacggca | 420 |
| gcgcgcactt | tactgacggc | agaaaatgcc | acgtatgaaa | ttgaccgcgt | actttctcaa | 480 |
| ttactgaaag | aacgcaaacc | ggtctatatt | aacttaccgg | tcgatgttgc | tgcagcaaaa | 540 |
| gcagagaagc | cggcattatc | tttagaaaaa | gaaagctcta | cgacgaatac | gactgaacaa | 600 |
| gtgattttga | gtaagattga | agaaagtttg | aaaaatgccc | aaaaaccggt | agtgattgca | 660 |
| ggacacgaag | taattagttt | tggtttagaa | aaaacggtaa | ctcagtttgt | ttcagaaacg | 720 |
| aaactgccga | ttacgacgct | gaattttggt | aaagtgctg | ttgatgaatc | tttgccgtca | 780 |
| tttttaggaa | tttataacgg | gaaactttca | gaaatcagtc | ttaaaaattt | tgtggagtcc | 840 |
| gcagactta | tcctgatgct | tggagtgaag | cttacggact | cctcaacggg | tgcattcacg | 900 |
| catcatttag | atgaaaataa | aatgatttca | ctgaacattg | atgaaggaat | tattttcaat | 960 |
| aaagtggtag | aagattttga | ttttcgcgca | gtggtttctt | ctttatcaga | attaaaagga | 1020 |
| attgaatatg | aaggacaata | tattgataag | caatatgaag | aatttattcc | gtcaagtgct | 1080 |
| ccgttatcac | aagaccgtct | gtggcaggca | gttgaaagtt | tgactcaaag | caatgaaacg | 1140 |
| atcgttgctg | aacaaggaac | ctcattttt | ggagcttcaa | cgattttctt | aaaatcaaat | 1200 |
| agtcgtttta | ttggacaacc | gttatggggt | tctattggat | atacttttcc | ggcggcttta | 1260 |
| ggaagccaaa | ttgcggataa | agagagccgc | cacctttat | ttattggtga | tggttcactt | 1320 |
| caacttaccg | tacaagaatt | aggactgtca | atccgcgaaa | aactcaatcc | gatttgtttt | 1380 |
| atcattaata | atgatggtta | tacggttgaa | cgcgaaatcc | acggaccgac | tcaaagttat | 1440 |
| aacgacattc | cgatgtggaa | ttactcgaaa | ttaccggaaa | cgtttggagc | aacgaagat | 1500 |
| cgtgtagtat | caaaaattgt | tcgcacggag | aatgaatttg | tgtctgtcat | gaagaagcc | 1560 |
| caagcagatg | tcaatcgcat | gtattggatt | gaactggttt | tggaaaaaga | agatgcgccg | 1620 |
| aaattactga | aaaaaatggg | taaattattt | gctgagcaaa | ataaataagg | atcctttaag | 1680 |
| aaggagatat | acatatgaat | ttcatcatc | tggcttactg | gcaggataaa | gcgttaagtc | 1740 |
| tcgccattga | aaaccgctta | tttattaacg | gtgaatatac | tgctgcggcg | aaaatgaaa | 1800 |
| cctttgaaac | cgttgatccg | gtcacccagg | caccgctggc | gaaaattgcc | cgcggcaaga | 1860 |
| gcgtcgatat | cgaccgtgcg | atgagcgcag | cacgcggcgt | atttgaacgc | ggcgactggt | 1920 |
| cactctcttc | tccggctaaa | cgtaaagcgg | tactgaataa | actcgccgat | ttaatggaag | 1980 |
| cccacgccga | agagctggca | ctgctggaaa | ctctcgacac | cggcaaaccg | attcgtcaca | 2040 |
| gtctgcgtga | tgatattccc | ggcgcggcgc | gcgccattcg | ctggtacgcc | gaagcgatcg | 2100 |
| acaaagtgta | tggcgaagtg | gcgaccacca | gtagccatga | gctggcgatg | atcgtgcgtg | 2160 |

```
aaccggtcgg cgtgattgcc gccatcgtgc cgtggaactt cccgctgttg ctgacttgct    2220
ggaaactcgg cccggcgctg gcggcgggaa acagcgtgat tctaaaaccg tctgaaaaat    2280
caccgctcag tgcgattcgt ctcgcggggc tggcgaaaga agcaggcttg ccggatggtg    2340
tgttgaacgt ggtgacgggt tttggtcatg aagcccgggca ggcgctgtcg cgtcataacg    2400
atatcgacgc cattgccttt accggttcaa cccgtaccgg aaacagctg ctgaaagatg    2460 cgggcgacag caacatgaaa cgcgtctggc tggaagcggg cggcaaaagc gccaacatcg    2520
ttttcgctga ctgcccggat ttgcaacagg cggcaagcgc caccgcagca ggcattttct    2580
acaaccaggg acaggtgtgc atcgccggaa cgcgcctgtt gctggaagag agcatcgccg    2640
atgaattctt agccctgtta aaacagcagg cgcaaaactg gcagccgggc catccacttg    2700
atcccgcaac caccatgggc accttaatcg actgcgccca cgccgactcg gtccatagct    2760
ttattcggga aggcgaaagc aaagggcaac tgttgttgga tggccgtaac gccgggctgg    2820
ctgccgccat cggcccgacc atctttgtgg atgtggaccc gaatgcgtcc ttaagtcgcg    2880
aagagatttt cggtccggtg ctggtggtca cgcgtttcac atcagaagaa caggcgctac    2940
agcttgccaa cgacagccag tacgcccttg gcgcggcggt atggacgcgc gacctctccc    3000
gcgcgcaccg catgagccga cgcctgaaag ccggttccgt cttcgtcaat aactacaacg    3060
acggcgatat gaccgtgccg tttggcggct ataagcagag cggcaacggt cgcgacaaat    3120
ccctgcatgc ccttgaaaaa ttcactgaac tgaaaaccat ctggataagc ctggaggcct    3180
gagatcctct agagg                                                    3195

<210> SEQ ID NO 26
<211> LENGTH: 20
<212> TYPE: DNA
<213> ORGANISM: Artificial Sequence
<220> FEATURE:
<223> OTHER INFORMATION: Primer P5

<400> SEQUENCE: 26
ctgagtagga caaatccgcc                                                 20

<210> SEQ ID NO 27
<211> LENGTH: 20
<212> TYPE: DNA
<213> ORGANISM: Artificial Sequence
<220> FEATURE:
<223> OTHER INFORMATION: Primer P6

<400> SEQUENCE: 27
gttatagtca cccggaactc                                                 20

<210> SEQ ID NO 28
<211> LENGTH: 22
<212> TYPE: DNA
<213> ORGANISM: Artificial Sequence
<220> FEATURE:
<223> OTHER INFORMATION: Primer P7

<400> SEQUENCE: 28
agtagagacg aaagtgattg cg                                              22

<210> SEQ ID NO 29
<211> LENGTH: 20
<212> TYPE: DNA
<213> ORGANISM: Artificial Sequence
<220> FEATURE:
```

<223> OTHER INFORMATION: Primer P8

<400> SEQUENCE: 29
gcgacagcaa catgaaacgc                                                      20

<210> SEQ ID NO 30
<211> LENGTH: 1045
<212> TYPE: DNA
<213> ORGANISM: Artificial Sequence
<220> FEATURE:
<223> OTHER INFORMATION: DNA fragment 6

<400> SEQUENCE: 30
ctgagtagga caaatccgcc gggagcggat ttgaacgttg cgaagcaacg gcccggaggg          60
tggcgggcag gacgcccgcc ataaactgcc aggcatcaaa ttaagcagaa ggccatcctg         120
acggatggcc ttttttgcgtg gctcggtacc gaaggaggga atgtgatgta tacggtagga        180
gattacctgt tagaccgctt acacgagttg ggaattgaag aaattttttgg agttccgggt       240 gactataact tacaatttttt agatcaaatt atttcacgcg aagatatgaa atggattgga       300
aatgctaatg aattaaatgc ttcttatatg gctgatggtt atgctcgtac taaaaaagct       360
gccgcatttc tcaccacgtt tggagtcggc gaattgagtg cgatcaatgg actggcagga       420
agttatgccg aaaatttacc ggtagtagaa attgttggtt caccgacttc aaaagtacaa       480
aatgacggaa aatttgtcca tcatacgctg gcagatggta ttttaaaca ctttatgaag         540 atgcatgaac cggttacggc agcgcgcact ttactgacgg cagaaaatgc cacgtatgaa       600
attgaccgcg tactttctca attactgaaa gaacgcaaac cggtctatat taacttaccg       660
gtcgatgttg ctgcagcaaa agcagagaag ccggcattat ctttagaaaa agaaagctct       720
acgacgaata cgactgaaca agtgattttg agtaagattg aagaaagttt gaaaaatgcc       780
caaaaaccgg tagtgattgc aggacacgaa gtaattagtt ttggtttaga aaaaacggta       840
actcagtttg tttcagaaac gaaactgccg attacgacgc tgaattttgg taaaagtgct       900
gttgatgaat ctttgccgtc attttttagga atttataacg ggaaactttc agaaatcagt      960
cttaaaaatt ttgtggagtc cgcagacttt atcctgatgc ttggagtgaa gcttacggac       1020
tcctcaacgg gtgcattcac gcatc                                             1045

<210> SEQ ID NO 31
<211> LENGTH: 865
<212> TYPE: DNA
<213> ORGANISM: Artificial Sequence
<220> FEATURE:
<223> OTHER INFORMATION: DNA fragment 7

<400> SEQUENCE: 31
gcgacagcaa catgaaacgc gtctggctgg aagcgggcgg caaaagcgcc aacatcgttt         60
tcgctgactg cccggatttg caacaggcgg caagcgccac cgcagcaggc attttctaca       120
accagggaca ggtgtgcatc gccggaacgc gcctgttgct ggaagagagc atcgccgatg       180
aattcttagc cctgttaaaa cagcaggcgc aaaactggca gccgggccat ccacttgatc       240
ccgcaaccac catgggcacc ttaatcgact gcgcccacgc cgactcggtc catagcttta       300
ttcgggaagg cgaaagcaaa gggcaactgt tgttggatgg ccgtaacgcc gggctggctg       360
ccgccatcgg cccgaccatc tttgtggatg tggacccgaa tgcgtcctta agtcgcgaag       420
agattttcgg tccggtgctg gtggtcacgc gtttcacatc agaagaacag gcgctacagc       480
ttgccaacga cagccagtac ggccttggcg cggcggtatg gacgcgcgac ctctcccgcg       540

```
cgcaccgcat gagccgacgc ctgaaagccg gttccgtctt cgtcaataac tacaacgacg    600
gcgatatgac cgtgccgttt ggcggctata agcagagcgg caacggtcgc gacaaatccc    660
tgcatgccct tgaaaaattc actgaactga aaaccatctg gataagcctg gaggcctgag    720
atcctctaga ggtcgactct agaggatccc cgggtaccga gctcgaattc tcatgtttga    780
cagcttatca ctgatcagtg aattaatggc gatgacgcat cctcacgata atatccgggt    840
aggcgcaatc actttcgtct ctact                                          865

<210> SEQ ID NO 32
<211> LENGTH: 27
<212> TYPE: DNA
<213> ORGANISM: Artificial Sequence
<220> FEATURE:
<223> OTHER INFORMATION: Primer P9

<400> SEQUENCE: 32
gccatggcag aatctgctcc atgcggg                                         27

<210> SEQ ID NO 33
<211> LENGTH: 20
<212> TYPE: DNA
<213> ORGANISM: Artificial Sequence
<220> FEATURE:
<223> OTHER INFORMATION: Primer P10

<400> SEQUENCE: 33
gttatagtca cccggaactc                                                 20

<210> SEQ ID NO 34
<211> LENGTH: 1629
<212> TYPE: DNA
<213> ORGANISM: Artificial Sequence
<220> FEATURE:
<223> OTHER INFORMATION: DNA fragment 8

<400> SEQUENCE: 34
gccatggcag aatctgctcc atgcgggaca agaaaatctc ttttctggtc tgacggcgct     60
tactgctgaa ttcactgtcg gcgaaggtaa gttgatgact catgatgaac cctgttctat    120
ggctccagat gacaaacatg atctcatatc agggacttgt tcgcaccttc cttagtactt    180
cccccaataa ttggctggtg tttatgcaaa atggtcaaga agtggtaatt gatagcggta    240
aaagcgttag cctcacactg acaatggctc cagcttttaa ggatgaaggg gaactaaccg    300
acatgacaga tattacaggc aatctgacgg tcctggtgga ggcaaaatga caatgtaaa    360 attactgatt gccggaagtg cctttttttgc catgtcagcg caagccgctg atagagtatc    420
aattgacgtt aaggtgactc tggaagctgc agaaaggtca ttttttcctga atatgctcac    480 atcatataaa gaaatacaga taaagttatt atctgcttgt ggtggtgaat gcactgaccg    540
gctataagga aaggccaaac aagacacggt tgcaaaaacc gtgcccttaa atattgaatc    600
tctattcaga acactttctt aaattgtcat ttggcatatt acgaacaatt ccgcgtaaaa    660
acgttctgtt acgctaaacc cttatccagc aggctttcaa ggatgtaaac cataacactc    720
tgcgaactag tgttacattg cgtgtagctt tgagtgggca actttgtgta cacttttgtg    780
tacccaaaaa caaaaatgtg tacccattca atgatcaccg acacaaagct caggaaggcg    840
ctcggcaaga aaagagatga tatcgagatt atttctgatt cgcacgagct ttctagacgc    900
tcaagttagt ataaaaaagc tgaacgagaa acgtaaaatg atataaatat caatatatta    960
```

```
aattagattt tgcataaaaa acagactaca taatactgta aaacacaaca tatgcagtca    1020
ctatgaatca actacttaga tggtattagt gacctgtaac agactgcggg cccaggttat    1080
gctgctttta agacccactt tcacatttaa gttgttttc taatccgcat atgatcaatt    1140
caaggccgaa taagaaggct ggctctgcac cttggtgatc aaataattcg atagcttgtc    1200
gtaataatgg cggcatacta tcagtagtag gtgtttccct ttcttcttta gcgacttgat    1260
gctcttgatc ttccaatacg caacctaaag taaaatgccc cacagcgctg agtgcatata    1320
atgcattctc tagtgaaaaa ccttgttggc ataaaaggc taattgattt tcgagagttt    1380
catactgttt ttctgtaggc cgtgtaccta aatgtacttt tgctccatcg cgatgactta    1440
gtaaagcaca tctaaaactt ttagcgttat tacgtaaaaa atcttgccag ctttcccctt    1500
ctaaagggca aaagtgagta tggtgcctat ctaacatctc aatggctaag gcgtcgagca    1560
aagcccgctt attttttaca tgccaataca atgtaggctg ctctacacct agcttctggg    1620
cgagtttac                                                           1629

<210> SEQ ID NO 35
<211> LENGTH: 22
<212> TYPE: DNA
<213> ORGANISM: Artificial Sequence
<220> FEATURE:
<223> OTHER INFORMATION: Primer P11

<400> SEQUENCE: 35
gtaaactcgc ccagaagcta gg                                              22

<210> SEQ ID NO 36
<211> LENGTH: 4603
<212> TYPE: DNA
<213> ORGANISM: Artificial Sequence
<220> FEATURE:
<223> OTHER INFORMATION: DNA fragment 9

<400> SEQUENCE: 36
gccatggcag aatctgctcc atgcgggaca agaaaatctc ttttctggtc tgacggcgct     60
tactgctgaa ttcactgtcg gcgaaggtaa gttgatgact catgatgaac cctgttctat    120
ggctccagat gacaaacatg atctcatatc agggacttgt tcgcaccttc cttagtactt    180
cccccaataa ttggctggtg tttatgcaaa atggtcaaga agtggtaatt gatagcggta    240
aaagcgttag cctcacactg acaatggctc cagcttttaa ggatgaaggg gaactaaccg    300
acatgacaga tattacaggc aatctgacgg tcctggtgga ggcaaaatga acaatgtaaa    360
attactgatt gccggaagtg cctttttgc catgtcagcg caagccgctg atagagtatc    420
aattgacgtt aaggtgactc tggaagctgc agaaaggtca tttttcctga atatgctcac    480
atcatataaa gaaatacaga taaagttatt atctgcttgt ggtggtgaat gcactgaccg    540
gctataagga aaggccaaac aagacacggt tgcaaaaacc gtgcccttaa atattgaatc    600
tctattcaga acactttctt aaattgtcat ttggcatatt acgaacaatt ccgcgtaaaa    660
acgttctgtt acgctaaacc cttatccagc aggctttcaa ggatgtaaac cataacactc    720
tgcgaactag tgttacattg cgtgtagctt tgagtgggca actttgtgta cacttttgtg    780
tacccaaaaa caaaaatgtg tacccattca atgatcaccg acacaaagct caggaaggcg    840
ctcggcaaga aaagagatga tatcgagatt atttctgatt cgcacgagct ttctagacgc    900
tcaagttagt ataaaaagc tgaacgagaa acgtaaaatg atataaatat caatatatta    960
aattagattt tgcataaaaa acagactaca taatactgta aaacacaaca tatgcagtca   1020
```

```
ctatgaatca actacttaga tggtattagt gacctgtaac agactgcggg cccaggttat    1080
gctgctttta agacccactt tcacatttaa gttgtttttc taatccgcat atgatcaatt    1140
caaggccgaa taagaaggct ggctctgcac cttggtgatc aaataattcg atagcttgtc    1200
gtaataatgg cggcatacta tcagtagtag gtgtttccct ttcttcttta gcgacttgat    1260
gctcttgatc ttccaatacg caacctaaag taaaatgccc cacagcgctg agtgcatata    1320
atgcattctc tagtgaaaaa ccttgttggc ataaaaaggc taattgattt tcgagagttt    1380
catactgttt ttctgtaggc cgtgtaccta aatgtacttt tgctccatcg cgatgactta    1440
gtaaagcaca tctaaaactt ttagcgttat tacgtaaaaa atcttgccag ctttcccctt    1500
ctaaagggca aaagtgagta tggtgcctat ctaacatctc aatggctaag gcgtcgagca    1560
aagcccgctt attttttaca tgccaataca atgtaggctg ctctacacct agcttctggg    1620
cgagtttacg ggttgttaaa ccttcgattc cgacctcatt aagcagctct aatgcgctgt    1680
taatcacttt acttttatct aatctagaca tcattaattc ctaattttg ttgacactct    1740 atcattgata gagttatttt accactccct atcagtgata gagaaaagtg aaatgaatag    1800
ttcgacaaag atcgcattgg taattacgtt actcgatgcc atggggattg gccttatcat    1860
gccagtcttg ccaacgttat tacgtgaatt tattgcttcg gaagatatcg ctaaccactt    1920
tggcgtattg cttgcacttt atgcgttaat gcaggttatc tttgctcctt ggcttggaaa    1980
aatgtctgac cgatttggtc ggcgcccagt gctgttgttg tcattaatag gcgcatcgct    2040
ggattactta ttgctggctt tttcaagtgc gctttggatg ctgtatttag gccgtttgct    2100
ttcagggatc acaggagcta ctggggctgt cgcggcatcg gtcattgccg ataccacctc    2160
agcttctcaa cgcgtgaagt ggttcggttg gttaggggca agttttgggc ttggtttaat    2220
agcggggcct attattggtg gttttgcagg agagatttca ccgcatagtc ccttttttat    2280
cgctgcgttg ctaaatattg tcactttcct tgtggttatg ttttggttcc gtgaaaccaa    2340
aaatacacgt gataatacag ataccgaagt agggggttgag acgcaatcga attcggtata    2400 catcactta tttaaaacga tgcccatttt gttgattatt tattttcag cgcaattgat    2460 aggccaaatt cccgcaacgg tgtgggtgct atttaccgaa aatcgttttg gatggaatag    2520
catgatggtt ggcttttcat tagcgggtct tggtcttta cactcagtat tccaagcctt    2580
tgtggcagga agaatagcca ctaaatgggg cgaaaaaacg gcagtactgc tcgaatttat    2640
tgcagatagt agtgcatttg ccttttttagc gtttatatct gaaggttggt tagattccc    2700 tgttttaatt ttattggctg gtggtgggat cgctttacct gcattacagg gagtgatgtc    2760
tatccaaaca aagagtcatg agcaaggtgc tttcaggga ttattggtga gccttaccaa    2820
tgcaaccggt gttattggcc cattactgtt tactgttatt tataatcatt cactaccaat    2880
ttgggatggc tggatttgga ttattggttt agcgttttac tgtattatta tcctgctatc    2940
gatgaccttc atgttaaccc ctcaagctca ggggagtaaa caggagacaa gtgcttagtt    3000
atttcgtcac caaatgatgt tattccgcga aatataatga ccctcttgat aacccaagag    3060
ggcatttttt acgagacgtc ctaattccca tgtcagccgt taagtgttcc tgtgtcactg    3120
aaaattgctt tgagaggctc taagggcttc tcagtgcgtt acatccctgg cttgttgtcc    3180
acaaccgtta aaccttaaaa gctttaaaag ccttatatat tctttttttt cttataaaac    3240
ttaaaacctt agaggctatt taagttgctg atttatatta attttattgt tcaaacatga    3300
gagcttagta cgtgaaacat gagagcttag tacgttagcc atgagagctt agtacgttag    3360
```

```
ccatgagggt ttagttcgtt aaacatgaga gcttagtacg ttaaacatga gagcttagta    3420
cgtgaaacat gagagcttag tacgtactat caacaggttg aactgctgat cttcagatcc    3480
tctacgccgg acgcatcgtg gccggatctt gcggccgcaa aaattaaaaa tgaagttttg    3540
gaggcctcat ttggtgacga aataactaag cacttgtctc ctgtttactc ccctgagctt    3600 gagggtcaa catgaaggtc attgatagca ggataataat acagtaaaac gctaaaccaa     3660
taatccaaat ccagccatcc caaattggta gtgaatgatt ataaataaca gtaaacagta    3720
atgggccaat aacaccggtt gcattggtaa ggctcaccaa taatccctgt aaagcacctt    3780
gctcatgact ctttgtttgg atagacatca ctccctgtaa tgcaggtaaa gcgatcccac    3840
caccagccaa taaaattaaa acagggaaat ctaaccaacc ttcagatata aacgctaaaa    3900
aggcaaatgc actactatct gcaataaatt cgagcagtac tgccgttttt tcgccccatt    3960
tagtggctat tcttcctgcc acaaaggctt ggaatactga gtgtaaaaga ccaagacccg    4020
ctaatgaaaa gccaaccatc atgctattcc atccaaaacg attttcggta aatagcaccc    4080
acaccgttgc gggaatttgg cctatcaatt cgaaatcaaa taatgatttt attttgactg    4140
atagtgacct gttcgttgca acaaattgat aagcaatgct ttttataat gccaacttag      4200 tataaaaaag caggcttcag agcgatggcc cccgatggta gtgtggggtc tccccatgcg    4260
agagtaggga actgccaggc atcaaataaa acgaaaggct cagtcgaaag actgggcctt    4320 tcgtttatc tgttgtttgt cggtgaacgc tctcctgagt aggacaaatc cgccgggagc      4380
ggatttgaac gttgcgaagc aacggcccgg agggtggcgg gcaggacgcc cgccataaac    4440
tgccaggcat caaattaagc agaaggccat cctgacggat ggccttttg cgtggctcgg      4500 taccgaagga gggaatgtga tgtatacggt aggagattac ctgttagacc gcttacacga    4560
gttgggaatt gaagaaattt ttggagttcc gggtgactat aac                      4603

<210> SEQ ID NO 37
<211> LENGTH: 1312
<212> TYPE: DNA
<213> ORGANISM: Artificial Sequence
<220> FEATURE:
<223> OTHER INFORMATION: DNA fragment 10

<400> SEQUENCE: 37
gccatggcag aatctgctcc atgcgggaca agaaaatctc ttttctggtc tgacggcgct      60
tactgctgaa ttcactgtcg gcgaaggtaa gttgatgact catgatgaac cctgttctat     120
ggctccagat gacaaacatg atctcatatc agggacttgt tcgcaccttc cttagtactt     180 ccccaataa ttggctggtg tttatgcaaa atggtcaaga agtggtaatt gatagcggta     240
aaagcgttag cctcacactg acaatggctc cagcttttaa ggatgaaggg gaactaaccg      300
acatgacaga tattacaggc aatctgacgg tcctggtgga ggcaaaatga acaatgtaaa     360
attactgatt gccggaagtg ccttttttgc catgtcagcg caagccgctg atagagtatc     420
aattgacgtt aaggtgactc tggaagctgc agaaaggtca ttttttcctga atatgctcac    480 atcatataaa gaaatacaga taaagttatt atctgcttgt ggtggtgaat gcactgaccg    540
gctataagga aaggccaaac aagacacggt tgcaaaaacc gtgcccttaa atattgaatc    600
tctattcaga acactttctt aaattgtcat ttggcatatt acgaacaatt ccgcgtaaaa    660
acgttctgtt acgctaaacc cttatccagc aggcttcaa ggatgtaaac cataacactc      720
tgcgaactag tgttacattg cgtgtagctt tgagtgggca actttgtgta cacttttgtg    780
tacccaaaaa caaaaatgtg tacccattca atgatcaccg acacaaagct caggaaggcg    840
```

```
ctcggcaaga aaagagatga tatcgagatt atttctgatt cgcacgagct ttctagacgc    900
tcaagttagt ataaaaaagc aggcttcaga gcgatggccc ccgatggtag tgtggggtct    960
ccccatgcga gagtagggaa ctgccaggca tcaaataaaa cgaaaggctc agtcgaaaga    1020
ctgggccttt cgttttatct gttgtttgtc ggtgaacgct ctcctgagta ggacaaatcc    1080
gccgggagcg gatttgaacg ttgcgaagca acggcccgga gggtggcggg caggacgccc    1140
gccataaact gccaggcatc aaattaagca gaaggccatc ctgacggatg ccttttttgc    1200
gtggctcggt accgaaggag ggaatgtgat gtatacggta ggagattacc tgttagaccg    1260
cttacacgag ttgggaattg aagaaatttt tggagttccg ggtgactata ac            1312
```

<210> SEQ ID NO 38
<211> LENGTH: 64
<212> TYPE: DNA
<213> ORGANISM: Artificial Sequence
<220> FEATURE:
<223> OTHER INFORMATION: Primer P12

<400> SEQUENCE: 38

```
gtagtgtggg gtctccccat gcgagagtag ggaactcgct caagttagta taaaaaagct    60
gaac                                                                  64
```

<210> SEQ ID NO 39
<211> LENGTH: 64
<212> TYPE: DNA
<213> ORGANISM: Artificial Sequence
<220> FEATURE:
<223> OTHER INFORMATION: Primer P13

<400> SEQUENCE: 39

```
gtaatctcct accgtataca tcacattccc tccttcgctc acaattccac acattatacg    60
agcc                                                                  64
```

<210> SEQ ID NO 40
<211> LENGTH: 1768
<212> TYPE: DNA
<213> ORGANISM: Artificial Sequence
<220> FEATURE:
<223> OTHER INFORMATION: DNA fragment 11

<400> SEQUENCE: 40

```
gtagtgtggg gtctccccat gcgagagtag ggaactcgct caagttagta taaaaaagct    60
gaacgagaaa cgtaaaatga tataaatatc aatatattaa attagatttt gcataaaaaa    120
cagactacat aatactgtaa aacacaacat atgcagtcac tatgaatcaa ctacttagat    180
ggtattagtg acctgtaaca gactgcagtg gtcgaaaaaa aaagcccgca ctgtcaggtg    240
cgggcttttt tctgtgttaa gcttcgacga atttctgcca ttcatccgct tattatcact    300
tattcaggcg tagcaccagg cgtttaaggg caccaataac tgccttaaaa aaattacgcc    360
ccgccctgcc actcatcgca gtactgttgt aattcattaa gcattctgcc gacatggaag    420
ccatcacaga cggcatgatg aacctgaatc gccagcggca tcagcacctt gtcgccttgc    480
gtataatatt tgcccatggt gaaacggggg cgaagaagt tgtccatatt ggccacgttt     540
aaatcaaaac tggtgaaact cacccaggga ttggctgaga cgaaaaacat attctcaata    600
aaccctttag ggaaataggc caggttttca ccgtaacacg ccacatcttg cgaatatatg    660
tgtagaaact gccggaaatc gtcgtggtat tcactccaga gcgatgaaaa cgtttcagtt    720
```

```
tgctcatgga aaacggtgta acaagggtga acactatccc atatcaccag ctcaccgtct    780
ttcattgcca tacggaattc cggatgagca ttcatcaggc gggcaagaat gtgaataaag    840
gccggataaa acttgtgctt attttctt acggtcttta aaaaggccgt aatatccagc    900
tgaacggtct ggttataggt acattgagca actgactgaa atgcctcaaa atgttcttta    960
cgatgccatt gggatatatc aacggtggta tatccagtga ttttttctc catttagct    1020 tccttagctc ctgaaaatct cggatccggc caagctagct tggctctagc tagagcgccc    1080
ggttgacgct gctagtgtta cctagcgatt tgtatcttac tgcatgttac ttcatgttgt    1140
caatacctgt ttttcgtgcg acttatcagg ctgtctactt atccggagat ccacaggacg    1200
ggtgtggtcg ccatgatcgc gtagtcgata gtggctccaa gtagcgaagc gagcaggact    1260
gggcggcggc caaagcggtc ggacagtgct ccgagaacgg gtgcgcatag aaattgcatc    1320
aacgcatata gcgctagcag cacgccatag tgactggcga tgctgtcgga atggacgata    1380
tcccgcaaga ggcccggcag taccggcata accaagccta tgcctacagc atccaggtg    1440 acggtgccga ggatgacgat gagcgcattg ttagatttca tacacggtgc ctgactgcgt    1500
tagcaattta actgtgataa actaccgcat taaagcttat cgatgataag ctgtcaaaca    1560
tgagaattcg aaatcaaata atgatttat tttgactgat agtgacctgt tcgttgcaac    1620
aaattgataa gcaatgcttt tttataatgc caacttagta taaaaaagca ggcttcaaga    1680
tctccctgtt gacaattaat catcggctcg tataatgtgt ggaattgtga gcgaaggagg    1740
gaatgtgatg tatacggtag gagattac                                      1768

<210> SEQ ID NO 41
<211> LENGTH: 20
<212> TYPE: DNA
<213> ORGANISM: Artificial Sequence
<220> FEATURE:
<223> OTHER INFORMATION: Primer P14

<400> SEQUENCE: 41
gatagtgacc tgttcgttgc                                                 20

<210> SEQ ID NO 42
<211> LENGTH: 1030
<212> TYPE: DNA
<213> ORGANISM: Artificial Sequence
<220> FEATURE:
<223> OTHER INFORMATION: DNA fragment 12

<400> SEQUENCE: 42
gatagtgacc tgttcgttgc aacaaattga taagcaatgc ttttttataa tgccaactta     60
gtataaaaaa gcaggcttca agatctccct gttgacaatt aatcatcggc tcgtataatg    120
tgtggaattg tgagcgaagg agggaatgtg atgtatacgg taggagatta cctgttagac    180
cgcttacacg agttgggaat tgaagaaatt tttggagttc cgggtgacta aacttacaa     240 tttttagatc aaattatttc acgcgaagat atgaaatgga ttggaaatgc taatgaatta    300
aatgcttctt atatggctga tggttatgct cgtactaaaa aagctgccgc atttctcacc    360
acgtttggag tcggcgaatt gagtgcgatc aatggactgg caggaagtta tgccgaaaat    420
ttaccggtag tagaaattgt tggttcaccg acttcaaaag tacaaaatga cggaaaattt    480
gtccatcata cgctggcaga tggtgatttt aaacacttta tgaagatgca tgaaccggtt    540
acggcagcgc gcactttact gacggcagaa aatgccacgt atgaaattga ccgcgtactt    600
tctcaattac tgaaagaacg caaaccggtc tatattaact taccggtcga tgttgctgca    660
```

```
gcaaaagcag agaagccggc attatcttta gaaaaagaaa gctctacgac gaatacgact    720
gaacaagtga ttttgagtaa gattgaagaa agtttgaaaa atgcccaaaa accggtagtg    780
attgcaggac acgaagtaat tagttttggt ttagaaaaaa cggtaactca gtttgtttca    840
gaaacgaaac tgccgattac gacgctgaat tttggtaaaa gtgctgttga tgaatctttg    900
ccgtcatttt taggaattta aacgggaaac tttcagaaa tcagtcttaa aaattttgtg     960
gagtccgcag actttatcct gatgcttgga gtgaagctta cggactcctc aacgggtgca   1020
ttcacgcatc                                                          1030
```

<210> SEQ ID NO 43
<211> LENGTH: 20
<212> TYPE: DNA
<213> ORGANISM: Artificial Sequence
<220> FEATURE:
<223> OTHER INFORMATION: Primer P15

<400> SEQUENCE: 43

```
gccatggcag aatctgctcc                                                 20
```

<210> SEQ ID NO 44
<211> LENGTH: 2777
<212> TYPE: DNA
<213> ORGANISM: Artificial Sequence
<220> FEATURE:
<223> OTHER INFORMATION: DNA fragment 13

<400> SEQUENCE: 44

```
gccatggcag aatctgctcc atgcgggaca agaaaatctc ttttctggtc tgacggcgct     60
tactgctgaa ttcactgtcg gcgaaggtaa gttgatgact catgatgaac cctgttctat    120
ggctccagat gacaaacatg atctcatatc agggacttgt tcgcaccttc cttagtactt    180
cccccaataa ttggctggtg tttatgcaaa atggtcaaga agtggtaatt gatagcggta    240
aaagcgttag cctcacactg acaatggctc cagcttttaa ggatgaaggg gaactaaccg    300
acatgacaga tattacaggc aatctgacgg tcctggtgga ggcaaaatga acaatgtaaa    360
attactgatt gccggaagtg ccttttttgc catgtcagcg caagccgctg atagagtatc    420
aattgacgtt aaggtgactc tggaagctgc agaaaggtca ttttttcctga atatgctcac    480 atcatataaa gaaatacaga taaagttatt atctgcttgt ggtggtgaat gcactgaccg    540
gctataagga aaggccaaac aagacacggt tgcaaaaacc gtgcccttaa atattgaatc    600
tctattcaga acactttctt aaattgtcat ttggcatatt acgaacaatt ccgcgtaaaa    660
acgttctgtt acgctaaacc cttatccagc aggctttcaa ggatgtaaac cataacactc    720
tgcgaactag tgttacattg cgtgtagctt tgagtgggca actttgtgta cacttttgtg    780
tacccaaaaa caaaaatgtg tacccattca atgatcaccg acacaaagct caggaaggcg    840
ctcggcaaga aaagagatga tatcgagatt atttctgatt cgcacgagct ttctagacgc    900
tcaagttagt ataaaaagc aggcttcaga gcgatggccc ccgatggtag tgtggggtct    960
ccccatgcga gagtagggaa ctcgctcaag ttagtataaa aaagctgaac gagaaacgta   1020
aaatgatata aatatcaata tattaaatta gattttgcat aaaaaacaga ctacataata   1080
ctgtaaaaca caacatatgc agtcactatg aatcaactac ttagatggta ttagtgacct   1140
gtaacagact gcagtggtcg aaaaaaaaag cccgcactgt caggtgcggg ctttttttctg   1200 tgttaagctt cgacgaattt ctgccattca tccgcttatt atcacttatt caggcgtagc   1260
```

-continued

```
accaggcgtt taagggcacc aataactgcc ttaaaaaaat tacgccccgc cctgccactc    1320
atcgcagtac tgttgtaatt cattaagcat tctgccgaca tggaagccat cacagacggc    1380
atgatgaacc tgaatcgcca gcggcatcag caccttgtcg ccttgcgtat aatatttgcc    1440
catggtgaaa acggggcga agaagttgtc catattggcc acgtttaaat caaaactggt      1500
gaaactcacc cagggattgg ctgagacgaa aaacatattc tcaataaacc ctttagggaa    1560
ataggccagg ttttcaccgt aacacgccac atcttgcgaa tatatgtgta gaaactgccg    1620
gaaatcgtcg tggtattcac tccagagcga tgaaaacgtt tcagtttgct catggaaaac    1680
ggtgtaacaa gggtgaacac tatcccatat caccagctca ccgtcttttca ttgccatacg    1740 gaattccgga tgagcattca tcaggcgggc aagaatgtga ataaaggccg gataaaactt    1800
gtgcttattt ttcttttacgg tctttaaaaa ggccgtaata tccagctgaa cggtctggtt    1860
ataggtacat tgagcaactg actgaaatgc ctcaaaatgt tctttacgat gccattggga    1920
tatatcaacg gtggtatatc cagtgatttt tttctccatt ttagcttcct tagctcctga    1980
aaatctcgga tccggccaag ctagcttggc tctagctaga gcgcccggtt gacgctgcta    2040
gtgttaccta gcgatttgta tcttactgca tgttacttca tgttgtcaat acctgttttt    2100
cgtgcgactt atcaggctgt ctacttatcc ggagatccac aggacgggtg tggtcgccat    2160
gatcgcgtag tcgatagtgg ctccaagtag cgaagcgagc aggactgggc ggcggccaaa    2220
gcggtcggac agtgctccga gaacgggtgc gcatagaaat tgcatcaacg catatagcgc    2280
tagcagcacg ccatagtgac tggcgatgct gtcggaatgg acgatatccc gcaagaggcc    2340
cggcagtacc ggcataacca agcctatgcc tacagcatcc agggtgacgg tgccgaggat    2400
gacgatgagc gcattgttag atttcataca cggtgcctga ctgcgttagc aatttaactg    2460
tgataaacta ccgcattaaa gcttatcgat gataagctgt caaacatgag aattcgaaat    2520
caaataatga ttttattttg actgatagtg accgttcgt tgcaacaaat tgataagcaa    2580
tgctttttta taatgccaac ttagtataaa aaagcaggct tcaagatctc cctgttgaca    2640
attaatcatc ggctcgtata atgtgtggaa ttgtgagcga aggagggaat gtgatgtata    2700
cggtaggaga ttacctgtta gaccgcttac acgagttggg aattgaagaa atttttggag    2760
ttccgggtga ctataac                                                    2777
```

<210> SEQ ID NO 45
<211> LENGTH: 1167
<212> TYPE: DNA
<213> ORGANISM: Artificial Sequence
<220> FEATURE:
<223> OTHER INFORMATION: DNA fragment 14

<400> SEQUENCE: 45

```
gccatggcag aatctgctcc atgcgggaca agaaaatctc ttttctggtc tgacggcgct     60
tactgctgaa ttcactgtcg gcgaaggtaa gttgatgact catgatgaac cctgttctat    120
ggctccagat gacaaacatg atctcatatc agggacttgt tcgcaccttc cttagtactt    180
cccccaataa ttggctggtg tttatgcaaa atggtcaaga agtggtaatt gatagcggta    240
aaagcgttag cctcacactg acaatggctc cagcttttaa ggatgaaggg gaactaaccg    300
acatgacaga tattacaggc aatctgacgg tcctggtgga ggcaaaatga acaatgtaaa    360
attactgatt gccggaagtg cctttttttgc catgtcagcg caagccgctg atagagtatc    420
aattgacgtt aaggtgactc tggaagctgc agaaaggtca ttttttcctga atatgctcac    480 atcatataaa gaaatacaga taaagttatt atctgcttgt ggtggtgaat gcactgaccg    540
```

```
gctataagga aaggccaaac aagacacggt tgcaaaaacc gtgcccttaa atattgaatc    600
tctattcaga acactttctt aaattgtcat ttggcatatt acgaacaatt ccgcgtaaaa    660
acgttctgtt acgctaaacc cttatccagc aggctttcaa ggatgtaaac cataacactc    720
tgcgaactag tgttacattg cgtgtagctt tgagtgggca actttgtgta cacttttgtg    780
tacccaaaaa caaaaatgtg tacccattca atgatcaccg acacaaagct caggaaggcg    840
ctcggcaaga aaagagatga tatcgagatt atttctgatt cgcacgagct ttctagacgc    900
tcaagttagt ataaaaaagc aggcttcaga gcgatggccc ccgatggtag tgtgggtct     960 ccccatgcga gagtagggaa ctcgctcaag ttagtataaa aaagcaggct tcaagatctc    1020
cctgttgaca attaatcatc ggctcgtata atgtgtggaa ttgtgagcga aggagggaat    1080
gtgatgtata cggtaggaga ttacctgtta gaccgcttac acgagttggg aattgaagaa    1140 attttggag ttccgggtga ctataac                                         1167
```

```
<210> SEQ ID NO 46
<211> LENGTH: 64
<212> TYPE: DNA
<213> ORGANISM: Artificial Sequence
<220> FEATURE:
<223> OTHER INFORMATION: Primer P16

<400> SEQUENCE: 46
cagagcacaa ccacatcaca acaaatccgc gcctgatgaa gcctgctttt ttatactaag    60
ttgg                                                                 64

<210> SEQ ID NO 47
<211> LENGTH: 64
<212> TYPE: DNA
<213> ORGANISM: Artificial Sequence
<220> FEATURE:
<223> OTHER INFORMATION: Primer P17

<400> SEQUENCE: 47
catactttat ttactcccag tgtctgtctc gtaaatcgct caagttagta taaaaaagct    60
gaac                                                                 64

<210> SEQ ID NO 48
<211> LENGTH: 1713
<212> TYPE: DNA
<213> ORGANISM: Artificial Sequence
<220> FEATURE:
<223> OTHER INFORMATION: DNA fragment 15

<400> SEQUENCE: 48
cagagcacaa cctcatcaca acaaatccgc gcctgatgaa gcctgctttt ttatactaag    60
ttggcattat aaaaaagcat tgcttatcaa tttgttgcaa cgaacaggtc actatcagtc    120
aaaataaaat cattatttga tttcgaattc tcatgtttga cagcttatca tcgataagct    180
ttaatgcggt agtttatcac agttaaattg ctaacgcagt caggcaccgt gtatgaaatc    240
taacaatgcg ctcatcgtca tcctcggcac cgtcaccctg gatgctgtag cataggctt    300 ggttatgccg gtactgccgg gcctcttgcg ggatatcgtc cattccgaca gcatcgccag    360
tcactatggc gtgctgctag cgctatatgc gttgatgcaa tttctatgcg cacccgttct    420
cggagcactg tccgaccgct ttggccgccg cccagtcctg ctcgcttcgc tacttggagc    480
cactatcgac tacgcgatca tggcgaccac acccgtcctg tggatctccg gataagtaga    540
```

```
cagcctgata agtcgcacga aaaacaggta ttgacaacat gaagtaacat gcagtaagat      600
acaaatcgct aggtaacact agcagcgtca accgggcgct ctagctagag ccaagctagc      660
ttggccggat ccgagatttt caggagctaa ggaagctaaa atggagaaaa aaatcactgg      720
atataccacc gttgatatat cccaatggca tcgtaaagaa catttgagg catttcagtc       780 agttgctcaa tgtacctata accagaccgt tcagctggat attacggcct ttttaaagac      840
cgtaaagaaa ataagcaca gttttatcc ggccttatt cacattcttg cccgcctgat         900
gaatgctcat ccggaattcc gtatggcaat gaaagacggt gagctggtga tatgggatag     960
tgttcaccct tgttcaccg ttttccatga gcaaactgaa acgttttcat cgctctggag      1020
tgaataccac gacgatttcc ggcagtttct acacatatat tcgcaagatg tggcgtgtta    1080
cggtgaaaac ctggcctatt tccctaaagg gtttattgag aatatgtttt tcgtctcagc    1140
caatccctgg gtgagtttca ccagttttga tttaaacgtg gccaatatgg acaacttctt   1200 cgccccgtt ttcaccatgg gcaaatatta tacgcaaggc gacaaggtgc tgatgccgct     1260
ggcgattcag gttcatcatg ccgtctgtga tggcttccat gtcggcagaa tgcttaatga   1320
attacaacag tactgcgatg agtggcaggg cggggcgtaa ttttttttaag gcagttattg  1380 gtgcccttaa acgcctggtg ctacgcctga ataagtgata ataagcggat gaatggcaga   1440
aattcgtcga agcttaacac agaaaaaagc ccgcacctga cagtgcgggc ttttttttc    1500 gaccactgca gtctgttaca ggtcactaat accatctaag tagttgattc atagtgactg   1560
catatgttgt gttttacagt attatgtagt ctgtttttta tgcaaaatct aatttaatat   1620
attgatattt atatcatttt acgtttctcg ttcagctttt ttatactaac ttgagcgatt   1680
tacgagacag acactgggag taaataaagt atg                                 1713

<210> SEQ ID NO 49
<211> LENGTH: 21
<212> TYPE: DNA
<213> ORGANISM: Artificial Sequence
<220> FEATURE:
<223> OTHER INFORMATION: Primer P18

<400> SEQUENCE: 49
ccagtaattc agaaatgttg g                                                21

<210> SEQ ID NO 50
<211> LENGTH: 21
<212> TYPE: DNA
<213> ORGANISM: Artificial Sequence
<220> FEATURE:
<223> OTHER INFORMATION: Primer P19

<400> SEQUENCE: 50
ccatattacg accatgagtg g                                                21

<210> SEQ ID NO 51
<211> LENGTH: 1354
<212> TYPE: DNA
<213> ORGANISM: Artificial Sequence
<220> FEATURE:
<223> OTHER INFORMATION: DNA fragment 16

<400> SEQUENCE: 51
ccagtaattc agaaatgttg gagaaattat catgatgcaa catcaggtca atgtatcggc     60
tcgcttcaat ccgagaaacct tagaacgtgt tttacgcgtg gtgcgtcatc gtggtttcca   120
cgtctgctca atgaatatgg ccgccgccag cgatgcacaa aatataaata tcgaattgac    180
```

```
cgttgccagc ccacggtcgg tcgacttact gtttagtcag ttaaataaac tggtggacgt    240
cgcacacgtt gccatctgcc agagcacaac cacatcacaa caaatccgcg cctgagcgca    300
aaaggaatat aaaaatgacc acgaagaaag ctgattacat ttggttcaat ggggagatgg    360
ttcgctggga agacgcgaag gtgcatgtga tgtcgcacgc gctgcactat ggcacttcgg    420
tttttgaagg catccgttgc tacgactcgc acaaggacc ggttgtattc cgccatcgtg     480
agcatatgca gcgtctgcat gactccgcca aatctatcg cttcccggtt tcgcagagca     540
ttgatgagct gatggaagct tgtcgtgacg tgatccgcaa aaacaatctc accagcgcct    600
atatccgtcc gctgatcttc gtcggtgatg ttggcatggg agtaaacccg ccagcgggat    660
actcaaccga cgtgattatc gctgctttcc cgtggggagc gtatctgggc gcagaagcgc    720
tggagcaggg gatcgatgcg atggtttcct cctggaaccg cgcacgacca acaccatcc     780 cgacggcggc aaaagccggt ggtaactacc tctcttccct gctggtgggt agcgaagcgc    840
gccgccacgt ttatcaggaa ggtatcgcgc tggatgtgaa cggttatatc tctgaaggcg    900
caggcgaaaa cctgtttgaa gtgaaagatg gtgtgctgtt caccccaccg ttcacctcct    960
ccgcgctgcc gggtattacc cgtgatgcca tcatcaaact ggcgaaagag ctgggaattg    1020
aagtacgtga gcaggtgctg tcgcgcgaat ccctgtacct ggcggatgaa gtgtttatgt    1080
ccggtacggc ggcagaaatc acgccagtgc gcagcgtaga cggtattcag gttggcgaag    1140
gccgttgtgg cccggttacc aaacgcattc agcaagcctt cttcggcctc ttcactggcg    1200
aaaccgaaga taatggggc tggttagatc aagttaatca ataaatacaa aaaatgggac    1260
ggcacgcacc gtcccattta cgagacagac actgggagta aataaagtat gcctaagtac    1320
cgttccgcca ccaccactca tggtcgtaat atgg                                1354

<210> SEQ ID NO 52
<211> LENGTH: 2015
<212> TYPE: DNA
<213> ORGANISM: Artificial Sequence
<220> FEATURE:
<223> OTHER INFORMATION: DNA fragment 17

<400> SEQUENCE: 52
ccagtaattc agaaatgttg gagaaattat catgatgcaa catcaggtca atgtatcggc    60
tcgcttcaat ccagaaacct tagaacgtgt tttacgcgtg gtgcgtcatc gtggtttcca    120
cgtctgctca atgaatatgg ccgccgccag cgatgcacaa aatataaata tcgaattgac    180
cgttgccagc ccacggtcgg tcgacttact gtttagtcag ttaaataaac tggtggacgt    240
cgcacacgtt gccatctgcc agagcacaac ctcatcacaa caaatccgcg cctgatgaag    300
cctgcttttt tatactaagt tggcattata aaaagcatt gcttatcaat ttgttgcaac     360
gaacaggtca ctatcagtca aaataaaatc attatttgat ttcgaattct catgtttgac    420
agcttatcat cgataagctt taatgcggta gtttatcaca gttaaattgc taacgcagtc    480
aggcaccgtg tatgaaatct aacaatgcgc tcatcgtcat cctcggcacc gtcaccctgg    540
atgctgtagg cataggcttg gttatgccgg tactgccggg cctcttgcgg gatatcgtcc    600
attccgacag catcgccagt cactatgcg tgctgctagc gctatatgcg ttgatgcaat     660
ttctatgcgc accgttctc ggagcactgt ccgaccgctt tggccgccgc ccagtcctgc     720
tcgcttcgct acttggagcc actatcgact acgcgatcat ggcgaccaca cccgtcctgt    780
ggatctccgg ataagtagac agcctgataa gtcgcacgaa aaacaggtat tgacaacatg    840
```

| | | |
|---|---|---|
| aagtaacatg cagtaagata caaatcgcta ggtaacacta gcagcgtcaa ccgggcgctc | 900 | |
| tagctagagc caagctagct tggccggatc cgagattttc aggagctaag gaagctaaaa | 960 | |
| tggagaaaaa aatcactgga tataccaccg ttgatatatc ccaatggcat cgtaaagaac | 1020 | |
| attttgaggc atttcagtca gttgctcaat gtacctataa ccagaccgtt cagctggata | 1080 | |
| ttacggcctt tttaaagacc gtaaagaaaa ataagcacaa gttttatccg gcctttattc | 1140 | |
| acattcttgc ccgcctgatg aatgctcatc cggaattccg tatggcaatg aaagacggtg | 1200 | |
| agctggtgat atgggatagt gttcaccctt gttacaccgt tttccatgag caaactgaaa | 1260 | |
| cgttttcatc gctctggagt gaataccacg acgatttccg gcagtttcta cacatatatt | 1320 | |
| cgcaagatgt ggcgtgttac ggtgaaaacc tggcctattt ccctaaaggg tttattgaga | 1380 | |
| atatgttttt cgtctcagcc aatccctggg tgagtttcac cagttttgat ttaaacgtgg | 1440 | |
| ccaatatgga caacttcttc gcccccgttt tcaccatggg caaatattat acgcaaggcg | 1500 | |
| acaaggtgct gatgccgctg gcgattcagg ttcatcatgc cgtctgtgat ggcttccatg | 1560 | |
| tcggcagaat gcttaatgaa ttacaacagt actgcgatga gtggcagggc ggggcgtaat | 1620 | |
| ttttttaagg cagttattgg tgcccttaaa cgcctggtgc tacgcctgaa taagtgataa | 1680 | |
| taagcggatg aatggcagaa attcgtcgaa gcttaacaca gaaaaaagcc cgcacctgac | 1740 | |
| agtgcgggct ttttttttcg accactgcag tctgttacag gtcactaata ccatctaagt | 1800 | |
| agttgattca tagtgactgc atatgttgtg ttttacagta ttatgtagtc tgttttttat | 1860 | |
| gcaaaatcta atttaatata ttgatattta tatcatttta cgtttctcgt tcagctttt | 1920 | |
| tatactaact tgagcgattt acgagacaga cactgggagt aaataaagta tgcctaagta | 1980 | |
| ccgttccgcc accaccactc atggtcgtaa tatgg | 2015 | |

<210> SEQ ID NO 53
<211> LENGTH: 405
<212> TYPE: DNA
<213> ORGANISM: Artificial Sequence
<220> FEATURE:
<223> OTHER INFORMATION: DNA fragment 18

<400> SEQUENCE: 53

| | | |
|---|---|---|
| ccagtaattc agaaatgttg gagaaattat catgatgcaa catcaggtca atgtatcggc | 60 | |
| tcgcttcaat ccagaaacct tagaacgtgt tttacgcgtg gtgcgtcatc gtggtttcca | 120 | |
| cgtctgctca atgaatatgg ccgccgccag cgatgcacaa aatataaata tcgaattgac | 180 | |
| cgttgccagc ccacggtcgg tcgacttact gtttagtcag ttaaataaac tggtggacgt | 240 | |
| cgcacacgtt gccatctgcc agagcacaac cacatcacaa caaatccgcg cctgatgaag | 300 | |
| cctgcttttt tatactaact tgagcgattt acgagacaga cactgggagt aaataaagta | 360 | |
| tgcctaagta ccgttccgcc accaccactc atggtcgtaa tatgg | 405 | |

<210> SEQ ID NO 54
<211> LENGTH: 64
<212> TYPE: DNA
<213> ORGANISM: Artificial Sequence
<220> FEATURE:
<223> OTHER INFORMATION: Primer P20

<400> SEQUENCE: 54

| | | |
|---|---|---|
| aaccacctgc ccgtaaacct ggagaaccat cgcgtgtgaa gcctgctttt ttatactaag | 60 | |
| ttgg | 64 | |

```
<210> SEQ ID NO 55
<211> LENGTH: 64
<212> TYPE: DNA
<213> ORGANISM: Artificial Sequence
<220> FEATURE:
<223> OTHER INFORMATION: Primer P21

<400> SEQUENCE: 55
agctccagcc tgctttcctg cattacatca ccgcagcgct caagttagta taaaaaagct    60
gaac                                                                 64

<210> SEQ ID NO 56
<211> LENGTH: 1713
<212> TYPE: DNA
<213> ORGANISM: Artificial Sequence
<220> FEATURE:
<223> OTHER INFORMATION: DNA fragment 19

<400> SEQUENCE: 56
aaccacctgc ccgtaaacct ggagaaccat cgcgtgtgaa gcctgctttt ttatactaag    60
ttggcattat aaaaaagcat tgcttatcaa tttgttgcaa cgaacaggtc actatcagtc   120
aaaataaaat cattatttga tttcgaattc tcatgtttga cagcttatca tcgataagct   180
ttaatgcggt agtttatcac agttaaattg ctaacgcagt caggcaccgt gtatgaaatc   240
taacaatgcg ctcatcgtca tcctcggcac cgtcaccctg gatgctgtag cataggctt    300 ggttatgccg gtactgccgg gcctcttgcg ggatatcgtc cattccgaca gcatcgccag   360
tcactatggc gtgctgctag cgctatatgc gttgatgcaa tttctatgcg cacccgttct   420
cggagcactg tccgaccgct ttggccgccg cccagtcctg ctcgcttcgc tacttggagc   480
cactatcgac tacgcgatca tggcgaccac accgtcctg tggatctccg gataagtaga   540
cagcctgata agtcgcacga aaacaggta ttgacaacat gaagtaacat gcagtaagat   600
acaaatcgct aggtaacact agcagcgtca accgggcgct ctagctagag ccaagctagc   660
ttggccggat ccgagatttt caggagctaa ggaagctaaa atggagaaaa aaatcactgg   720
atataccacc gttgatatat cccaatggca tcgtaaagaa cattttgagg catttcagtc   780
agttgctcaa tgtacctata accagaccgt tcagctggat attacggcct ttttaaagac   840
cgtaaagaaa aataagcaca agttttatcc ggcctttatt cacattcttg cccgcctgat   900
gaatgctcat ccggaattcc gtatggcaat gaaagacggt gagctggtga tatgggatag   960
tgttcaccct tgttacaccg ttttccatga gcaaactgaa acgttttcat cgctctggag  1020
tgaataccac gacgatttcc ggcagtttct acacatatat tcgcaagatg tggcgtgtta  1080
cggtgaaaac ctggcctatt tccctaaagg gtttattgag aatatgtttt tcgtctcagc  1140
caatccctgg gtgagtttca ccagttttga tttaaacgtg gccaatatgg acaacttctt  1200 cgccccgtt ttcaccatgg gcaaatatta tacgcaaggc gacaaggtgc tgatgccgct  1260
ggcgattcag gttcatcatg ccgtctgtga tggcttccat gtcggcagaa tgcttaatga  1320
attacaacag tactgcgatg agtggcaggg cggggcgtaa tttttttaag gcagttattg  1380
gtgcccttaa acgcctggtg ctacgcctga taagtgata taagcggat gaatggcaga   1440 aattcgtcga agcttaacac agaaaaaagc ccgcacctga cagtgcgggc ttttttttc   1500 gaccactgca gtctgttaca ggtcactaat accatctaag tagttgattc atagtgactg  1560
catatgttgt gttttacagt attatgtagt ctgtttttta tgcaaaatct aatttaatat  1620
attgatattt atatcatttt acgtttctcg ttcagctttt ttatactaac ttgagcgctg  1680
```

```
cggtgatgta atgcaggaaa gcaggctgga gct                                   1713

<210> SEQ ID NO 57
<211> LENGTH: 21
<212> TYPE: DNA
<213> ORGANISM: Artificial Sequence
<220> FEATURE:
<223> OTHER INFORMATION: Primer P22

<400> SEQUENCE: 57
ggatgtacgt ttgtcatgag t                                                  21

<210> SEQ ID NO 58
<211> LENGTH: 20
<212> TYPE: DNA
<213> ORGANISM: Artificial Sequence
<220> FEATURE:
<223> OTHER INFORMATION: Primer P23

<400> SEQUENCE: 58
tctcacgtag aacgatggca                                                    20

<210> SEQ ID NO 59
<211> LENGTH: 1430
<212> TYPE: DNA
<213> ORGANISM: Artificial Sequence
<220> FEATURE:
<223> OTHER INFORMATION: DNA fragment 20

<400> SEQUENCE: 59
ggatgtacgt ttgtcatgag tctcactctg ttgctaattg ccgttcgctc ctgaacatcc        60
actcgatctt cgccttcttc cggtttattg tgttttaacc acctgcccgt aaacctggag       120
aaccatcgcg tgtttcaaaa agttgacgcc tacgctggcg acccgattct tacgcttatg       180
gagcgtttta agaagaccc tcgcagcgac aaagtgaatt taagtatcgg tctgtactac        240
aacgaagacg gaattattcc acaactgcaa gccgtggcgg aggcggaagc gcgcctgaat       300
gcgcagcctc atggcgcttc gctttattta ccgatggaag ggcttaactg ctatcgccat       360
gccattgcgc cgctgctgtt tggtgcggac catccggtac tgaaacaaca gcgcgtagca       420
accattcaaa cccttggcgg ctccggggca ttgaaagtgg gcgcggattt cctgaaacgc       480
tacttcccgg aatcaggcgt ctgggtcagc gatcctacct gggaaaacca cgtagcaata       540
ttcgccgggg ctggattcga agtgagtact taccctggt atgacgaagc gactaacggc       600
gtgcgcttta atgacctgtt ggcgacgctg aaaacattac ctgcccgcag tattgtgttg       660
ctgcatccat gttgccacaa cccaacgggt gccgatctca ctaatgatca gtgggatgcg       720
gtgattgaaa ttctcaaagc ccgcgagctt attccattcc tcgatattgc ctatcaagga       780
tttggtgccg gtatggaaga ggatgcctac gctattcgcg ccattgccag cgctggatta       840
cccgctctgg tgagcaattc gttctcgaaa attttctccc tttacggcga gcgcgtcggc       900
ggactttctg ttatgtgtga agatgccgaa gccgctggcc gcgtactggg gcaattgaaa       960
gcaacagttc gccgcaacta ctccagcccg ccgaattttg gtgcgcaggt ggtggctgca      1020
gtgctgaatg acgaggcatt gaaagccagc tggctggcgg aagtagaaga gatgcgtact      1080
cgcattctgg caatgcgtca ggaattggtg aaggtattaa gcacagagat gccagaacgc      1140
aatttcgatt atctgcttaa tcagcgcggc atgttcagtt ataccggttt aagtgccgct      1200
caggttgacc gactacgtga agaatttggt gtctatctca tcgccagcgg tcgcatgtgt      1260
gtcgccgggt aaatacggc aaatgtacaa cgtgtggcaa aggcgtttgc tgcggtgatg       1320
```

```
taatgcagga aagcaggctg gagctaccca gcctgcagtg aaattaaact gtcgtcgctt    1380
tcactctttc tttatagatg attttttga tgccatcgtt ctacgtgaga               1430

<210> SEQ ID NO 60
<211> LENGTH: 1894
<212> TYPE: DNA
<213> ORGANISM: Artificial Sequence
<220> FEATURE:
<223> OTHER INFORMATION: DNA fragment 21

<400> SEQUENCE: 60
ggatgtacgt tgtcatgag tctcactctg ttgctaattg ccgttcgctc ctgaacatcc      60
actcgatctt cgccttcttc cggtttattg tgttttaacc acctgcccgt aaacctggag    120
aaccatcgcg tgtgaagcct gctttttat actaagttgg cattataaaa aagcattgct    180
tatcaatttg ttgcaacgaa caggtcacta tcagtcaaaa taaaatcatt atttgatttc    240
gaattctcat gtttgacagc ttatcatcga taagctttaa tgcggtagtt tatcacagtt    300
aaattgctaa cgcagtcagg caccgtgtat gaaatctaac aatgcgctca tcgtcatcct    360
cggcaccgtc accctggatg ctgtaggcat aggcttggtt atgccggtac tgccgggcct    420
cttgcgggat atcgtccatt ccgacagcat cgccagtcac tatggcgtgc tgctagcgct    480
atatgcgttg atgcaatttc tatgcgcacc cgttctcgga gcactgtccg accgctttgg    540
ccgccgccca gtcctgctcg cttcgctact tggagccact atcgactacg cgatcatggc    600
gaccacaccc gtcctgtgga tctccggata agtagacagc ctgataagtc gcacgaaaaa    660
caggtattga caacatgaag taacatgcag taagatacaa atcgctaggt aacactagca    720
gcgtcaaccg ggcgctctag ctagagccaa gctagcttgg ccggatccga gattttcagg    780
agctaaggaa gctaaaatgg agaaaaaaat cactggatat accaccgttg atatatccca    840
atggcatcgt aaagaacatt ttgaggcatt tcagtcagtt gctcaatgta cctataacca    900
gaccgttcag ctggatatta cggcctttt aaagaccgta agaaaaata agcacaagtt    960 ttatccggcc tttattcaca ttcttgcccg cctgatgaat gctcatccgg aattccgtat   1020
ggcaatgaaa gacggtgagc tggtgatatg ggatagtgtt cacccttgtt acaccgtttt   1080
ccatgagcaa actgaaacgt tttcatcgct ctggagtgaa taccacgacg atttccggca   1140
gtttctacac atatattcgc aagatgtggc gtgttacggt gaaaacctgg cctatttccc   1200
taaagggttt attgagaata tgttttcgt ctcagccaat ccctgggtga gtttcaccag   1260
ttttgattta aacgtggcca atatggacaa cttcttcgcc cccgttttca ccatgggcaa   1320
atattatacg caaggcgaca aggtgctgat gccgctggcg attcaggttc atcatgccgt   1380
ctgtgatggc ttccatgtcg gcagaatgct taatgaatta caacagtact gcgatgagtg   1440
gcagggcggg gcgtaatttt tttaaggcag ttattggtgc ccttaaacgc ctggtgctac   1500
gcctgaataa gtgataataa gcggatgaat ggcagaaatt cgtcgaagct taacacagaa   1560
aaaagcccgc acctgacagt gcgggctttt ttttttcgacc actgcagtct gttacaggtc   1620
actaatacca tctaagtagt tgattcatag tgactgcata tgttgtgttt tacagtatta   1680
tgtagtctgt ttttttatgca aaatctaatt taatatattg atatttatat catttttacgt   1740 ttctcgttca gctttttat actaacttga gcgctgcggt gatgtaatgc aggaaagcag   1800
gctggagcta cccagcctgc agtgaaatta actgtcgtc gctttcactc tttctttata   1860
gatgattttt ttgatgccat cgttctacgt gaga                                1894
```

<210> SEQ ID NO 61
<211> LENGTH: 64
<212> TYPE: DNA
<213> ORGANISM: Artificial Sequence
<220> FEATURE:
<223> OTHER INFORMATION: Primer P24

<400> SEQUENCE: 61
aattagctaa ttttacggat gcagaactca cgctggcgct caagttagta taaaaaagct    60
gaac                                                                 64

<210> SEQ ID NO 62
<211> LENGTH: 64
<212> TYPE: DNA
<213> ORGANISM: Artificial Sequence
<220> FEATURE:
<223> OTHER INFORMATION: Primer P25

<400> SEQUENCE: 62
cggaaagccc ggtcatttga ccgggcaagg ggattatgaa gcctgctttt ttatactaag    60
ttgg                                                                 64

<210> SEQ ID NO 63
<211> LENGTH: 1713
<212> TYPE: DNA
<213> ORGANISM: Artificial Sequence
<220> FEATURE:
<223> OTHER INFORMATION: DNA fragment 22

<400> SEQUENCE: 63
aattagctaa ttttacggat gcagaactca cgctggcgct caagttagta taaaaaagct    60
gaacgagaaa cgtaaaatga tataaatatc aatatattaa attagatttt gcataaaaaa   120
cagactacat aatactgtaa aacacaacat atgcagtcac tatgaatcaa ctacttagat   180
ggtattagtg acctgtaaca gactgcagtg gtcgaaaaaa aaagcccgca ctgtcaggtg   240
cgggcttttt tctgtgttaa gcttcgacga atttctgcca ttcatccgct tattatcact   300
tattcaggcg tagcaccagg cgtttaaggg caccaataac tgccttaaaa aaattacgcc   360
ccgccctgcc actcatcgca gtactgttgt aattcattaa gcattctgcc gacatggaag   420
ccatcacaga cggcatgatg aacctgaatc gccagcggca tcagcacctt gtcgccttgc   480
gtataatatt tgcccatggt gaaaacgggg gcgaagaagt tgtccatatt ggccacgttt   540
aaatcaaaac tggtgaaact cacccaggga ttggctgaga cgaaaaacat attctcaata   600
aaccctttag ggaaataggc caggttttca ccgtaacacg ccacatcttg cgaatatatg   660
tgtagaaact gccggaaatc gtcgtggtat tcactccaga gcgatgaaaa cgtttcagtt   720
tgctcatgga aaacggtgta acaagggtga acactatccc atatcaccag ctcaccgtct   780
ttcattgcca tacggaattc cggatgagca ttcatcaggc gggcaagaat gtgaataaag   840
gccggataaa acttgtgctt attttttctt tacggtcttta aaaaggccgt aatatccagc   900
tgaacggtct ggttataggt acattgagca actgactgaa atgcctcaaa atgttcttta   960
cgatgccatt gggatatatc aacggtggta tatccagtga tttttttctc cattttagct  1020
tccttagctc ctgaaaatct cggatccggc caagctagct tggctctagc tagagcgccc  1080
ggttgacgct gctagtgtta cctagcgatt tgtatcttac tgcatgttac ttcatgttgt  1140
caatacctgt ttttcgtgcg acttatcagg ctgtctactt atccgagat ccacaggacg   1200 ggtgtggtcg ccatgatcgc gtagtcgata gtggctccaa gtagcgaagc gagcaggact  1260

```
gggcggcggc caaagcggtc ggacagtgct ccgagaacgg gtgcgcatag aaattgcatc      1320
aacgcatata gcgctagcag cacgccatag tgactggcga tgctgtcgga atggacgata      1380
tcccgcaaga ggcccggcag taccggcata accaagccta tgcctacagc atccagggtg      1440
acggtgccga ggatgacgat gagcgcattg ttagatttca tacacggtgc ctgactgcgt      1500
tagcaattta actgtgataa actaccgcat taaagcttat cgatgataag ctgtcaaaca      1560
tgagaattcg aaatcaaata atgatttat tttgactgat agtgacctgt tcgttgcaac       1620
aaattgataa gcaatgcttt tttataatgc caacttagta taaaaaagca ggcttcataa      1680
tccccttgcc cggtcaaatg accgggcttt ccg                                   1713
```

<210> SEQ ID NO 64
<211> LENGTH: 22
<212> TYPE: DNA
<213> ORGANISM: Artificial Sequence
<220> FEATURE:
<223> OTHER INFORMATION: Primer P26

<400> SEQUENCE: 64

```
atgctgaaat atgtcaaccg at                                               22
```

<210> SEQ ID NO 65
<211> LENGTH: 22
<212> TYPE: DNA
<213> ORGANISM: Artificial Sequence
<220> FEATURE:
<223> OTHER INFORMATION: Primer P27

<400> SEQUENCE: 65

```
ggtaattgcg gttatttctg tt                                               22
```

<210> SEQ ID NO 66
<211> LENGTH: 5172
<212> TYPE: DNA
<213> ORGANISM: Artificial Sequence
<220> FEATURE:
<223> OTHER INFORMATION: DNA fragment 23

<400> SEQUENCE: 66

```
atgctgaaat atgtcaaccg atgaaaagcg tcggtagtta agcagaaatt aatatcgctt      60
actttaacca ccgcagcaca attagctaat tttacggatg cagaactcac gctggcggga     120
cgttttattt gcgtcagggt tgacatccgt ttttgtatcc agtaactcta aaagcatatc     180
gcattcatct ggagctgatt taatgactca catcgttcgc tttatcggtc tactactact     240
aaacgcatct tctttgcgcg gtagacgagt gagcggcatc cagcattaag ccagcacgca     300
gtcaaacaaa aaacccgcgc cattgcgcgg gttttttttat gcccgaagcg aggcgctcta    360
aaagagacaa ggacccaaac catgagccag caagtcatta ttttcgatac cacattgcgc     420
gacggtgaac aggcgttaca ggcaagcttg agtgtgaaag aaaaactgca aattgcgctg     480
gcccttgagc gtatgggtgt tgacgtgatg gaagtcggtt tccccgtctc ttcgccgggc     540
gattttgaat cggtgcaaac catcgcccgc caggttaaaa acagccgcgt atgtgcgtta     600
gctcgctgcg tggaaaaaga tatcgacgtg gcggccgaat ccctgaaagt cgccgaagcc     660
ttccgtattc ataccttatat tgccacttcg ccaatgcaca tcgccaccaa gctgcgcagc     720
acgctggacg aggtgatcga acgcgctatc tatatggtga aacgcgcccg taattacacc     780
gatgatgttg aattttcttg cgaagatgcc gggcgtacac ccattgccga tctggcgcga     840
```

```
gtggtcgaag cggcgattaa tgccggtgcc accaccatca acattccgga caccgtgggc    900
tacaccatgc cgtttgagtt cgccggaatc atcagcggcc tgtatgaacg cgtgcctaac    960
atcgacaaag ccattatctc cgtacatacc cacgacgatt tgggcctggc ggtcggaaac   1020
tcactggcgg cggtacatgc cggtgcacgc caggtggaag cgcaatgaa cgggatcggc   1080 gagcgtgccg gaaactgttc cctggaagaa gtcatcatgg cgatcaaagt tcgtaaggat   1140
attctcaacg tccacaccgc cattaatcac caggagatat ggcgcaccag ccagttagtt   1200
agccagattt gtaatatgcc gatcccggca acaaagcca ttgttggcag cggcgcattc   1260
gcacactcct ccggtataca ccaggatggc gtgctgaaaa accgcgaaaa ctacgaaatc   1320
atgacaccag aatctattgg tctgaaccaa atccagctga atctgacctc tcgttcgggg   1380 cgtgcgcgg tgaaacatcg catggatgag atggggtata agaaagtga atataattta   1440 gacaatttgt acgatgcttt cctgaagctg gcggacaaaa aaggtcaggt gtttgattac   1500
gatctggagg cgctggcctt catcggtaag cagcaagaag agccggagca tttccgtctg   1560
gattacttca gcgtgcagtc tggctctaac gatatcgcca ccgccgccgt caaactggcc   1620
tgtggcgaag aagtcaaagc agaagccgcc aacggtaacg gtccggtcga tgccgtctat   1680
caggcaatta accgcatcac tgaatataac gtcgaactgg tgaaatacag cctgaccgcc   1740
aaaggccacg gtaaagatgc gctgggtcag gtggatatcg tcgctaacta caacggtcgc   1800
cgcttccacg cgtcggcct ggctaccgat attgtcgagt catctgccaa agccatggtg   1860
cacgttctga acaatatctg gcgtgccgca gaagtcgaaa aagagttgca acgcaaagct   1920
caacacaacg aaaacaacaa ggaaaccgtg tgatgtcgaa gaattaccat attgccgtat   1980 tgccgggga cggtattggt ccggaagtga tgacccaggc gctgaaagtg ctggatgccg   2040
tgcgcaaccg ctttgcgatg cgcatcacca ccagccatta cgatgtaggc ggcgcagcca   2100
ttgataacca cgggcaacca ctgccgcctg cgacggttga aggttgtgag caagccgatg   2160
ccgtgctgtt tggctcggta ggcggcccga agtgggaaca tttaccacca gaccagcaac   2220
cagaacgcgg cgcgctgctg cctctgcgta agcacttcaa attattcagc aacctgcgcc   2280
cggcaaaact gtatcagggg ctggaagcat tctgtccgct gcgtgcagac attgccgcaa   2340
acggcttcga catcctgtgt gtgcgcgaac tgaccggcgg catctatttc ggtcagccaa   2400
aaggccgcga aggtagcgga caatatgaaa aagccttga taccgaggtg tataccgtt   2460 ttgagatcga acgtatcgcc cgcatcgcgt ttgaatctgc tcgcaagcgt cgccacaaag   2520
tgacgtcgat cgataaagcc aacgtgctgc aatcctctat tttatggcgg gagatcgtta   2580
acgagatcgc cacggaatac ccggatgtcg aactggcgca tatgtacatc gacaacgcca   2640
ccatgcagct gattaaagat ccatcacagt ttgacgttct gctgtgctcc aacctgtttg   2700
gcgacattct gtctgacgag tgcgcaatga tcactggctc gatggggatg ttgccttccg   2760
ccagcctgaa cgagcaaggt tttggactgt atgaaccggc gggcggctcg caccagata   2820 tcgcaggcaa aaacatcgcc aacccgattg cacaaatcct ttcgctggca ctgctgctgc   2880
gttacagcct ggatgccgat gatgcggctt gcgccattga acgcgccatt aaccgcgcat   2940
tagaagaagg cattcgcacc ggggatttag cccgtgcgc tgccgccgtt agtaccgatg   3000
aaatgggcga tatcattgcc cgctatgtag cagaagggt gtaatcatgg ctaagacgtt   3060
atacgaaaaa ttgttcgacg ctcacgttgt gtacgaagcc gaaaacgaaa ccccactgtt   3120
atatatcgac cgccacctgg tgcatgaagt gacctcaccg caggcgttcg atggtctgcg   3180
cgcccacggt cgcccggtac gtcagccggg caaaaccttc gctaccatgg atcacaacgt   3240
```

```
ctctacccag accaaagaca ttaatgcctg cggtgaaatg gcgcgtatcc agatgcagga      3300
actgatcaaa aactgcaaag aatttggcgt cgaactgtat gacctgaatc acccgtatca      3360
ggggatcgtc cacgtaatgg ggccggaaca gggcgtcacc ttgccgggga tgaccattgt      3420
ctgcggcgac tcgcataccg ccacccacgg cgcgtttggc gcactggcct ttggtatcgg      3480
cacttccgaa gttgaacacg tactggcaac gcaaaccctg aaacagggcc gcgcaaaaac      3540
catgaaaatt gaagtccagg gcaaagccgc gccgggcatt accgcaaaag atatcgtgct      3600
ggcaattatc ggtaaaaccg gtagcgcagg cggcaccggg catgtggtgg agttttgcgg      3660
cgaagcaatc cgtgatttaa gcatggaagg tcgtatgacc ctgtgcaata tggcaatcga      3720
aatgggcgca aaagccggtc tggttgcacc ggacgaaacc acctttaact atgtcaaagg      3780
ccgtctgcat gcgccgaaag gcaaagattt cgacgacgcc gttgcctact ggaaaaccct      3840
gcaaaccgac gaaggcgcaa ctttcgatac cgttgtcact ctgcaagcag aagaaatttc      3900
accgcaggtc acctggggca ccaatcccgg ccaggtgatt tccgtgaacg acaatattcc      3960
cgatccggct tcgtttgccg atccggttga acgcgcgtcg gcagaaaaag cgctggccta      4020
tatggggctg aaaccgggta ttccgctgac cgaagtggcc atcgacaaag tgtttatcgg      4080
ttcctgtacc aactcgcgca ttgaagattt acgcgcggca gcggagatcg ccaaagggcg      4140
aaaagtcgcg ccaggcgtgc aggcactggt ggttcccggc tctggcccgg taaaagccca      4200
ggcggaagcg gaaggtctgg ataaaatctt tattgaagcc ggttttgaat ggcgcttgcc      4260
tggctgctca atgtgtctgg cgatgaacaa cgaccgtctg aatccgggcg aacgttgtgc      4320
ctccaccagc aaccgtaact tgaaggccg ccaggggcgc ggcgggcgca cgcatctggt      4380
cagcccggca atggctgccg ctgctgctgt gaccggacat ttcgccgaca ttcgcaacat      4440
taaataagga gcacaccatg gcagagaaat ttatcaaaca cacaggcctg gtggttccgc      4500
tggatgccgc caatgtcgat accgatgcaa tcatcccgaa acagtttttg cagaaagtga      4560
cccgtacggg ttttggcgcg catctgtttt acgactggcg ttttctggat gaaaaaggcc      4620
aacagccaaa cccggacttc gtgctgaact cccgcagta tcagggcgct tccattttgc      4680
tggcacgaga aaacttcggc tgtggctctt cgcgtgagca cgcgccctgg gcattgaccg      4740
actacggttt taaagtggtg attgcgccga gttttgctga catcttctac ggcaatagct      4800
ttaacaacca gctgctgccg gtgaaattaa gcgatgcaga agtggacgaa ctgtttgcgc      4860
tggtgaaagc taatccgggg atccatttcg acgtggatct ggaagcgcaa gaggtgaaag      4920
cgggagagaa aacctatcgc tttaccatcg atgccttccg ccgccactgc atgatgaacg      4980
gtctggacag tattgggctt accttgcagc acgacgacgc cattgccgct tatgaagcaa      5040
aacaacctgc gtttatgaat taatcccctt gccccggtcaa atgaccgggc tttccgctat      5100
cgtccacgtc atcaaacgtc tttaaccttt gcggttaaaa ataatgcgac aacagaaata      5160
accgcaatta cc                                                          5172

<210> SEQ ID NO 67
<211> LENGTH: 1868
<212> TYPE: DNA
<213> ORGANISM: Artificial Sequence
<220> FEATURE:
<223> OTHER INFORMATION: DNA fragment 24

<400> SEQUENCE: 67
atgctgaaat atgtcaaccg atgaaaagcg tcggtagtta agcagaaatt aatatcgctt        60
```

```
actttaacca ccgcagcaca attagctaat tttacggatg cagaactcac gctggcgctc      120
aagttagtat aaaaaagctg aacgagaaac gtaaaatgat ataaatatca atatattaaa      180
ttagattttg cataaaaaac agactacata atactgtaaa acacaacata tgcagtcact      240
atgaatcaac tacttagatg gtattagtga cctgtaacag actgcagtgg tcgaaaaaaa      300
aagcccgcac tgtcaggtgc gggcttttt ctgtgttaag cttcgacgaa tttctgccat       360
tcatccgctt attatcactt attcaggcgt agcaccaggc gtttaagggc accaataact      420
gccttaaaaa aattacgccc cgccctgcca ctcatcgcag tactgttgta attcattaag      480
cattctgccg acatggaagc catcacagac ggcatgatga acctgaatcg ccagcggcat      540
cagcaccttg tcgccttgcg tataatattt gcccatggtg aaaacggggg cgaagaagtt      600
gtccatattg ccacgtttta aatcaaaact ggtgaaactc acccagggat tggctgagac      660
gaaaaacata ttctcaataa accctttagg gaaataggcc aggttttcac cgtaacacgc      720
cacatcttgc gaatatatgt gtagaaactg ccggaaatcg tcgtggtatt cactccagag      780
cgatgaaaac gtttcagttt gctcatggaa acggtgtaa caagggtgaa cactatccca       840
tatcaccagc tcaccgtctt tcattgccat acggaattcc ggatgagcat tcatcaggcg      900
ggcaagaatg tgaataaagg ccggataaaa cttgtgctta tttttcttta cggtctttaa      960
aaaggccgta atatccagct gaacggtctg gttataggta cattgagcaa ctgactgaaa     1020
tgcctcaaaa tgttctttac gatgccattg ggatatatca acgtggtat atccagtgat     1080 tttttctcc attttagctt ccttagctcc tgaaaatctc ggatccggcc aagctagctt     1140
ggctctagct agagcgcccg gttgacgctg ctagtgttac ctagcgattt gtatcttact     1200
gcatgttact tcatgttgtc aatacctgtt tttcgtgcga cttatcaggc tgtctactta     1260
tccggagatc cacaggacgg gtgtggtcgc catgatcgcg tagtcgatag tggctccaag     1320
tagcgaagcg agcaggactg ggcggcggcc aaagcggtcg acagtgctc cgagaacggg      1380 tgcgcataga aattgcatca acgcatatag cgctagcagc acgccatagt gactggcgat     1440
gctgtcggaa tggacgatat cccgcaagag gcccggcagt accggcataa ccaagcctat     1500
gcctacagca tccagggtga cggtgccgag atgacgatg agcgcattgt tagatttcat      1560
acacggtgcc tgactgcgtt agcaattta ctgtgataaa ctaccgcatt aaagcttatc      1620
gatgataagc tgtcaaacat gagaattcga aatcaaataa tgattttatt ttgactgata     1680
gtgacctgtt cgttgcaaca aattgataag caatgctttt ttataatgcc aacttagtat     1740
aaaaaagcag gcttcataat ccccttgccc ggtcaaatga ccgggctttc cgctatcgtc     1800
cacgtcatca acgtcttta accttgcgg ttaaaaataa tgcgacaaca gaaataaccg      1860
caattacc                                                              1868
```

<210> SEQ ID NO 68
<211> LENGTH: 284
<212> TYPE: DNA
<213> ORGANISM: Artificial Sequence
<220> FEATURE:
<223> OTHER INFORMATION: DNA fragment 25

<400> SEQUENCE: 68

```
ggatgtacgt ttgtcatgag tctcactctg ttgctaattg ccgttcgctc ctgaacatcc       60
actcgatctt cgccttcttc cggtttattg tgttttaacc acctgcccgt aaacctggag      120
aaccatcgcg tgtgaagcct gctttttat actaacttga gcgctgcggt gatgtaatgc      180
aggaaagcag gctggagcta cccagcctgc agtgaaatta aactgtcgtc gctttcactc     240
```

```
tttctttata gatgattttt ttgatgccat cgttctacgt gaga                284
```

<210> SEQ ID NO 69
<211> LENGTH: 70
<212> TYPE: DNA
<213> ORGANISM: Artificial Sequence
<220> FEATURE:
<223> OTHER INFORMATION: Ptac promoter

<400> SEQUENCE: 69

```
ccctgttgac aattaatcat cggctcgtat aatgtgtgga attgtgagcg gataacaatt    60
tcacacagga                                                           70
```